United States Patent
Namoto et al.

(10) Patent No.: US 11,279,921 B2
(45) Date of Patent: Mar. 22, 2022

(54) GLUCOAMYLASE VARIANTS AND POLYNUCLEOTIDES ENCODING SAME

(71) Applicant: NOVOZYMES A/S, Bagsvaerd (DK)

(72) Inventors: Tomoko Namoto, Chiba (JP); Noriko Tsutsumi, Chiba (JP); Keiichi Ayabe, Konakadaicho (JP); Zhengfang Kang, Raleigh, NC (US)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

(21) Appl. No.: 16/603,639

(22) PCT Filed: Apr. 10, 2018

(86) PCT No.: PCT/US2018/026815
§ 371 (c)(1),
(2) Date: Oct. 8, 2019

(87) PCT Pub. No.: WO2018/191215
PCT Pub. Date: Oct. 18, 2018

(65) Prior Publication Data
US 2020/0131491 A1    Apr. 30, 2020

Related U.S. Application Data

(60) Provisional application No. 62/483,990, filed on Apr. 11, 2017.

(51) Int. Cl.
*C12N 9/34* (2006.01)
*C12P 19/02* (2006.01)
*C12P 19/14* (2006.01)

(52) U.S. Cl.
CPC .......... *C12N 9/2428* (2013.01); *C12P 19/02* (2013.01); *C12P 19/14* (2013.01)

(58) Field of Classification Search
None
See application file for complete search history.

(56) References Cited

U.S. PATENT DOCUMENTS 10,494,685 B2 * 12/2019 Gupta .................. C12N 9/2428

FOREIGN PATENT DOCUMENTS

| WO | 2011/068803 A1 | 6/2011 |
| WO | 2014/177546 A2 | 11/2014 |
| WO | 2016/062875 A2 | 4/2016 |
| WO | 2017/066255 A1 | 4/2017 |

* cited by examiner

*Primary Examiner* — Anand U Desai
(74) *Attorney, Agent, or Firm* — David Fazzolare

(57) ABSTRACT

The present invention relates to glucoamylase variants having an increase in raw starch activity compared to the guy-coamylase disclosed as SEQ ID NO: 2, comprising one or more modifications in the catalytic domain and/or one or more modifications in the starch binding domain selected from: a) at least one, preferably at least two, preferably at least three, preferably at least four of: V18M, T43K, N112L, T116R, A117Q, G120S, A271F, Y295W, Q318Y; and/or b) Introducing at least three, preferably at least four substitutions selected from the group: S458C, S458SCGG, S458SGGC, A493V, A518K, E520Q, N527M, S540K, R, S(G)546P, T(V)549W, N503R, N539R+I541Y+T543V+A545S+S546GCGV+G547S+S548T+T549A. The present invention also relates to polynucleotides encoding the variants; nucleic acid constructs, vectors, and host cells comprising the polynucleotides; and methods of using the variants.

21 Claims, No Drawings
Specification includes a Sequence Listing.

GLUCOAMYLASE VARIANTS AND POLYNUCLEOTIDES ENCODING SAME

CROSS-REFERENCE TO RELATED APPLICATIONS

This application is a 35 U.S.C. 371 national application of international application no. PCT/US2018/026815 filed Apr. 10, 2018, which claims priority or the benefit under 35 U.S.C. 119 of U.S. provisional application no. 62/483,990 filed Apr. 11, 2017, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to glucoamylase variants, polynucleotides encoding the variants, methods of producing the variants, and methods of using the variants. Also described are the use of glucoamylase variants of the invention for starch conversion to produce fermentation products, such as ethanol, and syrups, such as glucose. The invention also relates to a composition comprising a glucoamylase variant of the invention.

Description of the Related Art

Glucoamylase (1,4-alpha-D-glucan glucohydrolase, EC 3.2.1.3) is an enzyme, which catalyzes the release of D-glucose from the non-reducing ends of starch or related oligo- and polysaccharide molecules. Glucoamylases are produced by several filamentous fungi and yeast, with those from *Aspergillus* being commercially most important.

Commercially, glucoamylases are used to convert starch containing material, which is already partially hydrolyzed by an alpha-amylase, to glucose. The glucose may then be converted directly or indirectly into a fermentation product using a fermenting organism. Examples of commercial fermentation products include alcohols (e.g., ethanol, methanol, butanol, 1,3-propanediol); organic acids (e.g., citric acid, acetic acid, itaconic acid, lactic acid, gluconic acid, gluconate, lactic acid, succinic acid, 2,5-diketo-D-gluconic acid); ketones (e.g., acetone); amino acids (e.g., glutamic acid); gases (e.g., $H_2$ and $CO_2$), and more complex compounds, including, for example, antibiotics (e.g., penicillin and tetracycline); enzymes; vitamins (e.g., riboflavin, $B_{12}$, beta-carotene); hormones, and other compounds which are difficult to produce synthetically. Fermentation processes are also commonly used in the consumable alcohol (e.g., beer and wine), dairy (e.g., in the production of yogurt and cheese) industries.

The end product may also be syrup. For instance, the end product may be glucose, but may also be converted, e.g., by glucose isomerase to fructose or a mixture composed almost equally of glucose and fructose. This mixture, or a mixture further enriched with fructose, is the most commonly used high fructose corn syrup (HFCS) commercialized throughout the world.

It is an object of the present invention to provide polypeptides having glucoamylase activity and polynucleotides encoding the polypeptides and which provide a high yield in fermentation product production processes, such as ethanol production processes.

WO 2011/068803 discloses glucoamylases isolated from the fungus *Gloeophyllum*, in particular, from *Gloeophyllum sepiarium* and *Gloeophyllum trabeum*.

The present invention provides glucoamylase variants with improved properties compared to its parent.

WO 2014/177546, WO 2016/062875 and WO 2017/066255 disclose glucoamylase variants of *Gloeophyllum* sp. having increased thermo-stability and increased specific activity.

In particular, it is desirable to provide glucoamylase variants that have both a good thermostability and a high hydrolytic activity towards raw starch (non-gelatinized starch).

SUMMARY OF THE INVENTION

In a first aspect the present invention relates to glucoamylase variants, having increased raw starch hydrolytic activity at pH=4.0, T=32° C., compared to the glucoamylase disclosed in SEQ ID NO: 2, wherein the variant is derived from a glucoamylase having a catalytic domain comprising amino acids 1-454 of SEQ ID NO: 2 or 1-454 of SEQ ID NO: 4, a linker comprising amino acids 455-462 of SEQ ID NO: 2 or amino acids 455-465 of SEQ ID NO: 4 and a starch binding domain comprising amino acids 463-556 of SEQ ID NO: 2 or amino acids 466-559 of SEQ ID NO: 4, and wherein the variant further comprises a combination of specific substitutions selected from the group consisting of:
V18M+T43K+S95P+A121P+Q318Y+A518K+N527M+T549W;
V18M+T43K+S95P+T116R+A121P+Q318Y+N539R+I541Y+T543V+A545S+S546PCGV+G547S+S548T+T549A;
S95P+A121P+Y295W+T116R+N539R+I541Y+T543V+A545S+S546PCGV+G547S+S548T+T549A;
T43K+S95P+A121P+Y295W+Q318Y+N539R+I541Y+T543V+A545S+S546PCGV+G547S+S548T+T549A;
T43K+S95P+G120S+A121P+Y295W+Q318Y+N539R+I541Y+T543V+A545S+S546GCGV+G547S+S548T+T549A;
V18M+T43K+S95P+T116R+A121P+Q318Y+S458SCGG+N527M+T(V)549W;
V18M+T43K+S95P+A121P+Q318Y+S458SCGG+N527M+T(V)549W+N503R;
V18M+T43K+S95P+A121P+Q318Y+N539R+I541Y+T543V+A545S+S546PCGV+G547S+S548T+T549A;
T43K+Q318Y+S95P+A121P+Y295W+S458SCGG+N527M+T(V)549W;
S95P+A121P+Y295W+G120S+N539R+I541Y+T543V+A545S+S546PCGV+G547S+S548T+T549A;
V18M+T43K+S95P+A121P+Q318Y+S458SCGG+N527M T(V)549W;
S95P+A121P+Y295W+N539R+I541Y+T543V+A545S+S546PCGV+G547S+S548T+T549A;
T43K+S95P+A121P+Y295W+Q318Y+N539R+I541Y+T543V+A545S+S546GCGV+G547S+S548T+T549A;
S95P+T116R+A121P+Y295W+N539R+I541Y+T543V+A545S+S546GCGV+G547S+S548T+T549A;
T43K+S95P+A121P+Y295W+Q318Y+N527M+T(V)549W+N503R;
S95P+A121P+Y295W+N539R+I541Y+T543V+A545S+S546GCGV+G547S+S548T+T549A;
V18M+T43K+S95P+A121P+A518K+N527M+T549W;

T43K+S95P+G120S+A121P+Y295W+Q318Y+A518K+N527M+T(V)549W;
T43K+S95P+A121P+Q318Y+A493V+A518K+N527M+T549W;
S95P+G120S+A121P+Y295W+N539R+I541Y+T543V+A545S+S546GCGV+G547S+S548T+T549A;
V18M+T43K+S95P+A121P+Y295W+A518K+N527M+T549W;
T43K+S95P+A121P+Y295W+Q318Y+N527M+T(V)549W;
T43K+S95P+A121P+Q318Y+N527M+T549W;
V18M+T43K+S95P+A121P+Q318Y+N527M+T549W;
S95P+A121P+Y295W+T116R+N527M+T(V)549W;
V18M+T43K+S95P+T116R+A121P+Q318Y+A493V+N527M+T549W;
V18M+T43K+S95P+A121P+Q318Y+A493V+N527M+T549W;
T43K+S95P+A121P+Y295W+Q318Y+A518K+N527M+T(V)549W;
S95P+A121P+Y295W+A117Q+N527M+T(V)549W;
V18M+T43K+S95P+A121P+Q318Y+A493V+A518K+N527M+T549W;
T43K+S95P+A121P+Q318Y+A518K+N527M+T549W;
V18M+T43K+S95P+T116R+A121P+Q318Y+N527M+T549W;
T43K+S95P+A121P+Q318Y+A493V+N527M+T549W;
S95P+T116R+A121P+Y295W+A518K+N527M+T(V)549W;
V18M+T43K+S95P+A121P+Q318Y+A518K+T(V)549W;
T43K+S95P+A121P+Y295W+Q318Y+A518K+N527M+T549W;
V18M+T43K+S95P+T116R+A121P+Q318Y+A518K+T549W;
S95P+A121P+Y295W+Q318Y+N527M+T(V)549W;
S95P+G120S+A121P+Y295W+N527M+T(V)549W;
S95P+A121P+Y295W+A518K+N527M+T(V)549W;
S95P+A121P+Y295W+N527M+T(V)549W;
S95P+N112L+A121P+Y295W+N527M+T(V)549W;
S95P+A121P+Y295W+N527M+T(V)549W;
V18M+T43K+S95P+A121P+Q318Y+A518K+N527M+T549W;
T43K+S95P+A121P+Y295W+Q318Y+N527M+T549W;
S95P+G120S+A121P+Y295W+A518K+N527M+T(V)549W;
S95P+N112L+A121P+Y295W+A518K+N527M+T(V)549W;
V18M+T43K+S95P+A121P+Q318Y+A518K+T549W;
S95P+A121P+Y295W+A493V+A518K+E520Q+T549W;
S95P+A121P+Y295W+A518K+N527M+T549W;
S95P+A121P+Y295W+A518K+T(V)549W;
S95P+A121P+Y295W+A518K+N527M;
S95P+A121P+Y295W+S458C+N539R+I541Y+T543V+A545S+S546GCGV+G547S+S548T+T549A;
S95P+A121P+Y295W+N527M+T549W;
S95P+A121P+A271F+Y295W+A518K+N527M+T549W;
S95P+A121P+Y295W+A493V;
S95P+A121P+Y295W+S540K;
S95P+A121P+Y295W+S540R;
S95P+A121P+Y295W+A518K+N527M;
S95P+A121P+Y295W+S458SGGC+N539R+I541Y+T543V+A545S+S546GCGV+G547S+S548T+T549A;
T43K+S95P+A121P+Y295W+N527M+T(V)549W;
S95P+A121P+Y295W+S458SCGG+N539R+I541Y+T543V+A545S+S546GCGV+G547S+S548T+T549A;
wherein the position numbering corresponds to amino acid positions in the amino acid sequence set forth in SEQ ID NO: 2; and wherein the variants have at least 85%, at least 90%, at least 95% identity, at least 96%, at least 97%, at least 98%, or at least 99%, but less than 100%, sequence identity to the amino acid sequence of SEQ ID NO: 2.

In a second aspect, the present invention relates to a glucoamylase variant, having increased raw starch hydrolytic activity at pH=4.0, T=32° C., compared to the glucoamylase disclosed in SEQ ID NO: 2, wherein the variant comprises the modifications selected from:
(i) replacing the starch binding domain amino acids 463-556 of SEQ ID NO: 2 with amino acids 466-559 of SEQ ID NO: 4; and/or
(ii) introducing the following substitutions and insertions: N539R+I541Y+T543V+A545S+S546GCGV+G547S+S548T+T549A using SEQ ID NO: 2 for numbering; wherein the variants have at least 85%, at least 90%, at least 95% identity, at least 96%, at least 97%, at least 98%, or at least 99%, but less than 100%, sequence identity to the amino acid sequence of SEQ ID NO: 2, and wherein the increase in raw starch hydrolytic activity compared to SEQ ID NO: 2 is at least 10%, such as at least 15%.

In a third aspect, the present invention relates to a glucoamylase variant, having increased raw starch hydrolytic activity at pH=4.0, T=32° C., compared to the glucoamylase disclosed in SEQ ID NO: 4, wherein the variant comprises the modifications of introducing the following substitutions and insertions: N539R+I541Y+T543V+A545S+S546GCGV+G547S+S548T+T549A using SEQ ID NO: 2 for numbering; wherein the variants have at least 85%, at least 90%, at least 95% identity, at least 96%, at least 97%, at least 98%, or at least 99%, but less than 100%, sequence identity to the amino acid sequence of SEQ ID NO: 4, and wherein the increase in raw starch hydrolytic activity compared to SEQ ID NO: 4 is at least 15%.

In a fourth aspect, the present invention relates to a glucoamylase variant, having increased raw starch hydrolytic activity at pH=4.0, T=32° C., compared to the glucoamylase disclosed in SEQ ID NO: 2, wherein the variant comprises the modifications selected from:
(i) replacing the starch binding domain amino acids 463-556 of SEQ ID NO: 2 with amino acids 466-559 of SEQ ID NO: 4; and/or
(ii) introducing the substitutions G459C+N527M+T(V)549W using SEQ ID NO: 2 for numbering; wherein the variants have at least 85%, at least 90%, at least 95% identity, at least 96%, at least 97%, at least 98%, or at least 99%, but less than 100%, sequence identity to the amino acid sequence of SEQ ID NO: 2, and wherein the increase in raw starch hydrolytic activity compared to SEQ ID NO: 2 is at least 10%, such as at least 15%.

In a fifth aspect, the present invention relates to a method for increasing raw starch hydrolysis activity of a glucoamylase comprising the steps:
(a) providing a hybrid glucoamylase comprising a first amino acid sequence consisting of amino acids 1-454 of SEQ ID NO: 2, a second amino acid sequence selected from amino acids 455-462 of SEQ ID NO: 2 or amino acids 455-465 of SEQ ID NO: 4, and a third amino acid sequence selected from amino acids 463-556 of SEQ ID NO: 2 or amino acids 466-559 of SEQ ID NO: 4; and/or
(b) introducing a combination of substitutions selected from at least one, preferably at least two, preferably at least three, preferably at least four of: V18M, T43K, N112L, T116R, A117Q, G120S, A271F, Y295W, Q318Y; and/or
(c) introducing at least three, preferably at least four substitutions selected from the group: S458C, S458SCGG, S458SGGC, A493V, A518K, E520Q, N527M, S540K, R,

S(G)546P, T(V)549W, N503R, N539R+I541Y+T543V+ A545S+S546GCGV+G547S+S548T+T549A.

In a sixth aspect, the present invention relates to a method for increasing raw starch hydrolysis activity of a glucoamylase comprising the steps:

(a) providing a hybrid glucoamylase comprising a first amino acid sequence consisting of amino acids 1-454 of SEQ ID NO: 2, a second amino acid sequence selected from amino acids 455-465 of SEQ ID NO: 4, and a third amino acid sequence selected from amino acids 466-559 of SEQ ID NO: 4; and/or (b) introducing a combination of substitutions selected from at least one of: V18M, T43K, T116R, G120S, Y295W, Q318Y; and/or (c) introducing one of 3 option: i) N539R+I541Y+ T543V+A545S+S546GCGV+G547S+S548T+T549A; ii) N539R+I541Y+T543V+A545S+S546PCGV+G547S+ S548T+T549A; iii) at least three substitutions selected from the group: S458SCGG, N527M, T(V)549W, and N503R.

The present invention also relates to polynucleotides encoding the variants of the invention; nucleic acid constructs, vectors, and host cells comprising the polynucleotides; and methods of producing the variants.

The present invention further relates to compositions comprising a glucoamylase variant of the invention.

In another aspect, the present invention relates to a use of the glucoamylase variant for producing a syrup or a fermentation product.

In still further aspects, the present invention relates to a process of producing a fermentation product from starch-containing material comprising the steps of:

(a) liquefying starch-containing material in the presence of an alpha amylase;

(b) saccharifying the liquefied material; and (c) fermenting with a fermenting organism;

wherein step (b) is carried out using at least a glucoamylase variant of the invention.

In a further aspect the present invention relates to a process of producing a fermentation product from starch-containing material, comprising the steps of:

(a) saccharifying starch-containing material at a temperature below the initial gelatinization temperature of said starch-containing material; and (b) fermenting with a fermenting organism, wherein step (a) is carried out using at least a glucoamylase variant of the invention.

In further aspects, the invention relates to a process of producing a syrup product from starch-containing material, comprising the step of:

(a) liquefying starch-containing material in the presence of an alpha amylase;

(b) saccharifying the liquefied material in the presence of a glucoamylase variant of the invention.

In another embodiment, the invention relates to a process of producing a syrup product from starch-containing material, comprising the step of saccharifying the starch-containing material in the presence of a glucoamylase variant of the invention, at a temperature below the initial gelatinization temperature of the starch-containing material.

Definitions

Glucoamylase: The term "glucoamylase" (1,4-alpha-D-glucan glucohydrolase, EC 3.2.1.3) is defined as an enzyme, which catalyzes the release of D-glucose from the non-reducing ends of starch or related oligo- and polysaccharide molecules. For purposes of the present invention, glucoamylase activity is determined according to the procedure described in the Examples herein. The Glucoamylase Unit (AGU) is defined as the amount of enzyme, which hydrolyses 1 micromole maltose per minute under the standard conditions 37° C., pH 4.3, substrate: maltose 23.2 mM, buffer: acetate 0.1 M, reaction time 5 minutes.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Fragment: The term "fragment" means a polypeptide having one or more (e.g., several) amino acids absent from the amino and/or carboxyl terminus of a mature polypeptide; wherein the fragment has glucoamylase activity.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Improved property: The term "improved property" means a characteristic associated with a variant that is improved compared to the parent. Such improved properties include, but are not limited to, increased raw starch hydrolytic activity, and increased thermo-stability.

Isolated: The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 1 to 556 of SEQ ID NO: 2. In another aspect the mature polypeptide is amino acids 1 to 559 of SEQ ID NO: 4. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having glucoamylase activity. In one aspect, the mature polypeptide coding sequence is nucleotides 52 to 1719 of SEQ ID NO: 1 Nucleotides 1 to 51 of SEQ ID NO: 1 encode a signal peptide. In another aspect, the mature polypeptide coding sequence is nucleotides 52 to 1728 of SEQ ID NO: 3 Nucleotides 1 to 51 of SEQ ID NO: 3 encode a signal peptide.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

Mutant: The term "mutant" means a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent or parent glucoamylase: The term "parent" or "parent glucoamylase" means any polypeptide with glucoamylase activity to which an alteration is made to produce the enzyme variants of the present invention.

Raw starch hydrolytic activity: The term "Raw starch hydrolytic activity" means that the hydrolytic activity was measured at pH 4.0 and T=32° C. at the conditions disclosed in the examples.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

$$(\text{Identical Residues} \times 100)/(\text{Length of Alignment} - \text{Total Number of Gaps in Alignment})$$

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

$$(\text{Identical Deoxyribonucleotides} \times 100)/(\text{Length of Alignment} - \text{Total Number of Gaps in Alignment})$$

Variant: The term "variant" means a polypeptide having glucoamylase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position. The variants of the present invention have at least 5%, e.g., at least 10%, at least 15%, at least 20%, at least 25%, at least 30%, at least 35%, at least 40%, or at least 50% increase in raw starch hydrolytic activity compared to the glucoamylase of the polypeptide of SEQ ID NO: 2.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Wild-type glucoamylase: The term "wild-type" glucoamylase means a glucoamylase expressed by a naturally occurring microorganism, such as a bacterium, yeast, or filamentous fungus found in nature. In one embodiment, the wild-type glucoamylase is derived from *Gloeophyllum sepiarium*. In the present disclosure, this is also denoted Gs-AMG. In another aspect, the wild-type glucoamylase is derived from *Gloeophyllum trabeum*. In the present disclosure, this is also denoted Gt-AMG.

Conventions for Designation of Variants

For purposes of the present invention, the polypeptide disclosed in SEQ ID NO: 2 is used to determine the corresponding amino acid residue in another glucoamylase. The amino acid sequence of another glucoamylase is aligned with the mature polypeptide disclosed in SEQ ID NO: 2, and based on the alignment, the amino acid position number corresponding to any amino acid residue in the polypeptide disclosed in SEQ ID NO: 2 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another glucoamylase can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537:_39-64; Katoh and Toh, 2010, *Bioinformatics* 26:_1899-1900), and EMBOSS EMMA employing ClustalW (1.83 or later; Thompson et al., 1994, *Nucleic Acids Research* 22: 4673-4680), using their respective default parameters.

When the other enzyme has diverged from the polypeptide of SEQ ID NO: 2 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the variants of the present invention, the nomenclature described below is adapted for ease of reference. The accepted IUPAC single letter or three letter amino acid abbreviation is employed.

Substitutions. For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions. For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions. For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---------|----------|
| 195     | 195 195a 195b |
| G       | G - K - A |

Multiple alterations. Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different alterations. Where different alterations can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants:
"Tyr167Gly+Arg170Gly", "Tyr167Gly+Arg170Ala", "Tyr167Ala+Arg170Gly", and "Tyr167Ala+Arg170Ala".

DETAILED DESCRIPTION OF THE INVENTION

The present invention relates to glucoamylase variants having improved properties over the parent glucoamylase. In a particular embodiment, the parent glucoamylase is a glucoamylase derived from *Gloeophyllum sepiarium*, such as the one disclosed herein as SEQ ID NO: 2 or from *Gloeophyllum trabeum*, such as the one disclosed herein as SEQ ID NO: 4. In a particular embodiment the improved property is selected from increased raw starch hydrolysis activity compared to the parent glucoamylase disclosed in SEQ ID NO: 2 or SEQ ID NO: 4. In one embodiment, the increase in raw starch hydrolysis was measured by raw starch degradation performance of the variants by release of glucose from granular starch after incubation of the glucoamylase variant in combination with a fungal alpha amylase (such as the one disclosed in SEQ ID NO: 6) at pH 4.0, T=32° C. (for detailed conditions see example 1). In a further embodiment, the variants according to the invention have increased thermo-stability compared to the parent glucoamylase disclosed in SEQ ID NO: 2 or SEQ ID NO: 4.

Variants

The present invention provides glucoamylase variants, having increased raw starch hydrolytic activity over the wild type parent glucoamylase. In particular, the parent glucoamylase is selected from a glucoamylase obtained from *Gloeophyllum sepiarium*, such as the one disclosed herein as SEQ ID NO: 2 or from *Gloeophyllum trabeum*, such as the one disclosed herein as SEQ ID NO: 4. The variants according to the invention are provided by introducing substitutions/insertions in the catalytic domain and/or in the linker and/or starch binding domain (SBD) as disclosed herein using SEQ ID NO: 2 for numbering. In case of a different parent glucoamylase such as, e.g., SEQ ID NO: 4, the parent glucoamylase is aligned with the glucoamylase of SEQ ID NO: 2 and the position corresponding to the position in SEQ ID NO: 2 is identified and modified as disclosed herein.

The substitutions introduced in the catalytic domain are, in a particular embodiment, selected from the group consisting of: V18M, T43K, N112L, T116R, A117Q, G120S, A271F, Y295W, Q318Y; particularly Y295W; T116R+Y295W; T43K+Y295W+Q318Y; V18M+T43K+Q318Y; V18M+T43K+T116R+Q318Y. The variants may further comprise the substitutions S95P+A121P. The substitutions/insertions introduced in the linker and SBD are preferably selected from the group: S458C, S458SCGG, S458SGGC, A493V, A518K, E520Q, N527M, S540K, R, S(G)546P, T(V)549W, N503R, N539R+I541Y+T543V+A545S+S546GCGV+G547S+S548T+T549A.

More specifically the present invention relates to a glucoamylase variant, having increased raw starch hydrolytic activity at pH=4.0, T=32° C., compared to the glucoamylase disclosed in SEQ ID NO: 2, wherein the variant is derived from a glucoamylase having a catalytic domain comprising amino acids 1-454 of SEQ ID NO: 2 or 1-454 of SEQ ID NO: 4, a linker comprising amino acids 455-462 of SEQ ID NO: 2 or amino acids 455-465 of SEQ ID NO: 4 and a starch binding domain comprising amino acids 463-556 of SEQ ID NO: 2 or amino acids 466-559 of SEQ ID NO: 4, and wherein the variant further comprises a combination of specific substitutions selected from the group consisting of:
V18M+T43K+S95P+A121P+Q318Y+A518K+N527M+T549W;
V18M+T43K+S95P+T116R+A121P+Q318Y+N539R+I541Y+T543V+A545S+S546PCGV+G547S+S548T+T549A;
S95P+A121P+Y295W+T116R+N539R+I541Y+T543V+A545S+S546PCGV+G547S+S548T+T549A;
T43K+S95P+A121P+Y295W+Q318Y+N539R+I541Y+T543V+A545S+S546PCGV+G547S+S548T+T549A;
T43K+S95P+G120S+A121P+Y295W+Q318Y+N539R+I541Y+T543V+A545S+S546GCGV+G547S+S548T+T549A;
V18M+T43K+S95P+T116R+A121P+Q318Y+S458SCGG+N527M+T(V)549W;
V18M+T43K+S95P+A121P+Q318Y+S458SCGG+N527M+T(V)549W+N503R;
V18M+T43K+S95P+A121P+Q318Y+N539R+I541Y+T543V+A545S+S546PCGV+G547S+S548T+T549A;
T43K+Q318Y+S95P+A121P+Y295W+S458SCGG+N527M+T(V)549W;
S95P+A121P+Y295W+G120S+N539R+I541Y+T543V+A545S+S546PCGV+G547S+S548T+T549A;
V18M+T43K+S95P+A121P+Q318Y+S458SCGG+N527M T(V)549W;
S95P+A121P+Y295W+N539R+I541Y+T543V+A545S+S546PCGV+G547S+S548T+T549A;
T43K+S95P+A121P+Y295W+Q318Y+N539R+I541Y+T543V+A545S+S546GCGV+G547S+S548T+T549A;
S95P+T116R+A121P+Y295W+N539R+I541Y+T543V+A545S+S546GCGV+G547S+S548T+T549A;
T43K+S95P+A121P+Y295W+Q318Y+N527M+T(V)549W+N503R;
S95P+A121P+Y295W+N539R+I541Y+T543V+A545S+S546GCGV+G547S+S548T+T549A;
V18M+T43K+S95P+A121P+A518K+N527M+T549W;
T43K+S95P+G120S+A121P+Y295W+Q318Y+A518K+N527M+T(V)549W;
T43K+S95P+A121P+Q318Y+A493V+A518K+N527M+T549W;
S95P+G120S+A121P+Y295W+N539R+I541Y+T543V+A545S+S546GCGV+G547S+S548T+T549A;
V18M+T43K+S95P+A121P+Y295W+A518K+N527M+T549W;
T43K+S95P+A121P+Y295W+Q318Y+N527M+T(V)549W;

T43K+S95P+A121P+Q318Y+N527M+T549W;
V18M+T43K+S95P+A121P+Q318Y+N527M+T549W;
S95P+A121P+Y295W+T116R+N527M+T(V)549W;
V18M+T43K+S95P+T116R+A121P+Q318Y+A493V+ N527M+T549W;
V18M+T43K+S95P+A121P+Q318Y+A493V+N527M+ T549W;
T43K+S95P+A121P+Y295W+Q318Y+A518K+N527M+T (V)549W;
S95P+A121P+Y295W+A117Q+N527M+T(V)549W;
V18M+T43K+S95P+A121P+Q318Y+A493V+A518K+ N527M+T549W;
T43K+S95P+A121P+Q318Y+A518K+N527M+T549W;
V18M+T43K+S95P+T116R+A121P+Q318Y+N527M+ T549W;
T43K+S95P+A121P+Q318Y+A493V+N527M+T549W;
S95P+T116R+A121P+Y295W+A518K+N527M+T(V) 549W;
V18M+T43K+S95P+A121P+Q318Y+A518K+T(V)549W;
T43K+S95P+A121P+Y295W+Q318Y+A518K+N527M+ T549W;
V18M+T43K+S95P+T116R+A121P+Q318Y+A518K+ T549W;
S95P+A121P+Y295W+Q318Y+N527M+T(V)549W;
S95P+G120S+A121P+Y295W+N527M+T(V)549W;
S95P+A121P+Y295W+A518K+N527M+T(V)549W;
S95P+A121P+Y295W+N527M+T(V)549W;
S95P+N112L+A121P+Y295W+N527M+T(V)549W;
S95P+A121P+Y295W+N527M+T(V)549W;
V18M+T43K+S95P+A121P+Q318Y+A518K+N527M+ T549W;
T43K+S95P+A121P+Y295W+Q318Y+N527M+T549W;
S95P+G120S+A121P+Y295W+A518K+N527M+T(V) 549W;
S95P+N112L+A121P+Y295W+A518K+N527M+T(V) 549W;
V18M+T43K+S95P+A121P+Q318Y+A518K+T549W;
S95P+A121P+Y295W+A493V+A518K+E520Q+T549W;
S95P+A121P+Y295W+A518K+N527M+T549W;
S95P+A121P+Y295W+A518K+T(V)549W;
S95P+A121P+Y295W+A518K+N527M;
S95P+A121P+Y295W+S458C+N539R+I541Y+T543V+ A545S+S546GCGV+G547S+S548T+T549A;
S95P+A121P+Y295W+N527M+T549W;
S95P+A121P+A271F+Y295W+A518K+N527M+T549W;
S95P+A121P+Y295W+A493V;
S95P+A121P+Y295W+S540K;
S95P+A121P+Y295W+S540R;
S95P+A121P+Y295W+A518K+N527M;
S95P+A121P+Y295W+S458SGGC+N539R+I541Y+ T543V+A545S+S546GCGV+G547S+S548T+T549A;
T43K+S95P+A121P+Y295W+N527M+T(V)549W;
S95P+A121P+Y295W+S458SCGG+N539R+I541Y+ T543V+A545S+S546GCGV+G547S+S548T+T549A;
wherein the position numbering corresponds to amino acid positions in the amino acid sequence set forth in SEQ ID NO: 2; and wherein the variants have at least 85%, at least 90%, at least 95% identity, at least 96%, at least 97%, at least 98%, or at least 99%, but less than 100%, sequence identity to the amino acid sequence of SEQ ID NO: 2.

In another embodiment the invention relates to a glucoamylase variant having increased raw starch hydrolytic activity at pH=4.0, T=32° C., compared to the glucoamylase disclosed in SEQ ID NO: 2, wherein the variant is derived from a glucoamylase having a catalytic domain comprising amino acids 1-454 of SEQ ID NO: 2, a linker comprising amino acids 455-465 of SEQ ID NO: 4 and a starch binding domain comprising amino acids 466-559 of SEQ ID NO: 4, and wherein the variant comprises a combination of specific substitutions selected from the group consisting of:
V18M+T43K+S95P+T116R+A121P+Q318Y+N539R+ I541Y+T543V+A545S+S546PCGV+G547S+S548T+ T549A;
S95P+A121P+Y295W+T116R+N539R+I541Y+T543V+ A545S+S546PCGV+G547S+S548T+T549A;
T43K+S95P+A121P+Y295W+Q318Y+N539R+I541Y+ T543V+A545S+S546PCGV+G547S+S548T+T549A;
T43K+S95P+G120S+A121P+Y295W+Q318Y+N539R+ I541Y+T543V+A545S+S546GCGV+G547S+S548T+ T549A;
V18M+T43K+S95P+T116R+A121P+Q318Y+ S458SCGG+N527M+T(V)549W;
V18M+T43K+S95P+A121P+Q318Y+S458SCGG+ N527M+T(V)549W+N503R;
V18M+T43K+S95P+A121P+Q318Y+N539R+I541Y+ T543V+A545S+S546PCGV+G547S+S548T+T549A;
T43K+S95P+A121P+Y295W+Q318Y+S458SCGG+ N527M+T(V)549W;
S95P+A121P+Y295W+G120S+N539R+I541Y+T543V+ A545S+S546PCGV+G547S+S548T+T549A;
V18M+T43K+S95P+A121P+Q318Y+S458SCGG+N527M T(V)549W;
S95P+A121P+Y295W+N539R+I541Y+T543V+A545S+ S546PCGV+G547S+S548T+T549A;
T43K+S95P+A121P+Y295W+Q318Y+N539R+I541Y+ T543V+A545S+S546GCGV+G547S+S548T+T549A;
S95P+T116R+A121P+Y295W+N539R+I541Y+T543V+ A545S+S546GCGV+G547S+S548T+T549A;
T43K+S95P+A121P+Y295W+Q318Y+N527M+T(V) 549W+N503R;
S95P+A121P+Y295W+N539R+I541Y+T543V+A545S+ S546GCGV+G547S+S548T+T549A; wherein the position numbering corresponds to amino acid positions in the amino acid sequence set forth in SEQ ID NO: 2; and wherein the variants have at least 85%, at least 90%, at least 95% identity, at least 96%, at least 97%, at least 98%, or at least 99%, but less than 100%, sequence identity to the amino acid sequence of SEQ ID NO: 2; and wherein the increase in raw starch hydrolytic activity compared to SEQ ID NO: 2 is at least 30%, at least 35%, such as at least 40%.

Particularly the variants may further comprise the substitutions G456S+P461S+E472Q+L481I+E489S+A493P+ E520Q.

In a specific embodiment, the invention relates to glucoamylase variants having increased raw starch hydrolytic activity at pH=4.0, T=32° C., compared to the glucoamylase disclosed in SEQ ID NO: 2, wherein the variant is derived from the glucoamylase of SEQ ID NO: 2, and wherein the variant comprises a combination of specific substitutions selected from the group consisting of:
V18M+T43K+S95P+A121P+Q318Y+A518K+N527M+ T549W;
V18M+T43K+S95P+A121P+A518K+N527M+T549W;
T43K+S95P+A121P+Q318Y+A493V+A518K+N527M+ T549W;
V18M+T43K+S95P+A121P+Y295W+A518K+N527M+ T549W;
T43K+S95P+A121P+Q318Y+N527M+T549W;
V18M+T43K+S95P+A121P+Q318Y+N527M+T549W;
V18M+T43K+S95P+T116R+A121P+Q318Y+A493V+ N527M+T549W;
V18M+T43K+S95P+A121P+Q318Y+A493V+N527M+ T549W;

V18M+T43K+S95P+A121P+Q318Y+A493V+A518K+
N527M+T549W;
T43K+S95P+A121P+Q318Y+A518K+N527M+T549W;
V18M+T43K+S95P+T116R+A121P+Q318Y+N527M+
T549W;
T43K+S95P+A121P+Q318Y+A493V+N527M+T549W;
T43K+S95P+A121P+Y295W+Q318Y+A518K+N527M+
T549W;
V18M+T43K+S95P+T116R+A121P+Q318Y+A518K+
T549W;
V18M+T43K+S95P+A121P+Q318Y+A518K+N527M+
T549W;
T43K+S95P+A121P+Y295W+Q318Y+N527M+T549W;
V18M+T43K+S95P+A121P+Q318Y+A518K+T549W;
S95P+A121P+Y295W+A493V+A518K+E520Q+T549W;
S95P+A121P+Y295W+A518K+N527M+T549W;
S95P+A121P+Y295W+N527M+T549W;
S95P+A121P+A271F+Y295W+A518K+N527M+T549W;
S95P+A121P+Y295W+A493V;
S95P+A121P+Y295W+S540K;
S95P+A121P+Y295W+S540R;
S95P+A121P+Y295W+A518K+N527M; wherein the position numbering corresponds to amino acid positions in the amino acid sequence set forth in SEQ ID NO: 2; and wherein the variants have at least 85%, at least 90%, at least 95% identity, at least 96%, at least 97%, at least 98%, or at least 99%, but less than 100%, sequence identity to the amino acid sequence of SEQ ID NO: 2; and wherein the increase in raw starch hydrolytic activity compared to SEQ ID NO: 2 is at least 5%.

In a further specific embodiment, the present invention relates to a glucoamylase variant having increased raw starch hydrolytic activity at pH=4.0, T=32° C., compared to the glucoamylase disclosed in SEQ ID NO: 2, wherein the variant is derived from the glucoamylase of SEQ ID NO: 2, and wherein the variant comprises a combination of specific substitutions selected from the group consisting of:
V18M+T43K+S95P+A121P+Q318Y+A518K+N527M+
T549W;
V18M+T43K+S95P+A121P+A518K+N527M+T549W;
T43K+S95P+A121P+Q318Y+A493V+A518K+N527M+
T549W;
V18M+T43K+S95P+A121P+Y295W+A518K+N527M+
T549W;
T43K+S95P+A121P+Q318Y+N527M+T549W;
V18M+T43K+S95P+A121P+Q318Y+N527M+T549W;
V18M+T43K+S95P+T116R+A121P+Q318Y+A493V+
N527M+T549W;
V18M+T43K+S95P+A121P+Q318Y+A493V+N527M+
T549W;
V18M+T43K+S95P+A121P+Q318Y+A493V+A518K+
N527M+T549W;
T43K+S95P+A121P+Q318Y+A518K+N527M+T549W;
V18M+T43K+S95P+T116R+A121P+Q318Y+N527M+
T549W;
T43K+S95P+A121P+Q318Y+A493V+N527M+T549W;
T43K+S95P+A121P+Y295W+Q318Y+A518K+N527M+
T549W;
V18M+T43K+S95P+T116R+A121P+Q318Y+A518K+
T549W;
V18M+T43K+S95P+A121P+Q318Y+A518K+N527M+
T549W;
T43K+S95P+A121P+Y295W+Q318Y+N527M+T549W;
V18M+T43K+S95P+A121P+Q318Y+A518K+T549W;
S95P+A121P+Y295W+A493V+A518K+E520Q+T549W;
S95P+A121P+Y295W+A518K+N527M+T549W;
wherein the position numbering corresponds to amino acid positions in the amino acid sequence set forth in SEQ ID NO: 2; and wherein the variants have at least 85%, at least 90%, at least 95% identity, at least 96%, at least 97%, at least 98%, or at least 99%, but less than 100%, sequence identity to the amino acid sequence of SEQ ID NO: 2; and wherein the increase in raw starch hydrolytic activity compared to SEQ ID NO: 2 is at least 20%.

In a further specific embodiment, the present invention relates to a glucoamylase variant having increased raw starch hydrolytic activity at pH=4.0, T=32° C., compared to the glucoamylase disclosed in SEQ ID NO: 2, wherein the variant is derived from the glucoamylase of SEQ ID NO: 2, and wherein the variant comprises a combination of specific substitutions selected from: V18M+T43K+S95P+A121P+
Q318Y+A518K+N527M+T549W; wherein the position numbering corresponds to amino acid positions in the amino acid sequence set forth in SEQ ID NO: 2; and wherein the variants have at least 85%, at least 90%, at least 95% identity, at least 96%, at least 97%, at least 98%, or at least 99%, but less than 100%, sequence identity to the amino acid sequence of SEQ ID NO: 2; and wherein the increase in raw starch hydrolytic activity compared to SEQ ID NO: 2 is at least 5%, at least 10%, at least 15%, particularly at least 20%.

In another specific embodiment, the invention relates to a glucoamylase variant having increased raw starch hydrolytic activity at pH=4.0, T=32° C., compared to the glucoamylase disclosed in SEQ ID NO: 2, wherein the variant is derived from a glucoamylase having a catalytic domain comprising amino acids 1-454 of SEQ ID NO: 2, a linker comprising amino acids 455-465 of SEQ ID NO: 4 and a starch binding domain comprising amino acids 466-559 of SEQ ID NO: 4, and wherein the variant comprises a combination of specific substitutions selected from the group consisting of:
T43K+S95P+G120S+A121P+Y295W+Q318Y+A518K+
N527M+T(V)549W;
S95P+G120S+A121P+Y295W+N539R+I541Y+T543V+
A545S+S546GCGV+G547S+S548T+T549A;
T43K+S95P+A121P+Y295W+Q318Y+N527M+T(V)
549W;
S95P+A121P+Y295W+T116R+N527M+T(V)549W;
T43K+S95P+A121P+Y295W+Q318Y+A518K+N527M+T
(V)549W;
S95P+A121P+Y295W+A117Q+N527M+T(V)549W;
S95P+T116R+A121P+Y295W+A518K+N527M+T(V)
549W;
V18M+T43K+S95P+A121P+Q318Y+A518K+T(V)549W;
S95P+A121P+Y295W+Q318Y+N527M+T(V)549W;
S95P+G120S+A121P+Y295W+N527M+T(V)549W;
S95P+A121P+Y295W+A518K+N527M+T(V)549W;
S95P+N112L+A121P+Y295W+N527M+T(V)549W;
S95P+A121P+Y295W+N527M+T(V)549W;
S95P+G120S+A121P+Y295W+A518K+N527M+T(V)
549W;
S95P+N112L+A121P+Y295W+A518K+N527M+T(V)
549W;
S95P+A121P+Y295W+A518K+T(V)549W;
S95P+A121P+Y295W+A518K+N527M;
S95P+A121P+Y295W+S458C+N539R+I541Y+T543V+
A545S+S546GCGV+G547S+S548T+T549A;
S95P+A121P+Y295W+S458SGGC+N539R+I541Y+
T543V+A545S+S546GCGV+G547S+S548T+T549A;
T43K+S95P+A121P+Y295W+N527M+T(V)549W;
S95P+A121P+Y295W+S458SCGG+N539R+I541Y+
T543V+A545S+S546GCGV+G547S+S548T+T549A;

wherein the position numbering corresponds to amino acid positions in the amino acid sequence set forth in SEQ ID NO: 2; and wherein the variants have at least 85%, at least 90%, at least 95% identity, at least 96%, at least 97%, at least 98%, or at least 99%, but less than 100%, sequence identity to the amino acid sequence of SEQ ID NO: 2; and wherein the increase in raw starch hydrolytic activity compared to SEQ ID NO: 2 is at least 2%.

In another specific embodiment, the invention relates to a glucoamylase variant having increased raw starch hydrolytic activity at pH=4.0, T=32° C., compared to the glucoamylase disclosed in SEQ ID NO: 2, wherein the variant is derived from a glucoamylase having a catalytic domain comprising amino acids 1-454 of SEQ ID NO: 2, a linker comprising amino acids 455-465 of SEQ ID NO: 4 and a starch binding domain comprising amino acids 466-559 of SEQ ID NO: 4, and wherein the variant comprises a combination of specific substitutions selected from the group consisting of:
T43K+S95P+G120S+A121P+Y295W+Q318Y+A518K+ N527M+T(V)549W;
S95P+G120S+A121P+Y295W+N539R+I541Y+T543V+ A545S+S546GCGV+G547S+S548T+T549A;
T43K+S95P+A121P+Y295W+Q318Y+N527M+T(V) 549W;
S95P+A121P+Y295W+T116R+N527M+T(V)549W;
T43K+S95P+A121P+Y295W+Q318Y+A518K+N527M+T (V)549W;
S95P+A121P+Y295W+A117Q+N527M+T(V)549W;
S95P+T116R+A121P+Y295W+A518K+N527M+T(V) 549W;
V18M+T43K+S95P+A121P+Q318Y+A518K+T(V)549W;
S95P+A121P+Y295W+Q318Y+N527M+T(V)549W;
S95P+G120S+A121P+Y295W+N527M+T(V)549W;
S95P+A121P+Y295W+A518K+N527M+T(V)549W;
S95P+N112L+A121P+Y295W+N527M+T(V)549W;
S95P+A121P+Y295W+N527M+T(V)549W;
S95P+G120S+A121P+Y295W+A518K+N527M+T(V) 549W;
S95P+N112L+A121P+Y295W+A518K+N527M+T(V) 549W;
S95P+A121P+Y295W+A518K+T(V)549W;
S95P+A121P+Y295W+A518K+N527M;
S95P+A121P+Y295W+S458C+N539R+I541Y+T543V+ A545S+S546GCGV+G547S+S548T+T549A; wherein the position numbering corresponds to amino acid positions in the amino acid sequence set forth in SEQ ID NO: 2; and wherein the variants have at least 85%, at least 90%, at least 95% identity, at least 96%, at least 97%, at least 98%, or at least 99%, but less than 100%, sequence identity to the amino acid sequence of SEQ ID NO: 2;
and wherein the increase in raw starch hydrolytic activity compared to SEQ ID NO: 2 is at least 15%, such as at least 20%.

In a further aspect, the present invention relates to a glucoamylase variant, having increased raw starch hydrolytic activity at pH=4.0, T=32° C., compared to the glucoamylase disclosed in SEQ ID NO: 2, wherein the variant comprises the modifications selected from:
  i) replacing the starch binding domain amino acids 463-556 of SEQ ID NO: 2 with amino acids 466-559 of SEQ ID NO: 4; and/or
  ii) introducing the following substitutions and insertions: N539R+I541Y+T543V+A545S+S546GCGV+G547S+ S548T+T549A using SEQ ID NO: 2 for numbering; wherein the variants have at least 85%, at least 90%, at least 95% identity, at least 96%, at least 97%, at least 98%, or at least 99%, but less than 100%, sequence identity to the amino acid sequence of SEQ ID NO: 2, and wherein the increase in raw starch hydrolytic activity compared to SEQ ID NO: 2 is at least 10%, such as at least 15%.

In particular, the variants may further comprise any of the substitutions: V18M, T43K, T116R, A271F, Y295W, Q318Y; particularly, Y295W; T116R+Y295W; T43K+ Y295W+Q318Y; V18M+T43K+Q318Y; V18M+T43K+ T116R+Q318Y.

In a further aspect the present invention relates to a glucoamylase variant, having increased raw starch hydrolytic activity at pH=4.0, T=32° C., compared to the glucoamylase disclosed in SEQ ID NO: 4, wherein the variant comprises the modifications of introducing the following substitutions and insertions: N539R+I541Y+T543V+ A545S+S546GCGV+G547S+S548T+T549A using SEQ ID NO: 2 for numbering; wherein the variants have at least 85%, at least 90%, at least 95% identity, at least 96%, at least 97%, at least 98%, or at least 99%, but less than 100%, sequence identity to the amino acid sequence of SEQ ID NO: 4, and wherein the increase in raw starch hydrolytic activity compared to SEQ ID NO: 4 is at least 15%.

In particular, the variants may further comprise any of the substitutions: V18M, T43K, T116R, A271F, Y295W, Q318Y; particularly, Y295W; T116R+Y295W; T43K+ Y295W+Q318Y; V18M+T43K+Q318Y; V18M+T43K+ T116R+Q318Y.

In a further aspect, the present invention relates to a glucoamylase variant, having increased raw starch hydrolytic activity at pH=4.0, T=32° C., compared to the glucoamylase disclosed in SEQ ID NO: 2, wherein the variant comprises the modifications selected from:
  i) replacing the starch binding domain amino acids 463-556 of SEQ ID NO: 2 with amino acids 466-559 of SEQ ID NO: 4; and/or
  ii) introducing the substitutions G459C+N527M+T(V) 549W using SEQ ID NO: 2 for numbering; wherein the variants have at least 85%, at least 90%, at least 95% identity, at least 96%, at least 97%, at least 98%, or at least 99%, but less than 100%, sequence identity to the amino acid sequence of SEQ ID NO: 2, and wherein the increase in raw starch hydrolytic activity compared to SEQ ID NO: 2 is at least 10%, such as at least 15%.

In particular, the variants may further comprising any of the substitutions:
  V18M, T43K, T116R, A271F, Y295W, Q318Y; particularly Y295W; T116R+Y295W; T43K+Y295W+Q318Y; V18M+T43K+Q318Y; V18M+T43K+T116R+Q318Y.

Preferably all variants of the invention comprise S95P+ A121P.

In a further aspect the invention relates to methods of increasing raw starch hydrolytic activity of a parent glucoamylase by introducing substitutions/insertions in the catalytic domain and/or in the linker and/or starch binding domain (SBD) as disclosed herein using SEQ ID NO: 2 for numbering. In case of a different parent glucoamylase such as, e.g., SEQ ID NO: 4, the parent glucoamylase is aligned with the glucoamylase of SEQ ID NO: 2 and the position corresponding to the position in SEQ ID NO: 2 is identified and modified as disclosed herein.

Thus, in one embodiment the present invention relates to a method for increasing raw starch hydrolysis activity of a glucoamylase comprising the steps:
  (a) providing a hybrid glucoamylase comprising a first amino acid sequence consisting of amino acids 1-454 of SEQ ID NO: 2, a second amino acid sequence selected from amino acids 455-462 of SEQ ID NO: 2 or amino acids 455-465 of SEQ ID NO: 4, and a third amino acid sequence selected from amino acids 463-556 of SEQ ID NO: 2 or amino acids 466-559 of SEQ ID NO: 4; and/or (b) introducing a combination of substitutions selected from at least one, preferably at least two, preferably at least three, preferably at least four of: V18M, T43K, N112L, T116R, A117Q, G120S, A271F, Y295W, Q318Y; and/or (c) Introducing at least three, preferably at least four substitutions selected from the group: S458C, S458SCGG, S458SGGC, A493V, A518K, E520Q, N527M, S540K, R, S(G)546P, T(V)549W, N503R, N539R+I541Y+T543V+A545S+S546GCGV+G547S+S548T+T549A.

Preferably the substitutions S95P+A121P are also introduced.

In a further embodiment the present invention relates to a method for increasing raw starch hydrolysis activity of a glucoamylase comprising the steps:

(a) providing a hybrid glucoamylase comprising a first amino acid sequence consisting of amino acids 1-454 of SEQ ID NO: 2, a second amino acid sequence selected from amino acids 455-465 of SEQ ID NO: 4, and a third amino acid sequence selected from amino acids 466-559 of SEQ ID NO: 4; and/or (b) introducing a combination of substitutions selected from at least one of: V18M, T43K, T116R, G120S, Y295W, Q318Y; and/or (c) introducing one of 3 option: i) N539R+I541Y+T543V+A545S+S546GCGV+G547S+S548T+T549A; ii) N539R+I541Y+T543V+A545S+S546PCGV+G547S+S548T+T549A; iii) at least three substitutions selected from the group: S458SCGG, N527M, T(V)549W, and N503R.

Preferably the substitutions S95P+A121P are also introduced.

The variants may further comprise one or more additional alterations at one or more (e.g., several) other positions. For example, the variants according to the invention may have at least 85%, at least 90%, at least 95% identity, at least 96%, at least 97%, at least 98%, or at least 99%, but less than 100%, sequence identity to the amino acid sequence of SEQ ID NO: 2 or SEQ ID NO:4.

In one embodiment, the number of alterations are 1-20, e.g., 1-10 and 1-5, such as 1, 2, 3, 4, 5, 6, 7, 8, 9 or 10.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for glucoamylase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

In one embodiment, the variants have increased raw starch activity compared to the parent glucoamylase. In an embodiment, the variant has increased specific activity compared to the parent enzyme.

In an embodiment, the variant has increased thermostability compared to the parent enzyme.

Parent Glucoamylase

In one embodiment the parent glucoamylase is derived from *Gloeophyllum*, particularly *Gloeophyllum sepiarium*. The parent glucoamylase may be (a) a polypeptide having at least 85% sequence identity to the polypeptide of SEQ ID NO: 2; (b) a polypeptide encoded by a polynucleotide that hybridizes under high stringency conditions with (i) the mature polypeptide coding sequence of SEQ ID NO: 1, or (ii) the full-length complement of (i); or (c) a polypeptide encoded by a polynucleotide having at least 85% sequence identity to the mature polypeptide coding sequence of SEQ ID NO: 1.

In an aspect, the parent has a sequence identity to the polypeptide of SEQ ID NO: 2 of at least 85%, at least 90%, at least 91%, at least 92%, at least 93%, at least 94%, at least 95%, at least 96%, at least 97%, at least 98%, at least 99%, or 100%, which have glucoamylase activity. In one aspect, the amino acid sequence of the parent differs by up to 10 amino acids, e.g., 1, 2, 3, 4, 5, 6, 7, 8, 9, or 10, from the polypeptide of SEQ ID NO: 2.

In another aspect, the parent comprises or consists of the amino acid sequence of SEQ ID NO: 2.

In another aspect, the parent is encoded by a polynucleotide that hybridizes under high stringency conditions, or very high stringency conditions with (i) the mature polypeptide coding sequence of SEQ ID NO: 1, (ii) or the full-length complement of (i) (Sambrook et al., 1989, *Molecular Cloning, A Laboratory Manual*, 2d edition, Cold Spring Harbor, N.Y.).

In one embodiment the parent glucoamylase is derived from *Gloeophyllum*, particularly *Gloeophyllum trabeum*. The parent glucoamylase may be (a) a polypeptide having at least 85% sequence identity to the polypeptide of SEQ ID NO: 4; (b) a polypeptide encoded by a polynucleotide that hybridizes under high stringency conditions with (i) the mature polypeptide coding sequence of SEQ ID NO: 3, or (ii) the full-length complement of (i); or (c) a polypeptide encoded by a polynucleotide having at least 85% sequence identity to the mature polypeptide coding sequence of SEQ ID NO: 3.

In an aspect, the parent has a sequence identity to the polypeptide of SEQ ID NO: 4 of at least 85%, at least 90%, at least 91%, at least 92%, at least 93%, at least 94%, at least 95%, at least 96%, at least 97%, at least 98%, at least 99%, or 100%, which have glucoamylase activity.

In one aspect, the amino acid sequence of the parent differs by up to 10 amino acids, e.g., 1, 2, 3, 4, 5, 6, 7, 8, 9, or 10, from the polypeptide of SEQ ID NO: 4.

In another aspect, the parent comprises or consists of the amino acid sequence of SEQ ID NO: 4.

In another aspect, the parent is encoded by a polynucleotide that hybridizes under high stringency conditions, or very high stringency conditions with (i) the mature polypeptide coding sequence of SEQ ID NO: 3, (ii) or the full-length complement of (i) (Sambrook et al., 1989, *Molecular Cloning, A Laboratory Manual*, 2d edition, Cold Spring Harbor, N.Y.).

In another embodiment, the parent is encoded by a polynucleotide having a sequence identity to the mature polypeptide coding sequence of SEQ ID NO: 1 or SEQ ID NO: 3 of at least 85%, at least 90%, at least 91%, at least 92%, at least 93%, at least 94%, at least 95%, at least 96%, at least 97%, at least 98%, at least 99%, or 100%.

The polypeptide may be a hybrid polypeptide in which a region of one polypeptide is fused at the N-terminus or the C-terminus of a region of another polypeptide.

The parent may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The parent may be a fungal glucoamylase. For example, the parent may be a *Gloeophyllum* glucoamylase.

In another aspect, the parent is a *Gloeophyllum trabeum*, or *Gloeophyllum sepiarium*.

In another aspect, the parent is a *Gloeophyllum sepiarium* glucoamylase (Gs AMG), e.g., the glucoamylase of SEQ ID NO: 2 or a *Gloeophyllum trabeum* glucoamylase (Gt AMG), e.g., the glucoamylase of SEQ ID NO: 4.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually, the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and regiondirected mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to polynucleotides encoding a variant of the present invention.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences. In a particular embodiment, at least one control sequence is heterologous to the polynucleotide encoding a variant of the present invention. Thus, the nucleic acid construct would not be found in nature.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

The control sequence may also be a transcription terminator, which is recognized by a host cell to terminate transcription. The terminator sequence is operably linked to the 3'-terminus of the polynucleotide encoding the variant. Any terminator that is functional in the host cell may be used.

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

The control sequence may also be an mRNA stabilizer region downstream of a promoter and upstream of the coding sequence of a gene which increases expression of the gene.

The control sequence may also be a leader, a nontranslated region of an mRNA that is important for translation by the host cell. The leader sequence is operably linked to the 5'-terminus of the polynucleotide encoding the variant. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

The control sequence may also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may e.g., be obtained from the genes for *Myceliophthora thermophila* laccase (WO 95/33836), *Rhizomucor miehei* aspartic proteinase.

Where both signal peptide and propeptide sequences are present, the propeptide sequence is positioned next to the N-terminus of the variant and the signal peptide sequence is positioned next to the N-terminus of the propeptide sequence.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked with the regulatory sequence.

Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Preferred for use in an *Aspergillus* cell are *Aspergillus nidulans* or *Aspergillus oryzae* amdS and pyrG genes.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid construct encoding a variant of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a eukaryote.

The host cell may be a eukaryote, such as a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (*Endomycetales*), basidiosporogenous yeast, and yeast belonging to the Fungi Imperfecti (*Blastomycetes*). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series* No. 9, 1980).

The yeast host cell may be a *Candida*, *Hansenula*, *Kluyveromyces*, *Pichia*, *Saccharomyces*, *Schizosaccharomyces*, or *Yarrowia* cell, such as a *Kluyveromyces lactis*, *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, *Saccharomyces oviformis*, or *Yarrowia lipolytica* cell.

In a particular embodiment, the host yeast cell expressing the glucoamylase variants of the invention is used in a process of the invention for producing a fermentation product from starch containing material, more particularly the host cell is a *Saccharomyces cerevisiae* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium*, *Aspergillus*, *Aureobasidium*, *Bjerkandera*, *Ceriporiopsis*, *Chrysosporium*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium*, *Trametes*, or *Trichoderma* cell.

For example, the filamentous fungal host cell may be an *Aspergillus awamori*, *Aspergillus foetidus*, *Aspergillus fumigatus*, *Aspergillus japonicus*, *Aspergillus nidulans*, *Aspergillus niger*, *Aspergillus oryzae*, *Bjerkandera adusta*, *Ceriporiopsis aneirina*, *Ceriporiopsis caregiea*, *Ceriporiopsis gilvescens*, *Ceriporiopsis pannocinta*, *Ceriporiopsis rivulosa*, *Ceriporiopsis subrufa*, *Ceriporiopsis subvermispora*, *Chrysosporium inops*, *Chrysosporium keratinophilum*, *Chrysosporium lucknowense*, *Chrysosporium merdarium*, *Chrysosporium pannicola*, *Chrysosporium queenslandicum*, *Chrysosporium tropicum*, *Chrysosporium zonatum*, *Coprinus cinereus*, *Coriolus hirsutus*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola insolens*, *Humicola lanuginosa*, *Mucor miehei*, *Myceliophthora thermophila*, *Neurospora crassa*, *Penicillium purpurogenum*, *Phanerochaete chrysosporium*, *Phlebia radiata*, *Pleurotus eryngii*, *Thielavia terrestris*, *Trametes villosa*, *Trametes versicolor*, *Trichoderma harzianum*, *Trichoderma koningii*, *Trichoderma longibrachiatum*, *Trichoderma reesei*, or *Trichoderma viride* cell.

Methods of Production

The present invention also relates to methods of producing a variant, comprising: (a) cultivating a host cell of the present invention under conditions suitable for expression of the variant; and (b) recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be recovered using methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure variants.

In an alternative aspect, the variant is not recovered, but rather a host cell of the present invention expressing the variant is used as a source of the variant.

Compositions

The present invention also relates to compositions comprising a glucoamylase variant of the present invention. Preferably the composition also comprises a carrier and/or an excipient. More preferably, the compositions are enriched in such a polypeptide. The term "enriched" indicates that the glucoamylase activity of the composition has been increased, e.g., with an enrichment factor of at least 1.1. Preferably, the compositions are formulated to provide desirable characteristics such as low color, low odor and acceptable storage stability.

The composition may comprise a glucoamylase variant of the present invention as the major enzymatic component, e.g., a mono-component composition. Alternatively, the composition may comprise multiple enzymatic activities, such as an aminopeptidase, alpha-amylase, isoamylase carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, pullulanase, proteolytic enzyme, ribonuclease, transglutaminase, or xylanase.

In a particular embodiment, the composition comprises an alpha-amylase and the glucoamylase variant according to the invention. In another embodiment, the composition comprises an isoamylase and the glucoamylase variant according to the invention. In another embodiment the composition comprises an alpha-amylase, an isoamylase and the glucoamylase variant according to the invention.

In another aspect, the composition comprises the glucoamylase variant of the invention combined with a pullulanase. In another aspect the composition comprises the glucoamylase variant of the invention combined with a pullulanase, and an isoamylase. In another aspect the composition comprises the glucoamylase variant of the invention combined with a pullulanase, and an alpha-amylase.

In a particular embodiment, the composition further comprises a protease.

In addition to a glucoamylase variant according to the invention the composition may further comprise an alpha-amylase. Particularly the alpha-amylase is an acid fungal alpha-amylase. A fungal acid stable alpha-amylase is an alpha-amylase that has activity in the pH range of 3.0 to 7.0 and preferably in the pH range from 3.5 to 6.5, including activity at a pH of about 4.0, 4.5, 5.0, 5.5, and 6.0.

Preferably the acid fungal alpha-amylase is derived from the genus Aspergillus, especially a strain of A. terreus, A. niger, A. oryzae, A. awamori, A. fumigatus, or Aspergillus kawachii, or from the genus Rhizomucor, preferably a strain the Rhizomucor pusillus, or the genus Meripilus, preferably a strain of Meripilus giganteus.

In a preferred embodiment the alpha-amylase is derived from a strain of the genus Rhizomucor, preferably a strain the Rhizomucor pusillus, such as one shown in SEQ ID NO: 3 in WO 2013/006756, such as a Rhizomucor pusillus alpha-amylase hybrid having an Aspergillus niger linker and starch-binding domain, such as the one shown in SEQ ID NO: 5 herein, or a variant thereof.

In an embodiment, the alpha-amylase is selected from the group consisting of:

(i) an alpha-amylase comprising the polypeptide of SEQ ID NO: 5;

(ii) an alpha-amylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 5.

In an embodiment, the alpha-amylase is a variant of the alpha-amylase shown in SEQ ID NO: 5 having at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R+V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C (using SEQ ID NO: 5 for numbering).

In an embodiment, the alpha-amylase is derived from a Rhizomucor pusillus with an Aspergillus niger glucoamylase linker and starch-binding domain (SBD), preferably disclosed as SEQ ID NO: 5, preferably having one or more of the following substitutions: G128D, D143N, preferably G128D+D143N (using SEQ ID NO: 5 for numbering), and wherein the alpha-amylase variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the polypeptide of SEQ ID NO: 5.

In an embodiment, the ratio between glucoamylase and alpha-amylase present and/or added during saccharification and/or fermentation may preferably be in the range from 500:1 to 1:1, such as from 250:1 to 1:1, such as from 100:1 to 1:1, such as from 100:2 to 100:50, such as from 100:3 to 100:70.

The polypeptide compositions may be prepared in accordance with methods known in the art and may be in the form of a liquid or a dry composition. For instance, the polypeptide composition may be in the form of a granulate or a micro-granulate. The polypeptide to be included in the composition may be stabilized in accordance with methods known in the art.

Examples are given below of preferred uses of the polypeptide or polypeptide compositions of the invention. The dosage of the polypeptide composition of the invention and other conditions under which the composition is used may be determined on the basis of methods known in the art.

The above compositions are suitable for use in liquefaction, saccharification, and/or fermentation processes, preferably in starch conversion, especially for producing syrup and fermentation products, such as ethanol.

Examples are given below of preferred uses of the polypeptide compositions of the present invention. The dosage of the polypeptide composition of the invention and other conditions under which the composition is used may be determined on the basis of methods known in the art.

Methods of Using the Glucoamylase Variant of the Invention—Industrial Applications The glucoamylase variants of the present invention possess valuable properties allowing for a variety of industrial applications. In particular, the glucoamylase variants may be used in ethanol production, and starch conversion processes.

The glucoamylase variants may be used for starch processes, in particular, starch conversion. Also contemplated are compositions for starch conversion purposes, which may beside the glucoamylase of the invention also comprise an alpha-amylase, a pullulanase and/or a protease.

Further, the glucoamylases of the invention are particularly useful in the production of sweeteners and ethanol (see, e.g., U.S. Pat. No. 5,231,017, which is hereby incorporated by reference), such as fuel, drinking and industrial ethanol, from starch or whole grains.

In one embodiment the present invention relates to a use of the glucoamylase according to the invention for production of a syrup and/or a fermentation product from a starch containing material. The starch material may in one embodiment be gelatinized. In another embodiment, the starch material is ungelatinized.

Starch Processing

Native starch consists of microscopic granules, which are insoluble in water at room temperature. When aqueous starch slurry is heated, the granules swell and eventually burst, dispersing the starch molecules into the solution. At temperatures up to about 50° C. to 75° C. the swelling may be reversible. However, with higher temperatures an irreversible swelling called "gelatinization" begins. During this "gelatinization" process there is a dramatic increase in viscosity. Granular starch to be processed may be a highly refined starch quality, preferably at least 90%, at least 95%, at least 97% or at least 99.5% pure or it may be a more crude starch-containing materials comprising (e.g., milled) whole grains including non-starch fractions such as germ residues and fibers. The raw material, such as whole grains, may be reduced in particle size, e.g., by milling, in order to open up the structure and allowing for further processing. In dry milling whole kernels are milled and used. Wet milling gives a good separation of germ and meal (starch granules and protein) and is often applied at locations where the starch hydrolyzate is used in the production of, e.g., syrups. Both dry and wet milling is well known in the art of starch processing and may be used in a process of the invention. Methods for reducing the particle size of the starch containing material are well known to those skilled in the art.

As the solids level is 30-40% in a typical industrial process, the starch has to be thinned or "liquefied" so that it can be suitably processed. This reduction in viscosity is primarily attained by enzymatic degradation in current commercial practice.

Liquefaction is carried out in the presence of an alpha-amylase, preferably a bacterial alpha-amylase and/or acid fungal alpha-amylase. In an embodiment, a phytase is also present during liquefaction. In an embodiment, viscosity reducing enzymes such as a xylanase and/or beta-glucanase is also present during liquefaction.

During liquefaction, the long-chained starch is degraded into branched and linear shorter units (maltodextrins) by an alpha-amylase. Liquefaction may be carried out as a three-step hot slurry process. The slurry is heated to between 60-95° C. (e.g., 70-90° C., such as 77-86° C., 80-85° C., 83-85° C.) and an alpha-amylase is added to initiate liquefaction (thinning).

The slurry may in an embodiment be jet-cooked at between 95-140° C., e.g., 105-125° C., for about 1-15 minutes, e.g., about 3-10 minutes, especially around 5 minutes. The slurry is then cooled to 60-95° C. and more alpha-amylase is added to obtain final hydrolysis (secondary liquefaction). The jet-cooking process is carried out at pH 4.5-6.5, typically at a pH between 5 and 6. The alpha-amylase may be added as a single dose, e.g., before jet cooking.

The liquefaction process is carried out at between 70-95° C., such as 80-90° C., such as around 85° C., for about 10 minutes to 5 hours, typically for 1-2 hours. The pH is between 4 and 7, such as between 5.5 and 6.2. In order to ensure optimal enzyme stability under these conditions, calcium may optionally be added (to provide 1-60 ppm free calcium ions, such as about 40 ppm free calcium ions). After such treatment, the liquefied starch will typically have a "dextrose equivalent" (DE) of 10-15.

Generally, liquefaction and liquefaction conditions are well known in the art.

Saccharification may be carried out using conditions well-known in the art with a carbohydrate-source generating enzyme, in particular a glucoamylase, or a beta-amylase and optionally a debranching enzyme, such as an isoamylase or a pullulanase. For instance, a full saccharification step may last from about 24 to about 72 hours. However, it is common to do a pre-saccharification of typically 40-90 minutes at a temperature between 30-65° C., typically about 60° C., followed by complete saccharification during fermentation in a simultaneous saccharification and fermentation (SSF) process. Saccharification is typically carried out at a temperature in the range of 20-75° C., e.g., 25-65° C. and 40-70° C., typically around 60° C., and at a pH between about 4 and 5, normally at about pH 4.5.

The saccharification and fermentation steps may be carried out either sequentially or simultaneously. In an embodiment, saccharification and fermentation are performed simultaneously (referred to as "SSF"). However, it is common to perform a pre-saccharification step for about 30 minutes to 2 hours (e.g., 30 to 90 minutes) at a temperature of 30 to 65° C., typically around 60° C. which is followed by a complete saccharification during fermentation referred to as simultaneous saccharification and fermentation (SSF). The pH is usually between 4.2-4.8, e.g., pH 4.5. In a simultaneous saccharification and fermentation (SSF) process, there is no holding stage for saccharification, rather, the yeast and enzymes are added together.

In a typical saccharification process, maltodextrins produced during liquefaction are converted into dextrose by adding a glucoamylase and optionally a debranching enzyme, such as an isoamylase (U.S. Pat. No. 4,335,208) or a pullulanase. The temperature is lowered to 60° C., prior to the addition of the glucoamylase and debranching enzyme. The saccharification process proceeds for 24-72 hours. Prior to addition of the saccharifying enzymes, the pH is reduced to below 4.5, while maintaining a high temperature (above 95° C.), to inactivate the liquefying alpha-amylase. This process reduces the formation of short oligosaccharide called "panose precursors," which cannot be hydrolyzed properly by the debranching enzyme. Normally, about 0.2-0.5% of the saccharification product is the branched trisaccharide panose (Glc p$\alpha$1-6Glc p$\alpha$1-4Glc), which cannot be degraded by a pullulanase. If active amylase from the liquefaction remains present during saccharification (i.e., no denaturing), the amount of panose can be as high as 1-2%, which is highly undesirable since it lowers the saccharification yield significantly.

Other fermentation products may be fermented at conditions and temperatures well known to persons skilled in the art, suitable for the fermenting organism in question.

The fermentation product may be recovered by methods well known in the art, e.g., by distillation.

In a particular embodiment, the process of the invention further comprises, prior to the conversion of a starch-containing material to sugars/dextrins the steps of:

(x) reducing the particle size of the starch-containing material; and (y) forming a slurry comprising the starch-containing material and water.

In an embodiment, the starch-containing material is milled to reduce the particle size. In an embodiment the particle size is reduced to between 0.05-3.0 mm, preferably 0.1-0.5 mm, or so that at least 30%, preferably at least 50%, more preferably at least 70%, even more preferably at least 90% of the starch-containing material fits through a sieve with a 0.05-3.0 mm screen, preferably 0.1-0.5 mm screen.

The aqueous slurry may contain from 10-55 wt. % dry solids (DS), preferably 25-45 wt. % dry solids (DS), more preferably 30-40 wt. % dry solids (DS) of starch-containing material.

Conventional starch-conversion processes, such as liquefaction and saccharification processes are described, e.g., in U.S. Pat. No. 3,912,590, EP 252730 and EP 063909, which are incorporated herein by reference.

In an embodiment, the conversion process degrading starch to lower molecular weight carbohydrate components such as sugars or fat replacers includes a debranching step.

In the case of converting starch into a sugar, the starch is depolymerized. Such a depolymerization process consists of, e.g., a pre-treatment step and two or three consecutive process steps, i.e., a liquefaction process, a saccharification process, and depending on the desired end-product, an optional isomerization process.

When the desired final sugar product is, e.g., high fructose syrup the dextrose syrup may be converted into fructose. After the saccharification process, the pH is increased to a value in the range of 6-8, e.g., pH 7.5, and the calcium is removed by ion exchange. The dextrose syrup is then converted into high fructose syrup using, e.g., an immobilized glucose isomerase.

Production of Fermentation Products

Fermentable sugars (e.g., dextrins, monosaccharides, particularly glucose) are produced from enzymatic saccharification. These fermentable sugars may be further purified and/or converted to useful sugar products. In addition, the sugars may be used as a fermentation feedstock in a microbial fermentation process for producing end-products, such as alcohol (e.g., ethanol, and butanol), organic acids (e.g., succinic acid, 3-HP and lactic acid), sugar alcohols (e.g., glycerol), ascorbic acid intermediates (e.g., gluconate, 2-keto-D-gluconate, 2,5-diketo-D-gluconate, and 2-keto-L-gulonic acid), amino acids (e.g., lysine), proteins (e.g., antibodies and fragment thereof).

In an embodiment, the fermentable sugars obtained during the liquefaction process steps are used to produce alcohol and particularly ethanol. In ethanol production, an SSF process is commonly used wherein the saccharifying enzymes and fermenting organisms (e.g., yeast) are added together and then carried out at a temperature of 30-40° C.

The organism used in fermentation will depend on the desired end-product. Typically, if ethanol is the desired end product yeast will be used as the fermenting organism. In some preferred embodiments, the ethanol-producing microorganism is a yeast and specifically *Saccharomyces* such as strains of *S. cerevisiae* (U.S. Pat. No. 4,316,956). A variety of *S. cerevisiae* are commercially available and these include but are not limited to FALI (Fleischmann's Yeast), SUPERSTART (Alltech), FERMIOL (DSM Specialties), RED STAR (Lesaffre) and Angel alcohol yeast (Angel Yeast Company, China). The amount of starter yeast employed in the methods is an amount effective to produce a commercially significant amount of ethanol in a suitable amount of time, (e.g., to produce at least 10% ethanol from a substrate having between 25-40% DS in less than 72 hours). Yeast cells are generally supplied in amounts of about $10^4$ to about $10^{12}$, and preferably from about $10^7$ to about $10^{10}$ viable yeast count per mL of fermentation broth. After yeast is added to the mash, it is typically subjected to fermentation for about 24-96 hours, e.g., 35-60 hours. The temperature is between about 26-34° C., typically at about 32° C., and the pH is from pH 3-6, e.g., around pH 4-5.

The fermentation may include, in addition to a fermenting microorganisms (e.g., yeast), nutrients, and additional enzymes, including phytases. The use of yeast in fermentation is well known in the art.

In further embodiments, use of appropriate fermenting microorganisms, as is known in the art, can result in fermentation end product including, e.g., glycerol, 1,3-propanediol, gluconate, 2-keto-D-gluconate, 2,5-diketo-D-gluconate, 2-keto-L-gulonic acid, succinic acid, lactic acid, amino acids, and derivatives thereof. More specifically when lactic acid is the desired end product, a *Lactobacillus* sp. (*L. casei*) may be used; when glycerol or 1,3-propanediol are the desired end-products *E. coli* may be used; and when 2-keto-D-gluconate, 2,5-diketo-D-gluconate, and 2-keto-L-gulonic acid are the desired end products, *Pantoea citrea* may be used as the fermenting microorganism. The above enumerated list are only examples and one skilled in the art will be aware of a number of fermenting microorganisms that may be used to obtain a desired end product.

Processes for Producing Fermentation Products from Ungelatinized Starch-Containing Material The invention relates to processes for producing fermentation products from starch-containing material without gelatinization (i.e., without cooking) of the starch-containing material (often referred to as a "raw starch hydrolysis" process). The fermentation product, such as ethanol, can be produced without liquefying the aqueous slurry containing the starch-containing material and water. In one embodiment a process of the invention includes saccharifying (e.g., milled) starch-containing material, e.g., granular starch, below the initial gelatinization temperature, preferably in the presence of alpha-amylase and/or carbohydrate-source generating enzyme(s), e.g., a glucoamylase, to produce sugars that can be fermented into the fermentation product by a suitable fermenting organism. In this embodiment, the desired fermentation product, e.g., ethanol, is produced from ungelatinized (i.e., uncooked), preferably milled, cereal grains, such as corn.

Accordingly, in one aspect the invention relates to processes for producing fermentation products from starch-containing material comprising simultaneously saccharifying and fermenting starch-containing material using a carbohydrate-source generating enzyme and a fermenting organism at a temperature below the initial gelatinization temperature of said starch-containing material. Saccharification and fermentation may also be separate. Thus, in another aspect the invention relates to processes of producing fermentation products, comprising the following steps:

(i) saccharifying a starch-containing material at a temperature below the initial gelatinization temperature; and (ii) fermenting using a fermentation organism;

wherein step (i) is carried out using at least a glucoamylase variant of the invention.

In one embodiment, an alpha amylase is added in step (i). In another embodiment steps (i) and (ii) are performed simultaneously.

In a preferred embodiment, the fermentation product is ethanol and the fermenting organism is a yeast, particularly a *Saccharomyces* sp. more particularly a *Saccharomyces cerevisiae*. The *Saccharomyces cerevisiae* may in one further embodiment express a glucoamylase, preferably a *Gloeophyllum* sp. glucoamylase, more preferably a glucoamylase from *Gloeophyllum sepiarium*, or *Gloeophyllum trabeum*, most preferably the glucoamylase disclosed as SEQ ID NO: 2 or SEQ ID NO: 4 herein. In a particular embodiment a variant glucoamylase of the invention, particularly GSA202 is added/present during saccharification and the *Saccharomyces cerevisiae* is expressing the glucoamylase disclosed in SEQ ID NO: 2 or a glucoamylase having at least 90% identity to SEQ ID NO: 2.

In one embodiment, a protease is also present. The protease may be any acid fungal protease or metalloprotease. The fermentation product, e.g., ethanol, may optionally be recovered after fermentation, e.g., by distillation. Typically, amylase(s), such as glucoamylase(s) and/or other carbohydrate-source generating enzymes, and/or alpha-amylase(s), is(are) present during fermentation. Examples of glucoamylases and other carbohydrate-source generating enzymes include raw starch hydrolyzing glucoamylases. Examples of alpha-amylase(s) include acid alpha-amylases such as acid fungal alpha-amylases. Examples of fermenting organisms include yeast, e.g., a strain of *Saccharomyces cerevisiae*. In a preferred embodiment the yeast is expressing the glucoamylase variant of the invention. The term "initial gelatinization temperature" means the lowest temperature at which starch gelatinization commences. In general, starch heated in water begins to gelatinize between about 50° C. and 75° C.; the exact temperature of gelatinization depends on the specific starch and can readily be determined by the skilled artisan. Thus, the initial gelatinization temperature may vary according to the plant species, to the particular variety of the plant species as well as with the growth conditions. In the context of this invention the initial gelatinization temperature of a given starch-containing material may be determined as the temperature at which birefringence is lost in 5% of the starch granules using the method described by Gorinstein and Lii, 1992, *Starch/Stärke* 44(12): 461-466. Before initiating the process a slurry of starch-containing material, such as granular starch, having 10-55 w/w % dry solids (DS), preferably 25-45 w/w % dry solids, more preferably 30-40 w/w % dry solids of starch-containing material may be prepared. The slurry may include water and/or process waters, such as stillage (backset), scrubber water, evaporator condensate or distillate, side-stripper water from distillation, or process water from other fermentation product plants. Because the process of the invention is carried out below the initial gelatinization temperature, and thus no significant viscosity increase takes place, high levels of stillage may be used if desired. In an embodiment, the aqueous slurry contains from about 1 to about 70 vol. %, preferably 15-60 vol. %, especially from about 30 to 50 vol. % water and/or process waters, such as stillage (backset), scrubber water, evaporator condensate or distillate, side-stripper water from distillation, or process water from other fermentation product plants, or combinations thereof, or the like. The starch-containing material may be prepared by reducing the particle size, preferably by dry or wet milling, to 0.05 to 3.0 mm, preferably 0.1-0.5 mm. After being subjected to a process of the invention at least 85%, at least 86%, at least 87%, at least 88%, at least 89%, at least 90%, at least 91%, at least 92%, at least 93%, at least 94%, at least 95%, at least 96%, at least 97%, at least 98%, or preferably at least 99% of the dry solids in the starch-containing material are converted into a soluble starch hydrolyzate. A process in this aspect of the invention is conducted at a temperature below the initial gelatinization temperature, which means that the temperature typically lies in the range between 30-75° C., preferably between 45-60° C. In one embodiment, the process carried at a temperature from 25° C. to 40° C., such as from 28° C. to 35° C., such as from 30° C. to 34° C., preferably around 32° C. In an embodiment, the process is carried out so that the sugar level, such as glucose level, is kept at a low level, such as below 6 w/w %, such as below about 3 w/w %, such as below about 2 w/w %, such as below about 1 w/w %, such as below about 0.5 w/w %, or below 0.25 w/w %, such as below about 0.1 w/w %. Such low levels of sugar can be accomplished by simply employing adjusted quantities of enzyme and fermenting organism. A skilled person in the art can easily determine which doses/quantities of enzyme and fermenting organism to use. The employed quantities of enzyme and fermenting organism may also be selected to maintain low concentrations of maltose in the fermentation broth. For instance, the maltose level may be kept below about 0.5 w/w %, such as below about 0.2 w/w %. The process of the invention may be carried out at a pH from about 3 and 7, preferably from pH 3.5 to 6, or more preferably from pH 4 to 5. In an embodiment fermentation is ongoing for 6 to 120 hours, in particular, 24 to 96 hours.

Processes for Producing Fermentation Products from Gelatinized Starch-Containing Material In this aspect, the invention relates to processes for producing fermentation products, especially ethanol, from starch-containing material, which process includes a liquefaction step and sequentially or simultaneously performed saccharification and fermentation steps. Consequently, the invention relates to processes for producing fermentation products from starch-containing material comprising the steps of:

(a) liquefying starch-containing material in the presence of an alpha-amylase;

(b) saccharifying the liquefied material obtained in step (a);

(c) fermenting using a fermenting organism;

wherein step (b) is carried out in the presence of a glucoamylase according to the invention.

In a preferred embodiment, the fermentation product is ethanol and the fermenting organism is a yeast, particularly a *Saccharomyces* sp. more particularly a *Saccharomyces cerevisiae*. The *Saccharomyces cerevisiae* may in one further embodiment express a glucoamylase, preferably a *Gloeophyllum* sp. glucoamylase, more preferably a glucoamylase from *Gloeophyllum sepiarium*, or *Gloeophyllum trabeum*, most preferably the glucoamylase disclosed as SEQ ID NO: 2 or SEQ ID NO: 4 herein. In a particular embodiment a variant glucoamylase of the invention, particularly GSA202 is added/present during saccharification and the *Saccharomyces cerevisiae* is expressing the glucoamylase disclosed in SEQ ID NO: 2 or a glucoamylase having at least 90% identity to SEQ ID NO: 2.

In an embodiment, a protease, such as an acid fungal protease or a metallo protease is added before, during and/or after liquefaction. In an embodiment, the metalloprotease is derived from a strain of *Thermoascus*, e.g., a strain of *Thermoascus aurantiacus*, especially *Thermoascus aurantiacus* CGMCC No. 0670. In another embodiment, the protease is a bacterial protease, particularly a protease derived from a strain of *Pyrococcus*, more particularly from *Pyrococcus furiosus* disclosed in U.S. Pat. No. 6,358,726.

A further glucoamylase may be added. In an embodiment the further glucoamylase derived from a strain of *Aspergillus*, e.g., *Aspergillus niger* or *Aspergillus awamori*, a strain of *Talaromyces*, especially *Talaromyces emersonii*; or a strain of *Athelia*, especially *Athelia rolfsii*; a strain of *Trametes*, e.g., *Trametes cingulata*; or a mixture thereof. Saccharification step (b) and fermentation step (c) may be carried out either sequentially or simultaneously. A pullulanase and/or protease may be added during saccharification and/or fermentation when the process is carried out as a sequential saccharification and fermentation process and before or during fermentation when steps (b) and (c) are carried out simultaneously (SSF process). The pullulanase and/or protease may also advantageously be added before liquefaction (pre-liquefaction treatment), i.e., before or during step (a), and/or after liquefaction (post liquefaction treatment), i.e., after step (a). The pullulanase is most advantageously added before or during liquefaction, i.e., before or during step (a). The fermentation product, such as especially ethanol, may optionally be recovered after fermentation, e.g., by distillation. The fermenting organism is preferably yeast, preferably a strain of *Saccharomyces cerevisiae*. In a preferred embodiment, the yeast is expressing the glucoamylase variant of the invention. In a particular embodiment, the process of the invention further comprises, prior to step (a), the steps of:

x) reducing the particle size of the starch-containing material, preferably by milling (e.g., using a hammer mill);

y) forming a slurry comprising the starch-containing material and water.

In an embodiment, the particle size is smaller than a #7 screen, e.g., a #6 screen. A #7 screen is usually used in conventional prior art processes. The aqueous slurry may contain from 10-55, e.g., 25-45 and 30-40, w/w % dry solids (DS) of starch-containing material. The slurry is heated to above the gelatinization temperature and an alpha-amylase variant may be added to initiate liquefaction (thinning). The slurry may in an embodiment be jet-cooked to further gelatinize the slurry before being subjected to alpha-amylase in step (a). Liquefaction may in an embodiment be carried out as a three-step hot slurry process. The slurry is heated to between 60-95° C., preferably between 70-90° C., such as preferably between 80-85° C. at pH 4-6, preferably 4.5-5.5, and alpha-amylase variant, optionally together with a pullulanase and/or protease, preferably metalloprotease, are added to initiate liquefaction (thinning). In an embodiment, the slurry may then be jet-cooked at a temperature between 95-140° C., preferably 100-135° C., such as 105-125° C., for about 1-15 minutes, preferably for about 3-10 minutes, especially around about 5 minutes. The slurry is cooled to 60-95° C. and more alpha-amylase and optionally pullulanase and/or protease, preferably metalloprotease, is(are) added to finalize hydrolysis (secondary liquefaction). The liquefaction process is usually carried out at pH 4.0-6, in particular, at a pH from 4.5 to 5.5. Saccharification step (b) may be carried out using conditions well known in the art. For instance, a full saccharification process may last up to from about 24 to about 72 hours, however, it is common only to do a pre-saccharification of typically 40-90 minutes at a temperature between 30-65° C., typically about 60° C., followed by complete saccharification during fermentation in a simultaneous saccharification and fermentation process (SSF process). Saccharification is typically carried out at temperatures from 20-75° C., preferably from 40-70° C., typically around 60° C., and at a pH between 4 and 5, normally at about pH 4.5. The most widely used process to produce a fermentation product, especially ethanol, is a simultaneous saccharification and fermentation (SSF) process, in which there is no holding stage for the saccharification, meaning that a fermenting organism, such as yeast, and enzyme(s), may be added together. SSF may typically be carried out at a temperature from 25° C. to 40° C., such as from 28° C. to 35° C., such as from 30° C. to 34° C., preferably around about 32° C. In an embodiment fermentation is ongoing for 6 to 120 hours, in particular, 24 to 96 hours.

Starch-Containing Materials

Any suitable starch-containing starting material may be used in a process of the present invention. The starting material is generally selected based on the desired fermentation product. Examples of starch-containing starting materials, suitable for use in the processes of the present invention, include barley, beans, cassava, cereals, corn, milo, peas, potatoes, rice, rye, sago, sorghum, sweet potatoes, tapioca, wheat, and whole grains, or any mixture thereof. The starch-containing material may also be a waxy or non-waxy type of corn and barley. In an embodiment, the starch-containing material is corn. In an embodiment, the starch-containing material is wheat.

Fermentation Products

The term "fermentation product" means a product produced by a method or process including fermenting using a fermenting organism. Fermentation products include alcohols (e.g., ethanol, methanol, butanol); organic acids (e.g., citric acid, acetic acid, itaconic acid, lactic acid, succinic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, $B_{12}$, beta-carotene); and hormones. In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. In an embodiment, the fermentation product is ethanol.

The invention is further disclosed in the following numbered paragraphs:

[1]. A glucoamylase variant, having increased raw starch hydrolytic activity at pH=4.0, T=32° C., compared to the glucoamylase disclosed in SEQ ID NO: 2, wherein the variant is derived from a glucoamylase having a catalytic domain comprising amino acids 1-454 of SEQ ID NO: 2 or 1-454 of SEQ ID NO: 4, a linker comprising amino acids 455-462 of SEQ ID NO: 2 or amino acids 455-465 of SEQ ID NO: 4 and a starch binding domain comprising amino acids 463-556 of SEQ ID NO: 2 or amino acids 466-559 of SEQ ID NO: 4, and wherein the variant further comprises a substitution at one or more positions selected from the group consisting of:

V18M+T43K+S95P+A121P+Q318Y+A518K+N527M+T549W;

V18M+T43K+S95P+T116R+A121P+Q318Y+N539R+I541Y+T543V+A545S+S546PCGV+G547S+S548T+T549A;

S95P+A121P+Y295W+T116R+N539R+I541Y+T543V+A545S+S546PCGV+G547S+S548T+T549A;

T43K+S95P+A121P+Y295W+Q318Y+N539R+I541Y+T543V+A545S+S546PCGV+G547S+S548T+T549A;

T43K+S95P+G120S+A121P+Y295W+Q318Y+N539R+ I541Y+T543V+A545S+S546GCGV+G547S+S548T+ T549A;
V18M+T43K+S95P+T116R+A121P+Q318Y+ S458SCGG+N527M+T(V)549W;
V18M+T43K+S95P+A121P+Q318Y+S458SCGG+ N527M+T(V)549W+N503R;
V18M+T43K+S95P+A121P+Q318Y+N539R+I541Y+ T543V+A545S+S546PCGV+G547S+S548T+T549A;
T43K+Q318Y+S95P+A121P+Y295W+S458SCGG+ N527M+T(V)549W;
S95P+A121P+Y295W+G120S+N539R+I541Y+T543V+A545S+S546PCGV+G547S+S548T+T549A;
V18M+T43K+S95P+A121P+Q318Y+S458SCGG+N527M T(V)549W;
S95P+A121P+Y295W+N539R+I541Y+T543V+A545S+S546PCGV+G547S+S548T+T549A;
T43K+S95P+A121P+Y295W+Q318Y+N539R+I541Y+T543V+A545S+S546GCGV+G547S+S548T+T549A;
S95P+T116R+A121P+Y295W+N539R+I541Y+T543V+A545S+S546GCGV+G547S+S548T+T549A;
T43K+S95P+A121P+Y295W+Q318Y+N527M+T(V)549W+N503R;
S95P+A121P+Y295W+N539R+I541Y+T543V+A545S+S546GCGV+G547S+S548T+T549A;
V18M+T43K+S95P+A121P+A518K+N527M+T549W;
T43K+S95P+G120S+A121P+Y295W+Q318Y+A518K+N527M+T(V)549W;
T43K+S95P+A121P+Q318Y+A493V+A518K+N527M+T549W;
S95P+G120S+A121P+Y295W+N539R+I541Y+T543V+A545S+S546GCGV+G547S+S548T+T549A;
V18M+T43K+S95P+A121P+Y295W+A518K+N527M+T549W;
T43K+S95P+A121P+Y295W+Q318Y+N527M+T(V)549W;
T43K+S95P+A121P+Q318Y+N527M+T549W;
V18M+T43K+S95P+A121P+Q318Y+N527M+T549W;
S95P+A121P+Y295W+T116R+N527M+T(V)549W;
V18M+T43K+S95P+T116R+A121P+Q318Y+A493V+N527M+T549W;
V18M+T43K+S95P+A121P+Q318Y+A493V+N527M+T549W;
T43K+S95P+A121P+Y295W+Q318Y+A518K+N527M+T(V)549W;
S95P+A121P+Y295W+A117Q+N527M+T(V)549W;
V18M+T43K+S95P+A121P+Q318Y+A493V+A518K+N527M+T549W;
T43K+S95P+A121P+Q318Y+A518K+N527M+T549W;
V18M+T43K+S95P+T116R+A121P+Q318Y+N527M+T549W;
T43K+S95P+A121P+Q318Y+A493V+N527M+T549W;
S95P+T116R+A121P+Y295W+A518K+N527M+T(V)549W;
V18M+T43K+S95P+A121P+Q318Y+A518K+T(V)549W;
T43K+S95P+A121P+Y295W+Q318Y+A518K+N527M+T549W;
V18M+T43K+S95P+T116R+A121P+Q318Y+A518K+T549W;
S95P+A121P+Y295W+Q318Y+N527M+T(V)549W;
S95P+G120S+A121P+Y295W+N527M+T(V)549W;
S95P+A121P+Y295W+A518K+N527M+T(V)549W;
S95P+A121P+Y295W+N527M+T(V)549W;
S95P+N112L+A121P+Y295W+N527M+T(V)549W;
S95P+A121P+Y295W+N527M+T(V)549W;
V18M+T43K+S95P+A121P+Q318Y+A518K+N527M+T549W;
T43K+S95P+A121P+Y295W+Q318Y+N527M+T549W;
S95P+G120S+A121P+Y295W+A518K+N527M+T(V)549W;
S95P+N112L+A121P+Y295W+A518K+N527M+T(V)549W;
V18M+T43K+S95P+A121P+Q318Y+A518K+T549W;
S95P+A121P+Y295W+A493V+A518K+E520Q+T549W;
S95P+A121P+Y295W+A518K+N527M+T549W;
S95P+A121P+Y295W+A518K+T(V)549W;
S95P+A121P+Y295W+A518K+N527M;
S95P+A121P+Y295W+S458C+N539R+I541Y+T543V+A545S+S546GCGV+G547S+S548T+T549A;
S95P+A121P+Y295W+N527M+T549W;
S95P+A121P+A271F+Y295W+A518K+N527M+T549W;
S95P+A121P+Y295W+A493V;
S95P+A121P+Y295W+S540K;
S95P+A121P+Y295W+S540R;
S95P+A121P+Y295W+A518K+N527M;
S95P+A121P+Y295W+S458SGGC+N539R+I541Y+T543V+A545S+S546GCGV+G547S+S548T+T549A;
T43K+S95P+A121P+Y295W+N527M+T(V)549W;
S95P+A121P+Y295W+S458SCGG+N539R+I541Y+T543V+A545S+S546GCGV+G547S+S548T+T549A;

wherein the position numbering corresponds to amino acid positions in the amino acid sequence set forth in SEQ ID NO: 2; and wherein the variants have at least 85%, at least 90%, at least 95% identity, at least 96%, at least 97%, at least 98%, or at least 99%, but less than 100%, sequence identity to the amino acid sequence of SEQ ID NO: 2.

[2]. The glucoamylase variant of paragraph 1, wherein the variant is derived from a glucoamylase having a catalytic domain comprising amino acids 1-454 of SEQ ID NO: 2, a linker comprising amino acids 455-465 of SEQ ID NO: 4 and a starch binding domain comprising amino acids 466-559 of SEQ ID NO: 4, and wherein the variant comprises a combination of specific substitutions selected from the group consisting of:

V18M+T43K+S95P+T116R+A121P+Q318Y+N539R+I541Y+T543V+A545S+S546PCGV+G547S+S548T+T549A;
S95P+A121P+Y295W+T116R+N539R+I541Y+T543V+A545S+S546PCGV+G547S+S548T+T549A;
T43K+S95P+A121P+Y295W+Q318Y+N539R+I541Y+T543V+A545S+S546PCGV+G547S+S548T+T549A;
T43K+S95P+G120S+A121P+Y295W+Q318Y+N539R+I541Y+T543V+A545S+S546GCGV+G547S+S548T+T549A;
V18M+T43K+S95P+T116R+A121P+Q318Y+S458SCGG+N527M+T(V)549W;
V18M+T43K+S95P+A121P+Q318Y+S458SCGG+N527M+T(V)549W+N503R;
V18M+T43K+S95P+A121P+Q318Y+N539R+I541Y+T543V+A545S+S546PCGV+G547S+S548T+T549A;
T43K+S95P+A121P+Y295W+Q318Y+S458SCGG+N527M+T(V)549W;
S95P+A121P+Y295W+G120S+N539R+I541Y+T543V+A545S+S546PCGV+G547S+S548T+T549A;
V18M+T43K+S95P+A121P+Q318Y+S458SCGG+N527M T(V)549W;
S95P+A121P+Y295W+N539R+I541Y+T543V+A545S+S546PCGV+G547S+S548T+T549A;
T43K+S95P+A121P+Y295W+Q318Y+N539R+I541Y+T543V+A545S+S546GCGV+G547S+S548T+T549A;
S95P+T116R+A121P+Y295W+N539R+I541Y+T543V+A545S+S546GCGV+G547S+S548T+T549A;
T43K+S95P+A121P+Y295W+Q318Y+N527M+T(V)549W+N503R;

S95P+A121P+Y295W+N539R+I541Y+T543V+A545S+
S546GCGV+G547S+S548T+T549A;
and wherein the increase in raw starch hydrolytic activity
compared to SEQ ID NO: 2 is at least 30%, at least 35%,
such as at least 40%.

[3]. The glucoamylase variant of paragraph 2, further comprising the substitutions G456S+P461S+E472Q+L481I+
E489S+A493P+E520Q.

[4]. The glucoamylase variant of paragraph 1, wherein the
variant is derived from the glucoamylase of SEQ ID NO: 2,
and wherein the variant comprises a combination of specific
substitutions selected from the group consisting of:
V18M+T43K+S95P+A121P+Q318Y+A518K+N527M+
T549W;
V18M+T43K+S95P+A121P+A518K+N527M+T549W;
T43K+S95P+A121P+Q318Y+A493V+A518K+N527M+
T549W;
V18M+T43K+S95P+A121P+Y295W+A518K+N527M+
T549W;
T43K+S95P+A121P+Q318Y+N527M+T549W;
V18M+T43K+S95P+A121P+Q318Y+N527M+T549W;
V18M+T43K+S95P+T116R+A121P+Q318Y+A493V+
N527M+T549W;
V18M+T43K+S95P+A121P+Q318Y+A493V+N527M+
T549W;
V18M+T43K+S95P+A121P+Q318Y+A493V+A518K+
N527M+T549W;
T43K+S95P+A121P+Q318Y+A518K+N527M+T549W;
V18M+T43K+S95P+T116R+A121P+Q318Y+N527M+
T549W;
T43K+S95P+A121P+Q318Y+A493V+N527M+T549W;
T43K+S95P+A121P+Y295W+Q318Y+A518K+N527M+
T549W;
V18M+T43K+S95P+T116R+A121P+Q318Y+A518K+
T549W;
V18M+T43K+S95P+A121P+Q318Y+A518K+N527M+
T549W;
T43K+S95P+A121P+Y295W+Q318Y+N527M+T549W;
V18M+T43K+S95P+A121P+Q318Y+A518K+T549W;
S95P+A121P+Y295W+A493V+A518K+E520Q+T549W;
S95P+A121P+Y295W+A518K+N527M+T549W;
S95P+A121P+Y295W+N527M+T549W;
S95P+A121P+A271F+Y295W+A518K+N527M+T549W;
S95P+A121P+Y295W+A493V;
S95P+A121P+Y295W+S540K;
S95P+A121P+Y295W+S540R;
S95P+A121P+Y295W+A518K+N527M;
and wherein the increase in raw starch hydrolytic activity
compared to SEQ ID NO: 2 is at least 5%.

[5]. The glucoamylase variant of paragraph 4, wherein the
variant comprises a combination of specific substitutions
selected from the group consisting of:
V18M+T43K+S95P+A121P+A518K+N527M+T549W;
T43K+S95P+A121P+Q318Y+A493V+A518K+N527M+
T549W;
V18M+T43K+S95P+A121P+Y295W+A518K+N527M+
T549W;
T43K+S95P+A121P+Q318Y+N527M+T549W;
V18M+T43K+S95P+A121P+Q318Y+N527M+T549W;
V18M+T43K+S95P+T116R+A121P+Q318Y+A493V+
N527M+T549W;
V18M+T43K+S95P+A121P+Q318Y+A493V+N527M+
T549W;
V18M+T43K+S95P+A121P+Q318Y+A493V+A518K+
N527M+T549W;
T43K+S95P+A121P+Q318Y+A518K+N527M+T549W;
V18M+T43K+S95P+T116R+A121P+Q318Y+N527M+
T549W;
T43K+S95P+A121P+Q318Y+A493V+N527M+T549W;
T43K+S95P+A121P+Y295W+Q318Y+A518K+N527M+
T549W;
V18M+T43K+S95P+T116R+A121P+Q318Y+A518K+
T549W;
V18M+T43K+S95P+A121P+Q318Y+A518K+N527M+
T549W;
T43K+S95P+A121P+Y295W+Q318Y+N527M+T549W;
V18M+T43K+S95P+A121P+Q318Y+A518K+T549W;
S95P+A121P+Y295W+A493V+A518K+E520Q+T549W;
S95P+A121P+Y295W+A518K+N527M+T549W;
and wherein the increase in raw starch hydrolytic activity
compared to SEQ ID NO: 2 is at least 20%.

[6]. The glucoamylase variant of paragraph 1, wherein the
variant is derived from a glucoamylase having a catalytic
domain comprising amino acids 1-454 of SEQ ID NO: 2, a
linker comprising amino acids 455-465 of SEQ ID NO: 4
and a starch binding domain comprising amino acids 466-
559 of SEQ ID NO: 4, and wherein the variant comprises a
substitution at one or more positions selected from the group
consisting of:
T43K+S95P+G120S+A121P+Y295W+Q318Y+A518K+
N527M+T(V)549W;
S95P+G120S+A121P+Y295W+N539R+I541Y+T543V+
A545S+S546GCGV+G547S+S548T+T549A;
T43K+S95P+A121P+Y295W+Q318Y+N527M+T(V)
549W;
S95P+A121P+Y295W+T116R+N527M+T(V)549W;
T43K+S95P+A121P+Y295W+Q318Y+A518K+N527M+T
(V)549W;
S95P+A121P+Y295W+A117Q+N527M+T(V)549W;
S95P+T116R+A121P+Y295W+A518K+N527M+T(V)
549W;
V18M+T43K+S95P+A121P+Q318Y+A518K+T(V)549W;
S95P+A121P+Y295W+Q318Y+N527M+T(V)549W;
S95P+G120S+A121P+Y295W+N527M+T(V)549W;
S95P+A121P+Y295W+A518K+N527M+T(V)549W;
S95P+N112L+A121P+Y295W+N527M+T(V)549W;
S95P+A121P+Y295W+N527M+T(V)549W;
S95P+G120S+A121P+Y295W+A518K+N527M+T(V)
549W;
S95P+N112L+A121P+Y295W+A518K+N527M+T(V)
549W;
S95P+A121P+Y295W+A518K+T(V)549W;
S95P+A121P+Y295W+A518K+N527M;
S95P+A121P+Y295W+S458C+N539R+I541Y+T543V+
A545S+S546GCGV+G547S+S548T+T549A;
S95P+A121P+Y295W+S458SGGC+N539R+I541Y+
T543V+A545S+S546GCGV+G547S+S548T+T549A;
T43K+S95P+A121P+Y295W+N527M+T(V)549W;
S95P+A121P+Y295W+S458SCGG+N539R+I541Y+
T543V+A545S+S546GCGV+G547S+S548T+T549A;
and wherein the increase in raw starch hydrolytic activity
compared to SEQ ID NO: 2 is at least 2%.

[7]. The glucoamylase variant of paragraph 6, wherein the
variant comprises a combination of specific substitutions
selected from the group consisting of:
T43K+S95P+G120S+A121P+Y295W+Q318Y+A518K+
N527M+T(V)549W;
S95P+G120S+A121P+Y295W+N539R+I541Y+T543V+
A545S+S546GCGV+G547S+S548T+T549A;
T43K+S95P+A121P+Y295W+Q318Y+N527M+T(V)
549W;
S95P+A121P+Y295W+T116R+N527M+T(V)549W;

T43K+S95P+A121P+Y295W+Q318Y+A518K+N527M+T(V)549W;
S95P+A121P+Y295W+A117Q+N527M+T(V)549W;
S95P+T116R+A121P+Y295W+A518K+N527M+T(V)549W;
V18M+T43K+S95P+A121P+Q318Y+A518K+T(V)549W;
S95P+A121P+Y295W+Q318Y+N527M+T(V)549W;
S95P+G120S+A121P+Y295W+N527M+T(V)549W;
S95P+A121P+Y295W+A518K+N527M+T(V)549W;
S95P+N112L+A121P+Y295W+N527M+T(V)549W;
S95P+A121P+Y295W+N527M+T(V)549W;
S95P+G120S+A121P+Y295W+A518K+N527M+T(V)549W;
S95P+N112L+A121P+Y295W+A518K+N527M+T(V)549W;
S95P+A121P+Y295W+A518K+T(V)549W;
S95P+A121P+Y295W+A518K+N527M;
S95P+A121P+Y295W+S458C+N539R+I541Y+T543V+A545S+S546GCGV+G547S+S548T+T549A;
and wherein the increase in raw starch hydrolytic activity compared to SEQ ID NO: 2 is at least 15%, such as at least 20%.

[8]. A glucoamylase variant, having increased raw starch hydrolytic activity at pH=4.0, T=32° C., compared to the glucoamylase disclosed in SEQ ID NO: 2, wherein the variant comprises the modifications selected from:
i) replacing the starch binding domain amino acids 463-556 of SEQ ID NO: 2 with amino acids 466-559 of SEQ ID NO: 4; and/or
ii) introducing the following substitutions and insertions: N539R+I541Y+T543V+A545S+S546GCGV+G547S+S548T+T549A using SEQ ID NO: 2 for numbering;
wherein the variants have at least 85%, at least 90%, at least 95% identity, at least 96%, at least 97%, at least 98%, or at least 99%, but less than 100%, sequence identity to the amino acid sequence of SEQ ID NO: 2, and wherein the increase in raw starch hydrolytic activity compared to SEQ ID NO: 2 is at least 10%, such as at least 15%.

[9]. A glucoamylase variant, having increased raw starch hydrolytic activity at pH=4.0, T=32° C., compared to the glucoamylase disclosed in SEQ ID NO: 4, wherein the variant comprises the modifications of introducing the following substitutions and insertions: N539R+I541Y+T543V+A545S+S546GCGV+G547S+S548T+T549A using SEQ ID NO: 2 for numbering; wherein the variants have at least 85%, at least 90%, at least 95% identity, at least 96%, at least 97%, at least 98%, or at least 99%, but less than 100%, sequence identity to the amino acid sequence of SEQ ID NO: 4, and wherein the increase in raw starch hydrolytic activity compared to SEQ ID NO: 4 is at least 15%.

[10]. A glucoamylase variant, having increased raw starch hydrolytic activity at pH=4.0, T=32° C., compared to the glucoamylase disclosed in SEQ ID NO: 2, wherein the variant comprises the modifications selected from:
i) replacing the starch binding domain amino acids 463-556 of SEQ ID NO: 2 with amino acids 466-559 of SEQ ID NO: 4; and/or
ii) introducing the substitutions G459C+N527M+T(V)549W using SEQ ID NO: 2 for numbering; wherein the variants have at least 85%, at least 90%, at least 95% identity, at least 96%, at least 97%, at least 98%, or at least 99%, but less than 100%, sequence identity to the amino acid sequence of SEQ ID NO: 2, and wherein the increase in raw starch hydrolytic activity compared to SEQ ID NO: 2 is at least 10%, such as at least 15%.

[11]. The glucoamylase variant of any of paragraphs 8-10, further comprising any of the substitutions:

V18M, T43K, T116R, A271F, Y295W, Q318Y; particularly, Y295W; T116R+Y295W; T43K+Y295W+Q318Y; V18M+T43K+Q318Y; V18M+T43K+T116R+Q318Y.

[12]. The glucoamylase variant of paragraph 11, further comprising S95P+A121P.

[13]. The glucoamylase variant of any of paragraphs 1-12, wherein the number of substitutions or insertions are 1-20, e.g., 1-10 and 1-5, such as 1, 2, 3, 4, 5, 6, 7, 8, 9 or 10 substitutions or insertions.

[14]. A method for increasing raw starch hydrolysis activity of a glucoamylase comprising the steps:
(a) providing a hybrid glucoamylase comprising a first amino acid sequence consisting of amino acids 1-454 of SEQ ID NO: 2, a second amino acid sequence selected from amino acids 455-462 of SEQ ID NO: 2 or amino acids 455-465 of SEQ ID NO: 4, and a third amino acid sequence selected from amino acids 463-556 of SEQ ID NO: 2 or amino acids 466-559 of SEQ ID NO: 4; and/or
(b) introducing a combination of substitutions selected from at least one, preferably at least two, preferably at least three, preferably at least four of: V18M, T43K, N112L, T116R, A117Q, G120S, A271F, Y295W, Q318Y; and/or
(c) Introducing at least three, preferably at least four substitutions selected from the group: S458C, S458SCGG, S458SGGC, A493V, A518K, E520Q, N527M, S540K, R, S(G)546P, T(V)549W, N503R, N539R+I541Y+T543V+A545S+S546GCGV+G547S+S548T+T549A.

[15]. The method of paragraph 14, further comprising introducing the substitutions S95P+A121P.

[16]. A method for increasing raw starch hydrolysis activity of a glucoamylase comprising the steps:
(a) providing a hybrid glucoamylase comprising a first amino acid sequence consisting of amino acids 1-454 of SEQ ID NO: 2, a second amino acid sequence selected from amino acids 455-465 of SEQ ID NO: 4, and a third amino acid sequence selected from amino acids 466-559 of SEQ ID NO: 4; and/or
(b) introducing a combination of substitutions selected from at least one of: V18M, T43K, T116R, G120S, Y295W, Q318Y; and/or
(c) introducing one of 3 option: i) N539R+I541Y+T543V+A545S+S546GCGV+G547S+S548T+T549A; ii) N539R+I541Y+T543V+A545S+S546PCGV+G547S+S548T+T549A; iii) at least three substitutions selected from the group: S458SCGG, N527M, T(V)549W, and N503R.

[17]. The method of paragraph 16, further comprising introducing the substitutions S95P+A121P.

[18]. A composition comprising the glucoamylase variant of any of paragraphs 1-13.

[19]. A use of a glucoamylase variant of any of paragraphs 1-13 for production of syrup and/or a fermentation product.

[20]. A process of producing a fermentation product from starch-containing material comprising the steps of:
(a) liquefying starch-containing material in the presence of an alpha amylase;
(b) saccharifying the liquefied material; and
(c) fermenting with a fermenting organism;
wherein step (b) is carried out using at least a glucoamylase variant of any of paragraphs 1-13.

[21]. The process of paragraph 20, wherein step (b) and step (c) are carried out simultaneously.

[22]. A process of producing a fermentation product from starch-containing material, comprising the steps of:
(a) saccharifying starch-containing material at a temperature below the initial gelatinization temperature of said starch-containing material; and
(b) fermenting with a fermenting organism,
wherein step (a) is carried out using at least a glucoamylase variant of any of paragraphs 1-13.

[23]. A process of producing a syrup product from starch-containing material, comprising the step of:
  (a) liquefying starch-containing material in the presence of an alpha amylase;
  (b) saccharifying the liquefied material in the presence of a glucoamylase variant of any of paragraphs 1-13.

[24]. The process of any of the paragraphs 20-22, wherein the fermentation product is ethanol.

[25]. The process of paragraph 24, wherein variant glucoamylase present in the saccharification step is selected from a a glucoamylase variant having increased raw starch hydrolytic activity at pH=4.0, T=32° C., compared to the glucoamylase disclosed in SEQ ID NO: 2, wherein the variant is derived from the glucoamylase of SEQ ID NO: 2, and wherein the variant comprises a combination of specific substitutions selected from: V18M+T43K+S95P+A121P+Q318Y+A518K+N527M+T549W; wherein the position numbering corresponds to amino acid positions in the amino acid sequence set forth in SEQ ID NO: 2; and wherein the variants have at least 85%, at least 90%, at least 95% identity, at least 96%, at least 97%, at least 98%, or at least 99%, but less than 100%, sequence identity to the amino acid sequence of SEQ ID NO: 2; and wherein the increase in raw starch hydrolytic activity compared to SEQ ID NO: 2 is at least 5%, at least 10%, at least 15%, particularly at least 20%.

[26]. The process of any of the paragraphs 20-22, and 24-25, wherein the fermenting organism is selected from a yeast, particularly a *Saccharomyces*, more particularly a *Saccharomyces cerevisiae*.

[27]. The process of paragraph 26, wherein the yeast expresses a glucoamylase, preferably a *Gloeophyllum* sp. glucoamylase, more preferably a glucoamylase from *Gloeophyllum sepiarium*, or *Gloeophyllum trabeum*, most preferably the glucoamylase disclosed as SEQ ID NO: 2 or SEQ ID NO: 4, or a glucoamylase having at least 90% identity to SEQ ID NO: 2 or SEQ ID NO: 4.

[28]. A process of producing a syrup product from starch-containing material, comprising the step of saccharifying the starch-containing material in the presence of a glucoamylase variant of any of paragraphs 1-13, at a temperature below the initial gelatinization temperature of the starch-containing material.

[29]. A polynucleotide encoding the glucoamylase variant of any of paragraphs 1-13.

[30]. A nucleic acid construct comprising the polynucleotide of paragraph 29.

[31]. An expression vector comprising the polynucleotide of paragraph 29.

[32]. A host cell comprising the polynucleotide of paragraph 29, the nucleic acid construct of paragraph 30, or the expression vector of paragraph 31.

[33]. The host cell of paragraph 32, wherein the host cell is a yeast cell, particularly a *Saccharomyces*, such as *Saccharomyces cerevisiae*.

[34]. The process of any of the paragraphs 20-22 and 24, wherein the host cell of paragraph 32 or 33 is applied in the fermentation step.

[35]. The process of any of paragraphs 20-22, wherein a fungal acid alpha-amylase is present during step the saccharification step.

[36]. The process of paragraph 35, wherein the yeast expresses the fungal acid alpha-amylase.

[37]. The process of paragraph 35 or 36, wherein the fungal acid alpha-amylase is derived from *Rhizomucor* or *Aspergillus*, particularly *Rhizomucor pusillus*, *Aspergillus terreus*, or *Aspergillus fumigatus*, particularly the alpha-amylase selected from an alpha-amylase derived from *Rhizomucor pusillus* with an *Aspergillus niger* glucoamylase linker and starch-binding domain (SBD), preferably disclosed as SEQ ID NO: 5, preferably having one or more of the following substitutions: G128D, D143N, preferably G128D+D143N (using SEQ ID NO: 5 for numbering), and wherein the alpha-amylase variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the polypeptide of SEQ ID NO: 5.

[38]. A method of producing a glucoamylase variant of any of paragraphs 1-13, comprising:
  (a) cultivating the host cell of paragraph 28 under conditions suitable for expression of the variant; and
  (b) optionally recovering the variant.

The present invention is further described by the following examples.

EXAMPLES

Assays for Determining Glucoamylase Activity
Glucoamylase Activity (AGU)

The Glucoamylase Unit (AGU) is defined as the amount of enzyme, which hydrolyzes 1 micromole maltose per minute under the standard conditions (37° C., pH 4.3, substrate: maltose 100 mM, buffer: acetate 0.1 M, reaction time 6 minutes as set out in the glucoamylase incubation below), thereby generating glucose.

| glucoamylase incubation: | | |
| --- | --- | --- |
| Substrate: | | maltose 100 mM |
| Buffer: | | acetate 0.1M |
| pH: | | 4.30 ± 0.05 |
| Incubation temperature: | | 37° C. ± 1 |
| Reaction time: | 6 | minutes |
| Enzyme working range: | 0.5-4.0 | AGU/mL |

The analysis principle is described by 3 reaction steps:
Step 1 is an Enzyme Reaction:
  Glucoamylase (AMG), EC 3.2.1.3 (exo-alpha-1,4-glucan-glucohydrolase), hydrolyzes maltose to form alpha-D-glucose. After incubation, the reaction is stopped with NaOH.
Steps 2 and 3 Result in an Endpoint Reaction:
  Glucose is phosphorylated by ATP, in a reaction catalyzed by hexokinase. The glucose -6-phosphate formed is oxidized to 6-phosphogluconate by glucose-6-phosphate dehydrogenase. In this same reaction, an equimolar amount of NAD+ is reduced to NADH with a resulting increase in absorbance at 340 nm. An autoanalyzer system such as Konelab 30 Analyzer (Thermo Fisher Scientific) may be used.

| Color reaction | | |
| --- | --- | --- |
| Tris | | approx. 35 mM |
| ATP | 0.7 | mM |
| NAD+ | 0.7 | mM |
| $Mg^{2+}$ | 1.8 | mM |
| Hexokinase | >850 | U/L |
| Glucose-6-P-DH | >850 | U/L |
| pH | | approx. 7.8 |

-continued

| Color reaction | |
|---|---|
| Temperature | 37.0° C. ± 1.0° C. |
| Reaction time | 420 sec |
| Wavelength | 340 nm |

Reagents for Assay Protocols:

A stock of 1 M sodium acetate buffer was prepared by dissolving 44.4 g of sodium acetate trihydrate (Merck cat. no. 61751805001730) and 37.5 ml of acetic acid (Fisher cat. no. 11007) in Milli Q water. pH was adjusted to 4.3 and the final volume of buffer was made up to 1000 ml. This buffer stock was stored at 4° C. until use. A 100 mM working solution was prepared by adding 100 ml of 1 M stock to 900 ml of Milli Q water.

A substrate solution of 0.1% 4-nitrophenyl-α-D-glucopyranoside (pNPG) was freshly prepared by dissolving 100 mg of 4-nitrophenyl-α-D-glucopyranoside (Sigma cat. no. N1377) in 100 ml of 100 mM sodium acetate buffer (pH 4.3).

A stock of 0.1M Borax (di-sodium tetraborate) stop solution was prepared by dissolving 38.1 g of borax (Fisher cat. no. 27965) in 1000 ml Milli Q water. This stop solution was stored at room temperature until use.

A substrate solution of 1% maltose was freshly prepared by dissolving 1 g of maltose (Sigma cat. no. M5885) in 100 ml of 100 mM sodium acetate buffer (pH 4.3).

A stock of 1000 μM acarbose solution was prepared by dissolving 64.6 mg of acarbose (Sigma cat. no. A8980) in 100 ml Milli Q water. This stock was stored at 4° C. until use. A 5.6 μM working solution was prepared by adding 336 μl of 1000 μM stock to 59.66 ml of Milli Q water.

Determination of Specific Activity (SA):

Acarbose assay method was used for the determination of specific activity in the culture supernatants. This method uses a known concentration of acarbose resulting in 50% inhibition of the protein activity. The culture supernatants were normalized for their activity based on a Relative Amyloglucosidase activity calculation (RAG) and the inhibition by known concentration of acarbose was determined. The resulting residual activity is then used for calculating the specific activity of amyloglucosidase in culture supernatants. The specific activity was calculated using the following equations.

$$Vsa = Vm \times (1 - Va/Vdw)$$

Vm=A505 of a variant from maltose substrate
Va=A400 of a variant with acarbose
Vdw=A400 of a variant without acarbose
Specific Glucoamylase Activity (SA)

The specific activity of the purified protein was determined by AGU assay determined by Konelab instrument.

Acid Alpha-Amylase Activity

When used according to the present invention the activity of an acid alpha-amylase may be measured in AFAU (Acid Fungal Alpha-amylase Units) or FAU-F.

Acid Alpha-Amylase Activity (AFAU)

Acid alpha-amylase activity may be measured in AFAU (Acid Fungal Alpha-amylase Units), which are determined relative to an enzyme standard. 1 AFAU is defined as the amount of enzyme which degrades 5.260 mg starch dry matter per hour under the below mentioned standard conditions.

Acid alpha-amylase, an endo-alpha-amylase (1,4-alpha-D-glucan-glucanohydrolase, E.C. 3.2.1.1) hydrolyzes alpha-1,4-glucosidic bonds in the inner regions of the starch molecule to form dextrins and oligosaccharides with different chain lengths. The intensity of color formed with iodine is directly proportional to the concentration of starch. Amylase activity is determined using reverse colorimetry as a reduction in the concentration of starch under the specified analytical conditions.

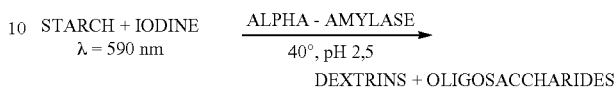

STARCH + IODINE
λ = 590 nm
ALPHA - AMYLASE
40°, pH 2,5
DEXTRINS + OLIGOSACCHARIDES blue/violet t=23 sec. decoloration
Standard Conditions/Reaction Conditions:

| Substrate: | Soluble starch, approx. 0.17 g/L |
|---|---|
| Buffer: | Citrate, approx. 0.03M |
| Iodine (I2): | 0.03 g/L |
| CaCl$_2$: | 1.85 mM |
| pH: | 2.50 ± 0.05 |
| Incubation temperature: | 40° C. |
| Reaction time: | 23 seconds |
| Wavelength: | 590 nm |
| Enzyme concentration: | 0.025 AFAU/mL |
| Enzyme working range: | 0.01-0.04 AFAU/mL |

A folder EB-SM-0259.02/01 describing this analytical method in more detail is available upon request to Novozymes A/S, Denmark, which folder is hereby included by reference.

Determination of FAU-F

FAU-F Fungal Alpha-Amylase Units (Fungamyl) is measured relative to an enzyme standard of a declared strength.

| Reaction conditions | |
|---|---|
| Temperature | 37° C. |
| pH | 7.15 |
| Wavelength | 405 nm |
| Reaction time | 5 min |
| Measuring time | 2 min |

A folder (EB-SM-0216.02) describing this standard method in more detail is available on request from Novozymes A/S, Denmark, which folder is hereby included by reference.

Enzymes and Enzyme Blends

Protease PfuS: Protease derived from *Pyrococcus furiosus* shown in SEQ ID NO: 7.

Alpha-Amylase BE369 (AA369): *Bacillus stearothermophilus* alpha-amylase disclosed herein as SEQ ID NO: 8, and further having the mutations: I181*+G182*+N193F+V59A+Q89R+E129V+K177L+R179E+Q254S+M284V truncated to 491 amino acids (using SEQ ID NO: 8 for numbering).

Alpha-amylase blend A: Blend comprising Alpha-amylase AA369, and protease PfuS (dosing: 2.1 μg EP/g DS AA369, 3.0 μg EP/g DS PfuS, where EP is enzyme protein and DS is total dry solids).

Alpha-amylase B: *Bacillus stearothermophilus* alpha-amylase disclosed herein as SEQ ID NO: 8, and further having the mutations: I181*+G182*+N193F.

Example 1. Variants According to the Invention Having Improved Raw Starch Hydrolysis The raw starch degradation performance of the variants was measured by release of glucose from granular starch in combination with a fungal alpha amylase disclosed herein as SEQ ID NO: 6. The purified glucoamylase was diluted to 12.5 µg/ml by 50 mM acetate buffer (pH 4.0). Thirty microliter of enzyme solution was transferred into 2.0 ml deep well palate wells, and 270 µl substrate solution (0.2% raw starch dispersed in 50 mM acetate buffer pH 4.0, 1 mM $CaC_2$, 0.16 µg/ml fungal alpha amylase disclosed herein as SEQ ID NO: 6) was added to start the reaction. The substrate solution was stirred until just before being added. After incubation at 32° C. for 120 min with shaking at 1200 rpm, samples were centrifuged to spin down residual starch granule and glucose concentration of supernatant was measured by mixing 20 ul aliquot with 200 ul commercial glucose oxidase-peroxidase method-based glucose detection solution (Glucose C2 test, Wako Chemical. Co) in which acarbose as a glucoamylase inhibitor had been dissolved to be 0.5 mM prior to use. Absorbance at 505 nm was measured and relative performance was calculated.

Variants of the Invention

| GSA | SA | RSH | RSH/mal | linker | SBD | Mutation in core | Mutaion in SBD |
| --- | --- | --- | --- | --- | --- | --- | --- |
| GSA213 | 7.5 | 1.80 | 1.52 | Gt | Gt | V18M, T43K, S95P, T116R, A121P, Q318Y | S(G)546P, loop2 |
| GSA170 | 6.6 | 1.77 | 1.80 | Gt | Gt | S95P, A121P, Y295W, T116R | S(G)546P, loop2 |
| GSA168 | 7.2 | 1.68 | 1.67 | Gt | Gt | T43K, S95P, A121P, Y295W, Q318Y | S(G)546P, loop2 |
| GSA177 | 6.6 | 1.64 | 1.60 | Gt | Gt | T43K, S95P, G120S, A121P, Y295W, Q318Y | loop2 |
| GSA215 | 7.2 | 1.64 | 1.41 | Gt | Gt | V18M, T43K, S95P, T116R, A121P, Q318Y | G459C, N527M, T(V)549W |
| GSA216 | 7.4 | 1.62 | 1.33 | Gt | Gt | V18M, T43K, S95P, A121P, Q318Y | G459C, N527M, T(V)549W, N503 R |
| GSA212 | 7.9 | 1.62 | 1.32 | Gt | Gt | V18M, T43K, S95P, A121P, Q318Y | S(G)546P, loop2 |
| GSA175 | 7.3 | 1.61 | 1.47 | Gt | Gt | T43K, S95P, A121P, Y295W, Q318Y | G459C, N527M, T(V)549W |
| GSA169 | 6.1 | 1.60 | 1.64 | Gt | Gt | S95P, A121P, Y295W, G120S | S(G)546P, loop2 |
| GSA214 | 7.5 | 1.59 | 1.34 | Gt | Gt | V18M, T43K, S95P, A121P, Q318Y | G459C, N527M, T(V)549W |
| GSA165 | 6.2 | 1.58 | 1.53 | Gt | Gt | S95P, A121P, Y295W | S(G)546P, loop2 |
| GSA167 | 7.1 | 1.56 | 1.52 | Gt | Gt | T43K, S95P, A121P, Y295W, Q318Y | loop2 |
| GSA138 | 6.2 | 1.53 | 1.65 | Gt | Gt | S95P, T116R, A121P, Y295W | loop2 |
| GSA201 | 7.2 | 1.47 | 1.27 | Gt | Gt | T43K, S95P, A121P, Y295W, Q318Y | N527M, T(V)549W, N503R |
| GSA050 | 6.2 | 1.43 | 1.56 | Gt | Gt | S95P, A121P, Y295W | loop2 |
| GSA233 | 6.9 | 1.43 | 1.28 | Gs | Gs | V18M, T43K, S95P, A121P | A518K, N527M, T549W |
| GSA176 | 6.6 | 1.41 | 1.43 | Gt | Gt | T43K, S95P, G120S, A121P, Y295W, Q318Y | A518K, N527M, T(V)549W |
| GSA188 | 7.4 | 1.41 | 1.19 | Gs | Gs | T43K, S95P, A121P, Q318Y | A493V, A518K, N527M, T549W |
| GSA141 | 5.7 | 1.40 | 1.58 | Gt | Gt | S95P, G120S, A121P, Y295W | loop2 |
| GSA234 | 6.7 | 1.40 | 1.30 | Gs | Gs | V18M, T43K, S95P, A121P, Y295W | A518K, N527M, T549W |
| GSA112 | 7.4 | 1.39 | 1.19 | Gt | Gt | T43K, S95P, A121P, Y295W, Q318Y | N527M, T(V)549W |
| GSA198 | 7.5 | 1.39 | 1.13 | Gs | Gs | T43K, S95P, A121P, Q318Y | N527M, T549W |
| GSA204 | 8.0 | 1.39 | 1.11 | Gs | Gs | V18M, T43K, S95P, A121P, Q318Y | N527M, T549W |
| GSA100 | 6.2 | 1.36 | 1.49 | Gt | Gt | S95P, A121P, Y295W, T116R | N527M, T(V)549W |
| GSA222 | 7.4 | 1.36 | 1.16 | Gs | Gs | V18M, T43K, S95P, T116R, A121P, Q318Y | A493V, N527M, T549W |
| GSA205 | 7.9 | 1.36 | 1.04 | Gs | Gs | V18M, T43K, S95P, A121P, Q318Y | A493V, N527M, T549W |
| GSA166 | 7.0 | 1.35 | 1.44 | Gt | Gt | T43K, S95P, A121P, Y295W, Q318Y | A518K, N527M, T(V)549W |
| GSA103 | 6.4 | 1.35 | 1.40 | Gt | Gt | S95P, A121P, Y295W, A117Q | N527M, T(V)549W |
| GSA203 | 7.9 | 1.35 | 1.01 | Gs | Gs | V18M, T43K, S95P, A121P, Q318Y | A493V, A518K, N527M, T549W |
| GSA186 | 7.6 | 1.34 | 1.15 | Gs | Gs | T43K, S95P, A121P, Q318Y | A518K, N527M, T549W |
| GSA221 | 7.2 | 1.34 | 1.14 | Gs | Gs | V18M, T43K, S95P, T116R, A121P, Q318Y | N527M, T549W |
| GSA199 | 7.5 | 1.34 | 1.09 | Gs | Gs | T43K, S95P, A121P, Q318Y | A493V, N527M, T549W |
| GSA139 | 6.0 | 1.33 | 1.52 | Gt | Gt | S95P, T116R, A121P, Y295W | A518K, N527M, T(V)549W |
| GSA219 | 7.7 | 1.33 | 1.10 | Gt | Gt | V18M, T43K, S95P, A121P, Q318Y | A518K, T(V)549W |

-continued

| GSA | SA | RSH | RSH/mal | linker | SBD | Mutation in core | Mutaion in SBD |
|---|---|---|---|---|---|---|---|
| GSA182 | 7.2 | 1.32 | 1.12 | Gs | Gs | T43K, S95P, A121P, Y295W, Q318Y | A518K, N527M, T549W |
| GSA220 | 7.0 | 1.31 | 1.17 | Gs | Gs | V18M, T43K, S95P, T116R, A121P, Q318Y | A518K, T549W |
| GSA111 | 7.8 | 1.30 | 1.56 | Gt | Gt | S95P, A121P, Y295W, Q318Y | N527M, T(V)549W |
| GSA102 | 6.2 | 1.28 | 1.36 | Gt | Gt | S95P, G120S, A121P, Y295W | N527M, T(V)549W |
| GSA164 | 6.3 | 1.28 | 1.34 | Gt | Gt | S95P, A121P, Y295W | A518K, N527M, T(V)549W |
| GSA048 | 6.7 | 1.28 | 1.30 | Gs | Gt | S95P, A121P, Y295W | N527M, T(V)549W |
| GSA099 | 6.9 | 1.28 | 1.25 | Gt | Gt | S95P, N112L, A121P, Y295W | N527M, T(V)549W |
| GSA047 | 7.0 | 1.27 | 1.22 | Gt | Gt | S95P, A121P, Y295W | N527M, T(V)549W |
| GSA202 | 7.8 | 1.27 | 1.04 | Gs | Gs | V18M, T43K, S95P, A121P, Q318Y | A518K, N527M, T549W |
| GSA196 | 7.2 | 1.26 | 1.09 | Gs | Gs | T43K, S95P, A121P, Y295W, Q318Y | N527M, T549W |
| GSA142 | 5.8 | 1.25 | 1.44 | Gt | Gt | S95P, G120S, A121P, Y295W | A518K, N527M, T(V)549W |
| GSA136 | 6.3 | 1.24 | 1.26 | Gt | Gt | S95P, N112L, A121P, Y295W | A518K, N527M, T(V)549W |
| GSA218 | 7.6 | 1.24 | 1.04 | Gs | Gs | V18M, T43K, S95P, A121P, Q318Y | A518K, T549W |
| GSA163 | 6.4 | 1.23 | 1.28 | Gs | Gs | S95P, A121P, Y295W | A493V, A518K, E520Q, T549W |
| GSA183 | 6.2 | 1.22 | 1.27 | Gs | Gs | S95P, A121P, Y295W | A518K, N527M, T549W |
| GSA051 | 6.4 | 1.22 | 1.26 | Gt | Gt | S95P, A121P, Y295W | A518K, T(V)549W |
| GSA046 | 6.9 | 1.21 | 1.24 | Gt | Gt | S95P, A121P, Y295W | A518K, N527M |
| GSA114 | 6.4 | 1.21 | 1.16 | Gt | Gt | S95P, A121P, Y295W | S458C, loop2 |
| GSA197 | 6.4 | 1.17 | 1.19 | Gs | Gs | S95P, A121P, Y295W | N527M, T549W |
| GSA049 | 7.1 | 1.16 | 1.11 | Gt | Gt | S95P, A121P, Y295W | |
| GSA081 | 6.5 | 1.09 | 1.14 | Gs | Gs | S95P, A121P, A271F, Y295W | A518K, N527M, T549W |
| GSA131 | 6.5 | 1.08 | 1.09 | Gs | Gs | S95P, A121P, Y295W | A493V |
| GSA132 | 6.4 | 1.06 | 1.04 | Gs | Gs | S95P, A121P, Y295W | S540K |
| GSA133 | 6.6 | 1.05 | 1.07 | Gs | Gs | S95P, A121P, Y295W | S540R |
| GSA078 | 6.6 | 1.05 | 1.05 | Gs | Gs | S95P, A121P, Y295W | A518K, N527M |
| GSA117 | 6.5 | 1.04 | 1.16 | Gt | Gt | S95P, A121P, Y295W | G461C, loop2 |
| GSA110 | 6.3 | 1.03 | 0.99 | Gt | Gt | T43K, S95P, A121P, Y295W | N527M, T(V)549W |
| GSA115 | 6.4 | 1.02 | 1.09 | Gt | Gt | S95P, A121P, Y295W | G459C, loop2 | loop2 = N539R + I541Y + T543V + A545S + S546GCGV + G547S + S548T + T549A using SEQ ID NO: 2 for numbering.

Example 2: Evaluation of Simultaneous Saccharification and Fermentation (SSF) Performance of Variant GSA202 in Combination with a Glucoamylase Expressing Yeast Enzyme blends comprising prior art glucoamylases (glucoamylases from *Talaromyces emersonii*, T-AMG (SEQ ID NO: 9), and from *Trametes cingulata*, Tc-AMG (SEQ ID NO: 10), in blends with an acid fungal alpha-amylase denoted PE096 (SEQ ID NO: 6) were used as the reference blends to evaluate the performance of the similar enzyme blends containing the glucoamylase variant GSA202. Since GSA202 possesses higher raw starch hydrolysis activity than the reference blends containing both T-AMG and Tc-AMG, only 40% of PE096 was supplemented (a 60% reduction) with GSA202. Enzyme blends and ratios were as shown in the table below. In all reference blends containing two glucoamylases, of the total dose of 0.36 AGU/g DS, 0.290 AGU/g DS was derived from T-AMG and the other 0.0670 AGU/g DS was derived from Tc-AMG. GSA202 is a glucoamylase variant according to the invention based on SEQ ID NO: 2 herein having the substitutions as disclosed in Example 1. The alpha-amylase PE096 is a variant *Rhizomucor pusillus* alpha-amylase with *Aspergillus niger* glucoamylase linker and starch binding domain (SBD) and is disclosed in SEQ ID NO: 6.

$$\text{Enz. dose(uL)} = \frac{\text{Total GA dose}\left(\frac{AGU}{g\,DS}\right) \times \text{Mass Weight(g)} \times \text{Dry solid content } (\%\,DS) \times 1000}{\text{Stock enzyme conc.}\left(\frac{AGU}{mL}\right)}$$

TABLE 1

Enzyme treatment in SSF of two industrial plant mashes

| Enzyme blend | Glucoamylase (GA) | Total GA Dose (AGU/g DS) | Alpha-amylase | Dose (FAU-F/g DS) |
|---|---|---|---|---|
| 1 | T-AMG + Tc-AMG | 0.36 | PE096 | 0.0057 |
| 2 | GSA202 | 0.36 | PE096 | 0.00225 |
| 3 | T-AMG + Tc-AMG | 0.36 | PE096 | 0.0171 |
| 4 | GSA202 | 0.36 | PE096 | 0.00675 |

These 4 blends were evaluated in an SSF using two liquefied industrial plant corn mashes representing both Alpha-amylase blend A (Mash 1) and Alpha-amylase B (Mash 2). These mashes were supplemented with 3 ppm penicillin. The amount of urea added to Mash 1 and Mash 2 were 400 ppm and 1000 ppm, respectively. Both plant mashes were adjusted to pH 5.1 using 40% $H_2SO_4$ prior to dispensing mash into flasks. Approximately 55 g (55±0.03) of mash was added into each 125 mL Corning Disposable Erlenmeyer flask that had a 0.048" hole on the cap for venting. Each flask was dosed with enzymes according to Table 1 and glucoamylase expressing yeast at the dose of $5 \times 10^6$ cells/g DS. The glucoamylase expressing yeast expresses the wild type glucoamylase disclosed herein as SEQ ID NO: 2 and is similar to the yeast strain described in similar to yMHCT471 as described in PCT/US2017/063159. Water was added into each flask such the total added volume of enzymes and water was equal across each sample in each mash type. To prepare the yeast prior to dosing, 150 uL glycerol stock culture was inoculated into 50 mL of 6% YPD medium (1% (w/v) yeast extract, 2% (w/v) peptone and 6% (w/v) dextrose) in a 125 mL Erlenmeyer flask. The flask was incubated overnight at 33° C. for approximately 16 hrs while shaking at 130 rpm. Then, the yeast was collected by centrifugation at 3500×g for 10 minutes. Yeast pellet was washed two times in deionized water by resuspended the pellet into 45 mL deionized water followed by centrifugation. After two washes, the pellet was resuspended in ~45 mL water and the yeast titer was determined using Chemometec's Nucleo-Counter YC-100 according to the manufacturer's instruction.

Flasks were incubated for the total of 54 hrs at 32° C. while shaking at 120 rpm. Samples were collected at 6, 24, 48 and 54 hrs. At each time point, samples were prepared for HPLC by removing approximately 4 grams of fermentation sample and mixed it with 40 uL of 40% $H_2SO_4$. The mixture was centrifuged for 10 minutes at 3500×g, and the supernatant was filtered through 0.2 uM Whatman nylon filter. Filtered samples were analyzed on an Agilent HPLC 1100/1200 series with Chemstattion software. Samples were separated on Bio-Rad HPX-87H Ion Exclusion column (300 mm×7.8 mm) with a cation H guard cartridge. The mobile phase, 5 mM $H_2SO_4$, was run at 0.8 ml/min at 65° C. and the RI detector temperature was set at 55° C. The method quantifies several analytes using calibration standards (4 point calibration with forced through zero) for dextrins (DP4+), maltotriose (DP3), maltose (DP2), glucose (DP1), fructose, acetic acid, lactic acid, glycerol and ethanol. HPLC results on ethanol, glycerol, DP3 (maltotriose), DP2 (maltose) are shown in Table 2 and Table 3.

Blends containing GSA202 consistently exhibited higher ethanol yield relative to reference T-AMG/Tc-AMG glucoamylase. This is true with three difference type of GA blends (Ultra T, Excel T and Achieve T) and across two different type of plant mashes. The increase in ethanol with GSA202 range from 0.1% to 1.28%.

TABLE 2

Ethanol level following SSF in two plant mashes for 54 Hrs

| Enzyme blend | Ethanol level (% w/v) | | Ethanol yield increase (Relative to reference GA) | |
|---|---|---|---|---|
| | Mash 1 | Mash 2 | Mash 1 | Mash 2 |
| 1 | 13.8865 | 14.5545 | 0.00% | 0.00% |
| 2 | 13.9685 | 14.6530 | 0.59% | 0.68% |
| 3 | 13.8560 | 14.6330 | 0.00% | 0.00% |
| 4 | 14.0340 | 14.6475 | 1.28% | 0.10% |

In addition to ethanol increase, another benefit seen with GSA202 is a lower accumulation level of glycerol relative to reference glucoamylases. This may suggest that the yeast was less stressed when GSA202 was used in SSF. Other desirable properties were observed with GSA202 such as lower level of DP3, DP2 and acetic acid.

TABLE 3

HPLC results of selected analytes of interest following SSF in two plant mashes for 54 hrs

| Enzyme blend | Glycerol (% w/v) | | DP3 level (% w/v) | | DP2 level(% w/v) | | Acetic Acid Level (% w/v) | |
|---|---|---|---|---|---|---|---|---|
| | Mash 1 | Mash 2 | Mash 1 | Mash 2 | Mash 1 | Mash 2 | Mash 1 | Mash 2 |
| 1 | 0.9545 | 1.5370 | 0.1195 | 0.1290 | 0.0890 | 0.1515 | 0.0875 | 0.0710 |
| 2 | 0.8825 | 1.5195 | 0.0975 | 0.1075 | 0.0635 | 0.1160 | 0.0470 | 0.0805 |
| 3 | 0.9410 | 1.5510 | 0.1210 | 0.1355 | 0.0870 | 0.1645 | 0.0650 | 0.1035 |
| 4 | 0.8910 | 1.5000 | 0.1005 | 0.1070 | 0.0645 | 0.1100 | 0.0490 | 0.0480 |

Example 3: Simultaneous Saccharification and Fermentation (SSF) Performance of Variant GSA202 with a Commercial Yeast, Ethanol Red A study similar to Example 2 was conducted to compare the SSF performance of reference glucoamylases and GA containing GSA202 with Ethanol Red yeast. In all reference blends containing two glucoamylases (T/Tc), of the total dose of 0.6 AGU/g DS, 0.483 AGU/g DS was derived from T-AMG and the other 0.117 AGU/g DS was derived from Tc-AMG. All enzymes used in Table 4 have been described in Example 2.

TABLE 4

Enzyme dosing in SSF following liquefaction

| Enzyme blend | Glucoamylase (GA) | Total GA Dose (AGU/g DS) | Alpha-amylase | Dose (FAU-F/g DS) |
|---|---|---|---|---|
| 1 | T-AMG + Tc-AMG | 0.60 | PE096 | 0.0057 |
| 2 | GSA202 | 0.609 | PE096 | 0.00225 |
| 3 | T-AMG + Tc-AMG | 0.60 | PE096 | 0.0171 |
| 4 | GSA202 | 0.609 | PE096 | 0.00675 |

The 4 blends were evaluated in an SSF using two liquefied industrial plant corn mashes representing Alpha-amylase blend A (Mash 1 & Mash 2). These mashes were supplemented with 3 ppm penicillin. The amount of urea added to the mashes were 400 ppm. All plant mashes were adjusted to pH 5.1 using 40% $H_2SO_4$ prior to dispensing mash into flasks. Approximately 60 g (55±0.03) of mash was added into each 125 mL Corning Disposable Erlenmeyer flask that had a 0.048" hole on the cap for venting. Each flask was dosed with enzymes according to Table 4 and Ethanol Red yeast was dosed at 0.066 g dry Ethanol Red yeast (following a rehydration for 30 minutes at 32° C.; 2.2 g dry yeast into 40 mL water). Water was added into each flask such the total added volume of enzymes and water was equal across each sample in each mash type. Flasks were incubated for the total of 54 hrs at 32° C. while shaking at 120 rpm. Samples were collected at 6, 24, 48 and 54 hrs. A sample of the starting material of each mash was also prepared for HPLC analysis to determine the time zero of each plant mash. At each time point, samples were prepared and analyzed by HPLC method as described in Example 1. HPLC results on ethanol, glycerol, DP2 (maltose) and acetic acid (acetate) are shown in Table 5 and Table 6. Blends containing GSA202, exhibited higher ethanol yield relative to reference T-AMG/Tc-AMG glucoamylase. The increase in ethanol with GSA202 is shown in Table 5 below.

TABLE 5

Ethanol level following SSF in three plant mashes for 54 Hrs

| Enzyme blends | Ethanol level (% w/v) | | Ethanol yield increase (Relative to reference GA) | |
|---|---|---|---|---|
| | Mash 1 | Mash 2 | Mash 1 | Mash 2 |
| 1 | 13.416 | 14.267 | 0.00% | 0.00% |
| 2 | 13.494 | 14.370 | 0.58% | 0.72% |
| 3 | 13.433 | 14.290 | 0.00% | 0.00% |
| 4 | 13.537 | 14.331 | 0.77% | 0.29% |

In addition to ethanol increase, another benefit seen with GSA202 is a lower accumulation level of glycerol relative to reference GAs. Other desirable properties were mostly observed with GSA202 such as lower level of DP2 and acetic acid.

TABLE 6

HPLC results of selected analytes of interest following SSF in three plant mashes for 54 Hrs

| Enzyme blends | Glycerol (% w/v) | | DP2 level (% w/v) | | Acetic Acid Level (% w/v) | |
|---|---|---|---|---|---|---|
| | Mash 1 | Mash 2 | Mash 1 | Mash 2 | Mash 1 | Mash 2 |
| 1 | 1.120 | 1.823 | 0.101 | 0.152 | 0.093 | 0.135 |
| 2 | 1.009 | 1.726 | 0.079 | 0.133 | 0.063 | 0.112 |
| 3 | 1.111 | 1.840 | 0.099 | 0.154 | 0.077 | 0.146 |
| 4 | 1.025 | 1.750 | 0.092 | 0.152 | 0.073 | 0.108 |

The invention claimed is:

1. A glucoamylase variant, having increased raw starch hydrolytic activity at pH=4.0, T=32° C., compared to the glucoamylase disclosed in SEQ ID NO: 2, wherein the variant is derived from a glucoamylase having a catalytic domain comprising amino acids 1-454 of SEQ ID NO: 2 or 1-454 of SEQ ID NO: 4, a linker comprising amino acids 455-462 of SEQ ID NO: 2 or amino acids 455-465 of SEQ ID NO: 4 and a starch binding domain comprising amino acids 463-556 of SEQ ID NO: 2 or amino acids 466-559 of SEQ ID NO: 4, and wherein the variant further comprises a substitution at one or more positions selected from the group consisting of:

V18M+T43K+S95P+A121P+Q318Y+A518K+N527M+T549W;
V18M+T43K+S95P+T116R+A121P+Q318Y+N539R+I541Y+T543V+A545S+S546PCGV+G547S+S548T+T549A;
S95P+A121P+Y295W+T116R+N539R+I541Y+T543V+A545S+S546PCGV+G547S+S548T+T549A;
T43K+S95P+A121P+Y295W+Q318Y+N539R+I541Y+T543V+A545S+S546PCGV+G547S+S548T+T549A;
T43K+S95P+G120S+A121P+Y295W+Q318Y+N539R+I541Y+T543V+A545S+S546GCGV+G547S+S548T+T549A;
V18M+T43K+S95P+T116R+A121P+Q318Y+S458SCGG+N527M+T(V)549W;
V18M+T43K+S95P+A121P+Q318Y+S458SCGG+N527M+T(V)549W+N503R;
V18M+T43K+S95P+A121P+Q318Y+N539R+I541Y+T543V+A545S+S546PCGV+G547S+S548T+T549A;
T43K+Q318Y+S95P+A121P+Y295W+S458SCGG+N527M+T(V)549W;
S95P+A121P+Y295W+G120S+N539R+I541Y+T543V+A545S+S546PCGV+G547S+S548T+T549A;
V18M+T43K+S95P+A121P+Q318Y+S458SCGG+N527M+T(V)549W;
S95P+A121P+Y295W+N539R+I541Y+T543V+A545S+S546PCGV+G547S+S548T+T549A;
T43K+S95P+A121P+Y295W+Q318Y+N539R+I541Y+T543V+A545S+S546GCGV+G547S+S548T+T549A;
S95P+T116R+A121P+Y295W+N539R+I541Y+T543V+A545S+S546GCGV+G547S+S548T+T549A;
T43K+S95P+A121P+Y295W+Q318Y+N527M+T(V)549W+N503R;
S95P+A121P+Y295W+N539R+I541Y+T543V+A545S+S546GCGV+G547S+S548T+T549A;
V18M+T43K+S95P+A121P+A518K+N527M+T549W;
T43K+S95P+G120S+A121P+Y295W+Q318Y+A518K+N527M+T(V)549W;

T43K+S95P+A121P+Q318Y+A493V+A518K+ N527M+T549W;
S95P+G120S+A121P+Y295W+N539R+I541Y+T543V+ A545S+S546GCGV+G547S+S548T+T549A;
V18M+T43K+S95P+A121P+Y295W+A518K+N527M+ T549W;
T43K+S95P+A121P+Y295W+Q318Y+N527M+T(V) 549W;
T43K+S95P+A121P+Q318Y+N527M+T549W;
V18M+T43K+S95P+A121P+Q318Y+N527M+T549W;
S95P+A121P+Y295W+T116R+N527M+T(V)549W;
V18M+T43K+S95P+T116R+A121P+Q318Y+A493V+ N527M+T549W;
V18M+T43K+S95P+A121P+Q318Y+A493V+N527M+ T549W;
T43K+S95P+A121P+Y295W+Q318Y+A518K+ N527M+T(V)549W;
S95P+A121P+Y295W+A117Q+N527M+T(V)549W;
V18M+T43K+S95P+A121P+Q318Y+A493V+A518K+ N527M+T549W;
T43K+S95P+A121P+Q318Y+A518K+N527M+T549W;
V18M+T43K+S95P+T116R+A121P+Q318Y+N527M+ T549W;
T43K+S95P+A121P+Q318Y+A493V+N527M+T549W;
S95P+T116R+A121P+Y295W+A518K+N527M+T(V) 549W;
V18M+T43K+S95P+A121P+Q318Y+A518K+T(V) 549W;
T43K+S95P+A121P+Y295W+Q318Y+A518K+ N527M+T549W;
V18M+T43K+S95P+T116R+A121P+Q318Y+A518K+ T549W;
S95P+A121P+Y295W+Q318Y+N527M+T(V)549W;
S95P+G120S+A121P+Y295W+N527M+T(V)549W;
S95P+A121P+Y295W+A518K+N527M+T(V)549W;
S95P+A121P+Y295W+N527M+T(V)549W;
S95P+N112L+A121P+Y295W+N527M+T(V)549W;
S95P+A121P+Y295W+N527M+T(V)549W;
V18M+T43K+S95P+A121P+Q318Y+A518K+N527M+ T549W;
T43K+S95P+A121P+Y295W+Q318Y+N527M+ T549W;
S95P+G120S+A121P+Y295W+A518K+N527M+T(V) 549W;
S95P+N112L+A121P+Y295W+A518K+N527M+T(V) 549W;
V18M+T43K+S95P+A121P+Q318Y+A518K+T549W;
S95P+A121P+Y295W+A493V+A518K+E520Q+ T549W;
S95P+A121P+Y295W+A518K+N527M+T549W;
S95P+A121P+Y295W+A518K+T(V)549W;
S95P+A121P+Y295W+A518K+N527M;
S95P+A121P+Y295W+S458C+N539R+I541Y+T543V+ A545S+S546GCGV+G547S+S548T+T549A;
S95P+A121P+Y295W+N527M+T549W;
S95P+A121P+A271F+Y295W+A518K+N527M+ T549W;
S95P+A121P+Y295W+S540K;
S95P+A121P+Y295W+S540R;
S95P+A121P+Y295W+S458SGGC+N539R+I541Y+ T543V+A545S+S546GCGV+G547S+S548T+T549A;
T43K+S95P+A121P+Y295W+N527M+T(V)549W; and
S95P+A121P+Y295W+S458SCGG+N539R+I541Y+ T543V+A545S+S546GCGV+G547S+S548T+T549A;
wherein the position numbering corresponds to amino acid positions in the amino acid sequence set forth in SEQ ID NO: 2; and wherein the variants have at least 85%, but less than 100%, sequence identity to the amino acid sequence of SEQ ID NO: 2.

2. The glucoamylase variant of claim 1, wherein the variant is derived from a glucoamylase having a catalytic domain comprising amino acids 1-454 of SEQ ID NO: 2, a linker comprising amino acids 455-465 of SEQ ID NO: 4 and a starch binding domain comprising amino acids 466-559 of SEQ ID NO: 4, and wherein the variant comprises a combination of specific substitutions selected from the group consisting of:
V18M+T43K+S95P+T116R+A121P+Q318Y+N539R+ I541Y+T543V+A545S+S546PCGV+G547S+S548T+ T549A;
S95P+A121P+Y295W+T116R+N539R+I541Y+T543V+ A545S+S546PCGV+G547S+S548T+T549A;
T43K+S95P+A121P+Y295W+Q318Y+N539R+I541Y+ T543V+A545S+S546PCGV+G547S+S548T+T549A;
T43K+S95P+G120S+A121P+Y295W+Q318Y+N539R+ I541Y+T543V+A545S+S546GCGV+G547S+S548T+ T549A;
V18M+T43K+S95P+T116R+A121P+Q318Y+ S458SCGG+N527M+T(V)549W;
V18M+T43K+S95P+A121P+Q318Y+S458SCGG+ N527M+T(V)549W+N503R;
V18M+T43K+S95P+A121P+Q318Y+N539R+I541Y+ T543V+A545S+S546PCGV+G547S+S548T+T549A;
T43K+S95P+A121P+Y295W+Q318Y+S458SCGG+ N527M+T(V)549W;
S95P+A121P+Y295W+G120S+N539R+I541Y+T543V+ A545S+S546PCGV+G547S+S548T+T549A;
V18M+T43K+S95P+A121P+Q318Y+S458SCGG+ N527M T(V)549W;
S95P+A121P+Y295W+N539R+I541Y+T543V+A545S+ S546PCGV+G547S+S548T+T549A;
T43K+S95P+A121P+Y295W+Q318Y+N539R+I541Y+ T543V+A545S+S546GCGV+G547S+S548T+T549A;
S95P+T116R+A121P+Y295W+N539R+I541Y+T543V+ A545S+S546GCGV+G547S+S548T+T549A;
T43K+S95P+A121P+Y295W+Q318Y+N527M+T(V) 549W+N503R; and
S95P+A121P+Y295W+N539R+I541Y+T543V+A545S+ S546GCGV+G547S+S548T+T549A;
and wherein the increase in raw starch hydrolytic activity compared to SEQ ID NO: 2 is at least 30%.

3. The glucoamylase variant of claim 1, wherein the variant is derived from the glucoamylase of SEQ ID NO: 2, and wherein the variant comprises a combination of specific substitutions selected from the group consisting of:
V18M+T43K+S95P+A121P+Q318Y+A518K+N527M+ T549W;
V18M+T43K+S95P+A121P+A518K+N527M+T549W;
T43K+S95P+A121P+Q318Y+A493V+A518K+ N527M+T549W;
V18M+T43K+S95P+A121P+Y295W+A518K+N527M+ T549W;
T43K+S95P+A121P+Q318Y+N527M+T549W;
V18M+T43K+S95P+A121P+Q318Y+N527M+T549W;
V18M+T43K+S95P+T116R+A121P+Q318Y+A493V+ N527M+T549W;
V18M+T43K+S95P+A121P+Q318Y+A493V+N527M+ T549W;
V18M+T43K+S95P+A121P+Q318Y+A493V+A518K+ N527M+T549W;
T43K+S95P+A121P+Q318Y+A518K+N527M+T549W;
V18M+T43K+S95P+T116R+A121P+Q318Y+N527M+ T549W;
T43K+S95P+A121P+Q318Y+A493V+N527M+T549W;

T43K+S95P+A121P+Y295W+Q318Y+A518K+ N527M+T549W;
V18M+T43K+S95P+T116R+A121P+Q318Y+A518K+ T549W;
V18M+T43K+S95P+A121P+Q318Y+A518K+N527M+ T549W;
T43K+S95P+A121P+Y295W+Q318Y+N527M+ T549W;
V18M+T43K+S95P+A121P+Q318Y+A518K+T549W;
S95P+A121P+Y295W+A493V+A518K+E520Q+ T549W;
S95P+A121P+Y295W+A518K+N527M+T549W;
S95P+A121P+Y295W+N527M+T549W;
S95P+A121P+A271F+Y295W+A518K+N527M+ T549W;
S95P+A121P+Y295W+S540K;
S95P+A121P+Y295W+S540R; and
S95P+A121P+Y295W+A518K+N527M;
and wherein the increase in raw starch hydrolytic activity compared to SEQ ID NO: 2 is at least 5%.

4. The glucoamylase variant of claim 1, wherein the variant is derived from a glucoamylase having a catalytic domain comprising amino acids 1-454 of SEQ ID NO: 2, a linker comprising amino acids 455-465 of SEQ ID NO: 4 and a starch binding domain comprising amino acids 466-559 of SEQ ID NO: 4, and wherein the variant comprises a substitution at one or more positions selected from the group consisting of:
T43K+S95P+G120S+A121P+Y295W+Q318Y+A518K+ N527M+T(V)549W;
S95P+G120S+A121P+Y295W+N539R+I541Y+T543V+ A545S+S546GCGV+G547S+S548T+T549A;
T43K+S95P+A121P+Y295W+Q318Y+N527M+T(V) 549W;
S95P+A121P+Y295W+T116R+N527M+T(V)549W;
T43K+S95P+A121P+Y295W+Q318Y+A518K+ N527M+T(V)549W;
S95P+A121P+Y295W+A117Q+N527M+T(V)549W;
S95P+T116R+A121P+Y295W+A518K+N527M+T(V) 549W;
V18M+T43K+S95P+A121P+Q318Y+A518K+T(V) 549W;
S95P+A121P+Y295W+Q318Y+N527M+T(V)549W;
S95P+G120S+A121P+Y295W+N527M+T(V)549W;
S95P+A121P+Y295W+A518K+N527M+T(V)549W;
S95P+N112L+A121P+Y295W+N527M+T(V)549W;
S95P+A121P+Y295W+N527M+T(V)549W;
S95P+G120S+A121P+Y295W+A518K+N527M+T(V) 549W;
S95P+N112L+A121P+Y295W+A518K+N527M+T(V) 549W;
S95P+A121P+Y295W+A518K+T(V)549W;
S95P+A121P+Y295W+A518K+N527M;
S95P+A121P+Y295W+S458C+N539R+I541Y+T543V+ A545S+S546GCGV+G547S+S548T+T549A;
S95P+A121P+Y295W+S458SGGC+N539R+I541Y+ T543V+A545S+S546GCGV+G547S+S548T+T549A;
T43K+S95P+A121P+Y295W+N527M+T(V)549W; and
S95P+A121P+Y295W+S458SCGG+N539R+I541Y+ T543V+A545S+S546GCGV+G547S+S548T+T549A;
and wherein the increase in raw starch hydrolytic activity compared to SEQ ID NO: 2 is at least 2%.

5. The glucoamylase variant of claim 1, wherein the number of substitutions or insertions are 1-20, e.g., 1-10 and 1-5, such as 1, 2, 3, 4, 5, 6, 7, 8, 9 or 10 substitutions or insertions.

6. A method for increasing raw starch hydrolysis activity of a glucoamylase comprising the steps:
(a) providing a hybrid glucoamylase comprising a first amino acid sequence consisting of amino acids 1-454 of SEQ ID NO: 2, a second amino acid sequence selected from amino acids 455-462 of SEQ ID NO: 2 or amino acids 455-465 of SEQ ID NO: 4, and a third amino acid sequence selected from amino acids 463-556 of SEQ ID NO: 2 or amino acids 466-559 of SEQ ID NO: 4; and/or
(b) introducing a substitution selected from the group consisting of: V18M, T43K, N112L, T116R, A117Q, G120S, A271F, Y295W, Q318Y; and/or
(c) Introducing at least three substitutions selected from the group consisting of: S458C, S458SCGG, S458SGGC, A493V, A518K, E520Q, N527M, S540K, R, S(G)546P, T(V)549W, N503R, N539R+I541Y+ T543V+A545S+S546GCGV+G547S+S548T+T549A.

7. A method for increasing raw starch hydrolysis activity of a glucoamylase comprising the steps:
(a) providing a hybrid glucoamylase comprising a first amino acid sequence consisting of amino acids 1-454 of SEQ ID NO: 2, a second amino acid sequence selected from amino acids 455-465 of SEQ ID NO: 4, and a third amino acid sequence selected from amino acids 466-559 of SEQ ID NO: 4; and/or
(b) introducing a substitution selected from the group consisting of: V18M, T43K, T116R, G120S, Y295W, Q318Y; and/or
(c) introducing a combination of alterations selected from the group consisting of: i) N539R+I541Y+T543V+ A545S+S546GCGV+G547S+S548T+T549A; ii) N539R+I541Y+T543V+A545S+S546PCGV+G547S+ S548T+T549A; iii) at least three substitutions selected from the group: S458SCGG, N527M, T(V)549W, and N503R.

8. A composition comprising the glucoamylase variant of claim 1.

9. A process of producing a fermentation product from starch-containing material comprising the steps of:
(a) liquefying starch-containing material in the presence of an alpha amylase;
(b) saccharifying the liquefied material; and
(c) fermenting with a fermenting organism;
wherein step (b) is carried out using at least a glucoamylase variant of claim 1.

10. The process of claim 9, wherein step (b) and step (c) are carried out simultaneously.

11. A process of producing a fermentation product from starch-containing material, comprising the steps of:
(a) saccharifying starch-containing material at a temperature below the initial gelatinization temperature of said starch-containing material; and
(b) fermenting with a fermenting organism,
wherein step (a) is carried out using at least a glucoamylase variant of claim 1.

12. A process of producing a syrup product from starch-containing material, comprising the step of:
(a) liquefying starch-containing material in the presence of an alpha amylase;
(b) saccharifying the liquefied material in the presence of a glucoamylase variant of claim 1.

13. The process of claim 9, wherein the fermenting organism is selected from a *Saccharomyces* spp. yeast.

14. The process of claim 13, wherein the yeast expresses a glucoamylase having at least 90% identity to SEQ ID NO: 2 or SEQ ID NO: 4.

15. A polynucleotide encoding the glucoamylase variant of claim 1.

16. A nucleic acid construct comprising the polynucleotide of claim 15.

17. An expression vector comprising the polynucleotide of claim 15.

18. A host cell comprising the polynucleotide of claim 15.

19. The process of claim 9, wherein a host cell is applied in the fermentation step, wherein the host cell comprises a polynucleotide encoding a glucoamylase variant having increased raw starch hydrolytic activity at pH=4.0, T=32° C., compared to the glucoamylase disclosed in SEQ ID NO: 2, wherein the variant is derived from a glucoamylase having a catalytic domain comprising amino acids 1-454 of SEQ ID NO: 2 or 1-454 of SEQ ID NO: 4, a linker comprising amino acids 455-462 of SEQ ID NO: 2 or amino acids 455-465 of SEQ ID NO: 4 and a starch binding domain comprising amino acids 463-556 of SEQ ID NO: 2 or amino acids 466-559 of SEQ ID NO: 4, and wherein the variant further comprises a substitution at one or more positions selected from the group consisting of:

V18M+T43K+S95P+A121P+Q318Y+A518K+N527M+T549W;
V18M+T43K+S95P+T116R+A121P+Q318Y+N539R+I541Y+T543V+A545S+S546PCGV+G547S+S548T+T549A;
S95P+A121P+Y295W+T116R+N539R+I541Y+T543V+A545S+S546PCGV+G547S+S548T+T549A;
T43K+S95P+A121P+Y295W+Q318Y+N539R+I541Y+T543V+A545S+S546PCGV+G547S+S548T+T549A;
T43K+S95P+G120S+A121P+Y295W+Q318Y+N539R+I541Y+T543V+A545S+S546GCGV+G547S+S548T+T549A;
V18M+T43K+S95P+T116R+A121P+Q318Y+S458SCGG+N527M+T(V)549W;
V18M+T43K+S95P+A121P+Q318Y+S458SCGG+N527M+T(V)549W+N503R;
V18M+T43K+S95P+A121P+Q318Y+N539R+I541Y+T543V+A545S+S546PCGV+G547S+S548T+T549A;
T43K+Q318Y+S95P+A121P+Y295W+S458SCGG+N527M+T(V)549W;
S95P+A121P+Y295W+G120S+N539R+I541Y+T543V+A545S+S546PCGV+G547S+S548T+T549A;
V18M+T43K+S95P+A121P+Q318Y+S458SCGG+N527M T(V)549W;
S95P+A121P+Y295W+N539R+I541Y+T543V+A545S+S546PCGV+G547S+S548T+T549A;
T43K+S95P+A121P+Y295W+Q318Y+N539R+I541Y+T543V+A545S+S546GCGV+G547S+S548T+T549A;
S95P+T116R+A121P+Y295W+N539R+I541Y+T543V+A545S+S546GCGV+G547S+S548T+T549A;
T43K+S95P+A121P+Y295W+Q318Y+N527M+T(V)549W+N503R;
S95P+A121P+Y295W+N539R+I541Y+T543V+A545S+S546GCGV+G547S+S548T+T549A;
V18M+T43K+S95P+A121P+A518K+N527M+T549W;
T43K+S95P+G120S+A121P+Y295W+Q318Y+A518K+N527M+T(V)549W;
T43K+S95P+A121P+Q318Y+A493V+A518K+N527M+T549W;
S95P+G120S+A121P+Y295W+N539R+I541Y+T543V+A545S+S546GCGV+G547S+S548T+T549A;
V18M+T43K+S95P+A121P+Y295W+A518K+N527M+T549W;
T43K+S95P+A121P+Y295W+Q318Y+N527M+T(V)549W;
T43K+S95P+A121P+Q318Y+N527M+T549W;
V18M+T43K+S95P+A121P+Q318Y+N527M+T549W;
S95P+A121P+Y295W+T116R+N527M+T(V)549W;
V18M+T43K+S95P+T116R+A121P+Q318Y+A493V+N527M+T549W;
V18M+T43K+S95P+A121P+Q318Y+A493V+N527M+T549W;
T43K+S95P+A121P+Y295W+Q318Y+A518K+N527M+T(V)549W;
S95P+A121P+Y295W+A117Q+N527M+T(V)549W;
V18M+T43K+S95P+A121P+Q318Y+A493V+A518K+N527M+T549W;
T43K+S95P+A121P+Q318Y+A518K+N527M+T549W;
V18M+T43K+S95P+T116R+A121P+Q318Y+N527M+T549W;
T43K+S95P+A121P+Q318Y+A493V+N527M+T549W;
S95P+T116R+A121P+Y295W+A518K+N527M+T(V)549W;
V18M+T43K+S95P+A121P+Q318Y+A518K+T(V)549W;
T43K+S95P+A121P+Y295W+Q318Y+A518K+N527M+T549W;
V18M+T43K+S95P+T116R+A121P+Q318Y+A518K+T549W;
S95P+A121P+Y295W+Q318Y+N527M+T(V)549W;
S95P+G120S+A121P+Y295W+N527M+T(V)549W;
S95P+A121P+Y295W+A518K+N527M+T(V)549W;
S95P+A121P+Y295W+N527M+T(V)549W;
S95P+N112L+A121P+Y295W+N527M+T(V)549W;
S95P+A121P+Y295W+N527M+T(V)549W;
V18M+T43K+S95P+A121P+Q318Y+A518K+N527M+T549W;
T43K+S95P+A121P+Y295W+Q318Y+N527M+T549W;
S95P+G120S+A121P+Y295W+A518K+N527M+T(V)549W;
S95P+N112L+A121P+Y295W+A518K+N527M+T(V)549W;
V18M+T43K+S95P+A121P+Q318Y+A518K+T549W;
S95P+A121P+Y295W+A493V+A518K+E520Q+T549W;
S95P+A121P+Y295W+A518K+N527M+T549W;
S95P+A121P+Y295W+A518K+T(V)549W;
S95P+A121P+Y295W+A518K+N527M;
S95P+A121P+Y295W+S458C+N539R+I541Y+T543V+A545S+S546GCGV+G547S+S548T+T549A;
S95P+A121P+Y295W+N527M+T549W;
S95P+A121P+A271F+Y295W+A518K+N527M+T549W;
S95P+A121P+Y295W+S540K;
S95P+A121P+Y295W+S540R;
S95P+A121P+Y295W+S458SGGC+N539R+I541Y+T543V+A545S+S546GCGV+G547S+S548T+T549A;
T43K+S95P+A121P+Y295W+N527M+T(V)549W; and
S95P+A121P+Y295W+S458SCGG+N539R+I541Y+T543V+A545S+S546GCGV+G547S+S548T+T549A;
 wherein the position numbering corresponds to amino acid positions in the amino acid sequence set forth in SEQ ID NO: 2; and wherein the variants have at least 85%, but less than 100%, sequence identity to the amino acid sequence of SEQ ID NO: 2.

20. A method of producing a glucoamylase variant, comprising:
(a) cultivating the host cell of claim 18 under conditions suitable for expression of the variant; and
(b) optionally recovering the variant.

21. The process of claim 11, wherein a host cell is applied in the fermentation step, wherein the host cell comprises a polynucleotide encoding a glucoamylase variant having increased raw starch hydrolytic activity at pH=4.0, T=32° C., compared to the glucoamylase disclosed in SEQ ID NO: 2, wherein the variant is derived from a glucoamylase having a catalytic domain comprising amino acids 1-454 of SEQ ID NO: 2 or 1-454 of SEQ ID NO: 4, a linker comprising amino acids 455-462 of SEQ ID NO: 2 or amino acids 455-465 of SEQ ID NO: 4 and a starch binding domain comprising amino acids 463-556 of SEQ ID NO: 2 or amino acids 466-559 of SEQ ID NO: 4, and wherein the variant further comprises a substitution at one or more positions selected from the group consisting of:

V18M+T43K+S95P+A121P+Q318Y+A518K+N527M+T549W;

V18M+T43K+S95P+T116R+A121P+Q318Y+N539R+I541Y+T543V+A545S+S546PCGV+G547S+S548T+T549A;

S95P+A121P+Y295W+T116R+N539R+I541Y+T543V+A545S+S546PCGV+G547S+S548T+T549A;

T43K+S95P+A121P+Y295W+Q318Y+N539R+I541Y+T543V+A545S+S546PCGV+G547S+S548T+T549A;

T43K+S95P+G120S+A121P+Y295W+Q318Y+N539R+I541Y+T543V+A545S+S546GCGV+G547S+S548T+T549A;

V18M+T43K+S95P+T116R+A121P+Q318Y+S458SCGG+N527M+T(V)549W;

V18M+T43K+S95P+A121P+Q318Y+S458SCGG+N527M+T(V)549W+N503R;

V18M+T43K+S95P+A121P+Q318Y+N539R+I541Y+T543V+A545S+S546PCGV+G547S+S548T+T549A;

T43K+Q318Y+S95P+A121P+Y295W+S458SCGG+N527M+T(V)549W;

S95P+A121P+Y295W+G120S+N539R+I541Y+T543V+A545S+S546PCGV+G547S+S548T+T549A;

V18M+T43K+S95P+A121P+Q318Y+S458SCGG+N527M T(V)549W;

S95P+A121P+Y295W+N539R+I541Y+T543V+A545S+S546PCGV+G547S+S548T+T549A;

T43K+S95P+A121P+Y295W+Q318Y+N539R+I541Y+T543V+A545S+S546GCGV+G547S+S548T+T549A;

S95P+T116R+A121P+Y295W+N539R+I541Y+T543V+A545S+S546GCGV+G547S+S548T+T549A;

T43K+S95P+A121P+Y295W+Q318Y+N527M+T(V)549W+N503R;

S95P+A121P+Y295W+N539R+I541Y+T543V+A545S+S546GCGV+G547S+S548T+T549A;

V18M+T43K+S95P+A121P+A518K+N527M+T549W;

T43K+S95P+G120S+A121P+Y295W+Q318Y+A518K+N527M+T(V)549W;

T43K+S95P+A121P+Q318Y+A493V+A518K+N527M+T549W;

S95P+G120S+A121P+Y295W+N539R+I541Y+T543V+A545S+S546GCGV+G547S+S548T+T549A;

V18M+T43K+S95P+A121P+Y295W+A518K+N527M+T549W;

T43K+S95P+A121P+Y295W+Q318Y+N527M+T(V)549W;

T43K+S95P+A121P+Q318Y+N527M+T549W;

V18M+T43K+S95P+A121P+Q318Y+N527M+T549W;

S95P+A121P+Y295W+T116R+N527M+T(V)549W;

V18M+T43K+S95P+T116R+A121P+Q318Y+A493V+N527M+T549W;

V18M+T43K+S95P+A121P+Q318Y+A493V+N527M+T549W;

T43K+S95P+A121P+Y295W+Q318Y+A518K+N527M+T(V)549W;

S95P+A121P+Y295W+A117Q+N527M+T(V)549W;

V18M+T43K+S95P+A121P+Q318Y+A493V+A518K+N527M+T549W;

T43K+S95P+A121P+Q318Y+A518K+N527M+T549W;

V18M+T43K+S95P+T116R+A121P+Q318Y+N527M+T549W;

T43K+S95P+A121P+Q318Y+A493V+N527M+T549W;

S95P+T116R+A121P+Y295W+A518K+N527M+T(V)549W;

V18M+T43K+S95P+A121P+Q318Y+A518K+T(V)549W;

T43K+S95P+A121P+Y295W+Q318Y+A518K+N527M+T549W;

V18M+T43K+S95P+T116R+A121P+Q318Y+A518K+T549W;

S95P+A121P+Y295W+Q318Y+N527M+T(V)549W;

S95P+G120S+A121P+Y295W+N527M+T(V)549W;

S95P+A121P+Y295W+A518K+N527M+T(V)549W;

S95P+A121P+Y295W+N527M+T(V)549W;

S95P+N112L+A121P+Y295W+N527M+T(V)549W;

S95P+A121P+Y295W+N527M+T(V)549W;

V18M+T43K+S95P+A121P+Q318Y+A518K+N527M+T549W;

T43K+S95P+A121P+Y295W+Q318Y+N527M+T549W;

S95P+G120S+A121P+Y295W+A518K+N527M+T(V)549W;

S95P+N112L+A121P+Y295W+A518K+N527M+T(V)549W;

V18M+T43K+S95P+A121P+Q318Y+A518K+T549W;

S95P+A121P+Y295W+A493V+A518K+E520Q+T549W;

S95P+A121P+Y295W+A518K+N527M+T549W;

S95P+A121P+Y295W+A518K+T(V)549W;

S95P+A121P+Y295W+A518K+N527M;

S95P+A121P+Y295W+S458C+N539R+I541Y+T543V+A545S+S546GCGV+G547S+S548T+T549A;

S95P+A121P+Y295W+N527M+T549W;

S95P+A121P+A271F+Y295W+A518K+N527M+T549W;

S95P+A121P+Y295W+S540K;

S95P+A121P+Y295W+S540R;

S95P+A121P+Y295W+S458SGGC+N539R+I541Y+T543V+A545S+S546GCGV+G547S+S548T+T549A;

T43K+S95P+A121P+Y295W+N527M+T(V)549W; and

S95P+A121P+Y295W+S458SCGG+N539R+I541Y+T543V+A545S+S546GCGV+G547S+S548T+T549A;

wherein the position numbering corresponds to amino acid positions in the amino acid sequence set forth in SEQ ID NO: 2; and wherein the variants have at least 85%, but less than 100%, sequence identity to the amino acid sequence of SEQ ID NO: 2.

* * * * *

SEQUENCE LISTING

<160> NUMBER OF SEQ ID NOS: 10

<210> SEQ ID NO 1
<211> LENGTH: 1722
<212> TYPE: DNA
<213> ORGANISM: Gloeophyllum sepiarium

<400> SEQUENCE: 1

```
atgtaccgct tccttgtctg tgcgctgggg cttgcggcat cagttctcgc ccagtcggtc      60
gacagctatg ttagcagcga aggtcccata gccaaggcgg gcgtccttgc taacattggg     120
ccgaacggct ccaaggcctc tggcgcatcc gctggtgttg tggtcgcgag ccctagcacg     180
tcggaccccg actattggta cacttggacg cgtgactcgt ccctcgtatt caagtcactt     240
attgaccagt acaccaccgg catcgacagc acgagctctc tgaggactct catcgacgat     300
ttcgtaactg ccgaggctaa tctccagcaa gtctctaacc ctagtggtac cctcaccacc     360
ggtggcttgg gagagcccaa gttcaacgtc gacgaaactg catttactgg tgcatgggqt     420 cgaccccaac gcgacggacc tgccctccgc tcgactgcat tgatcacgta cggtaactgg     480
ctgttgtcca acggaaatac gagctatgtt acgagcaatc tgtggccgat catccagaac     540
gaccttggtt atgtcgtgtc atactggaac cagtctacct acgacctctg ggaggaagta     600
gactcgtcat cgttcttcac tactgcagta cagcaccgtg ctctccgtga aggtgcggcc     660
```

```
ttcgctaccg ccatcggtca gacttcgcag gtcagcagct atacgactca ggcggacaat      720
cttctgtgct tcttgcagtc ttactggaac ccgagcggtg gttacatcac tgctaacact      780
ggcggcggcc gttccggcaa ggatgccaac acacttctgg catccattca cacgtacgac      840
cccagcgcgg gctgcgacgc tgcgactttc cagccctgct ctgacaaggc actgtcgaac      900
ctgaaggtct acgtcgactc tttccgctcg gtctactcca tcaacagtgg tgtcgcctct      960
aacgctgccg tcgccacggg tcgttatccc gaggatagcc accagggtgg aaacccttgg     1020
tacctcacca catttgcggt cgccgagcaa ctctatgatg ctctcaatgt ctgggagtcg     1080
cagggttccc tcgaggtcac ctccacctcc cttgccttct ccagcagtt ctcatccggc      1140 gtcactgctg gcacctactc ttctagctcc agcacataca gcaccctcac gtctgccatc     1200
aagaactttg ccgatggatt tgtcgctatc aatgctaagt acacgccatc caacggtggc     1260
ctggcggaac aatacagcaa gagcgacggt tctcccctta gcgcggtgga cttgacgtgg     1320
agctacgctt cggctttgac ggcgtttgaa gcaaggaaca atactcagtt cgccggctgg     1380
ggcgctgcag gcctgactgt gccttcctct tgctccggca actctggtgg gccgaccgtt     1440
gctgtcacat tcaacgtgaa cgccgagact gtgtggggag agaacatcta tcttactggt     1500
tccgtcgatg ctctggagaa ctggtcggcc gacaatgccc tcctgctctc atcggctaat     1560
tacccgacct ggagtatcac cgtcaacttg ccggcgagca ctgctattga gtacaagtac     1620
atccgcaaaa ataatggggc cgttacctgg gagtcagacc ccaacaatag catcactact     1680
ccggccagcg gctcgacgac cgagaatgac acttggcgtt ga                        1722

<210> SEQ ID NO 2
<211> LENGTH: 556
<212> TYPE: PRT
<213> ORGANISM: Gloeophyllum sepiarium

<400> SEQUENCE: 2

Gln Ser Val Asp Ser Tyr Val Ser Glu Gly Pro Ile Ala Lys Ala
1               5                   10                  15

Gly Val Leu Ala Asn Ile Gly Pro Asn Gly Ser Lys Ala Ser Gly Ala
            20                  25                  30

Ser Ala Gly Val Val Val Ala Ser Pro Ser Thr Ser Asp Pro Asp Tyr
        35                  40                  45

Trp Tyr Thr Trp Thr Arg Asp Ser Ser Leu Val Phe Lys Ser Leu Ile
    50                  55                  60

Asp Gln Tyr Thr Thr Gly Ile Asp Ser Thr Ser Ser Leu Arg Thr Leu
65                  70                  75                  80

Ile Asp Asp Phe Val Thr Ala Glu Ala Asn Leu Gln Gln Val Ser Asn
                85                  90                  95

Pro Ser Gly Thr Leu Thr Thr Gly Gly Leu Gly Glu Pro Lys Phe Asn
            100                 105                 110

Val Asp Glu Thr Ala Phe Thr Gly Ala Trp Gly Arg Pro Gln Arg Asp
        115                 120                 125

Gly Pro Ala Leu Arg Ser Thr Ala Leu Ile Thr Tyr Gly Asn Trp Leu
    130                 135                 140

Leu Ser Asn Gly Asn Thr Ser Tyr Val Thr Asn Leu Trp Pro Ile
145                 150                 155                 160

Ile Gln Asn Asp Leu Gly Tyr Val Val Ser Tyr Trp Asn Gln Ser Thr
                165                 170                 175

Tyr Asp Leu Trp Glu Glu Val Asp Ser Ser Ser Phe Phe Thr Thr Ala
```

180                 185                 190
    Val Gln His Arg Ala Leu Arg Glu Gly Ala Ala Phe Ala Thr Ala Ile
                195                 200                 205

Gly Gln Thr Ser Gln Val Ser Ser Tyr Thr Thr Gln Ala Asp Asn Leu
        210                 215                 220

Leu Cys Phe Leu Gln Ser Tyr Trp Asn Pro Ser Gly Gly Tyr Ile Thr
    225                 230                 235                 240

Ala Asn Thr Gly Gly Arg Ser Gly Lys Asp Ala Asn Thr Leu Leu
                    245                 250                 255

Ala Ser Ile His Thr Tyr Asp Pro Ser Ala Gly Cys Asp Ala Ala Thr
                260                 265                 270

Phe Gln Pro Cys Ser Asp Lys Ala Leu Ser Asn Leu Lys Val Tyr Val
                275                 280                 285

Asp Ser Phe Arg Ser Val Tyr Ser Ile Asn Ser Gly Val Ala Ser Asn
            290                 295                 300

Ala Ala Val Ala Thr Gly Arg Tyr Pro Glu Asp Ser Tyr Gln Gly Gly
    305                 310                 315                 320

Asn Pro Trp Tyr Leu Thr Thr Phe Ala Val Ala Glu Gln Leu Tyr Asp
                    325                 330                 335

Ala Leu Asn Val Trp Glu Ser Gln Gly Ser Leu Glu Val Thr Ser Thr
                340                 345                 350

Ser Leu Ala Phe Phe Gln Gln Phe Ser Ser Gly Val Thr Ala Gly Thr
                355                 360                 365

Tyr Ser Ser Ser Ser Ser Thr Tyr Ser Thr Leu Thr Ser Ala Ile Lys
            370                 375                 380

Asn Phe Ala Asp Gly Phe Val Ala Ile Asn Ala Lys Tyr Thr Pro Ser
    385                 390                 395                 400

Asn Gly Gly Leu Ala Glu Gln Tyr Ser Lys Ser Asp Gly Ser Pro Leu
                    405                 410                 415

Ser Ala Val Asp Leu Thr Trp Ser Tyr Ala Ser Ala Leu Thr Ala Phe
                420                 425                 430

Glu Ala Arg Asn Asn Thr Gln Phe Ala Gly Trp Gly Ala Ala Gly Leu
                435                 440                 445

Thr Val Pro Ser Ser Cys Ser Gly Asn Ser Gly Gly Pro Thr Val Ala
                450                 455                 460

Val Thr Phe Asn Val Asn Ala Glu Thr Val Trp Gly Glu Asn Ile Tyr
    465                 470                 475                 480

Leu Thr Gly Ser Val Asp Ala Leu Glu Asn Trp Ser Ala Asp Asn Ala
                    485                 490                 495

Leu Leu Leu Ser Ser Ala Asn Tyr Pro Thr Trp Ser Ile Thr Val Asn
                500                 505                 510

Leu Pro Ala Ser Thr Ala Ile Glu Tyr Lys Tyr Ile Arg Lys Asn Asn
                515                 520                 525

Gly Ala Val Thr Trp Glu Ser Asp Pro Asn Asn Ser Ile Thr Thr Pro
                530                 535                 540

Ala Ser Gly Ser Thr Thr Glu Asn Asp Thr Trp Arg
    545                 550                 555

<210> SEQ ID NO 3
<211> LENGTH: 1731
<212> TYPE: DNA
<213> ORGANISM: Gloeophyllum trabeum

<400> SEQUENCE: 3

-continued

| | |
|---|---|
| atgtaccgct tccttgtctg tgctctcggg cttctgggga cagtcctcgc tcagtcagtc | 60 |
| gacagttatg tcggcagcga aggccccata gcaaaggccg cgtccttgc caacattggg | 120 |
| ccgaacggct caaaggcctc tggtgcagcc gccggcgtgg tggtggctag ccccagcaag | 180 |
| tcggatcccg actattggta cacttggacg cgtgactcgt cactcgtttt caagtctctc | 240 |
| attgatcagt acaccactgg tatcgacagc acgagttcgt tgaggtctct gatagacagt | 300 |
| ttcgttattg ccgaggccaa cattcagcag gtctctaatc ccagcggcac tcttactacc | 360 |
| ggcggcttgg gagagccaaa attcaatgtc gatgaaactg cattcaccgg tgcatggggt | 420 |
| cgacccagc gcgacggacc tgcgctccgt gcgactgctt tgatcaccta cggtaactgg | 480 |
| ctcttgtcaa acgggaacac gacctgggtt accagtacgc tgtggccgat catccagaac | 540 |
| gatctcaact acgtcgttca gtactggaac cagaccacct tcgacctctg gaagaagtg | 600 |
| aactcttcct cgttcttcac cactgcagtg cagcaccgtg ccttgcgcga aggcgcagca | 660 |
| ttcgctacca agatcggtca gacctcctcg gtcagcagtc acacaaccca agcggcgaat | 720 |
| ctactttgct ttttgcagtc ttactggaac cccacttccg gatatatcac cgctaacact | 780 |
| ggcggtggtc ggtccggcaa ggacgccaac accctcttgg catccatcca cacttacgac | 840 |
| cccagcgcgg gctgcgatgc cacgaccttc agccctgct ccgacaaagc cctctcgaat | 900 |
| ctgaaggttt acgtcgactc cttccgttct gtctactcca tcaacagcgg tattgcctct | 960 |
| aacgccgctc tcgccactgg tcgctacccg gaagacagtc accagggcgg gaacccatgg | 1020 |
| tacctcacta cgttcgccgt cgccgagcag ctctatgacg ccctcaatgt ctgggctgct | 1080 |
| cagggctccc tcaatgtcac ctccatctcc ctccccttct tccagcagtt ctcctctagt | 1140 |
| gtcactgccg gcacttacgc ttcgagctcc accacttaca cgactctgac ctccgccatt | 1200 |
| aagagcttcg cggatggatt cgtcgctatc aacgcccagt acacgccgtc caacggtggc | 1260 |
| ctcgctgagc agttcagcag gagcaacggc gctcccgtca gcgctgttga tttgacatgg | 1320 |
| agctatgcat ctgcattgac cgcgtttgaa gcgaggaata atactcagtt cgccggctgg | 1380 |
| ggcgcggtag gtttgactgt gccgacctcg tgctccagca acagtggtgg aggcggagga | 1440 |
| tcgactgtcg ccgtgacgtt caacgtgaac gcccaaacgg tttggggcga aaacatctac | 1500 |
| atcactggct cggttgacgc tctgagtaac tggtctcccg caacgccct cttgctctcg | 1560 |
| tctgccaact acccgacctg gagcattacc gtgaatttac ccgcgagcac tgccattcag | 1620 |
| tataagtata tccgcaagaa caacggagct gtcacctggg aatccgatcc caacaacagc | 1680 |
| ataactactc cagccagcgg ctccgtgacc gagaatgaca cttggcgtta a | 1731 |

<210> SEQ ID NO 4
<211> LENGTH: 559
<212> TYPE: PRT
<213> ORGANISM: Gloeophyllum trabeum

<400> SEQUENCE: 4

Gln Ser Val Asp Ser Tyr Val Gly Ser Glu Gly Pro Ile Ala Lys Ala
1               5                   10                  15

Gly Val Leu Ala Asn Ile Gly Pro Asn Gly Ser Lys Ala Ser Gly Ala
            20                  25                  30

Ala Ala Gly Val Val Ala Ser Pro Ser Lys Ser Asp Pro Asp Tyr
        35                  40                  45

Trp Tyr Thr Trp Thr Arg Asp Ser Ser Leu Val Phe Lys Ser Leu Ile
    50                  55                  60

Asp Gln Tyr Thr Thr Gly Ile Asp Ser Thr Ser Ser Leu Arg Ser Leu

```
                65                    70                    75                    80
        Ile Asp Ser Phe Val Ile Ala Glu Ala Asn Ile Gln Gln Val Ser Asn
                            85                    90                    95
        Pro Ser Gly Thr Leu Thr Thr Gly Gly Leu Gly Glu Pro Lys Phe Asn
                           100                   105                   110
        Val Asp Glu Thr Ala Phe Thr Gly Ala Trp Gly Arg Pro Gln Arg Asp
                           115                   120                   125
        Gly Pro Ala Leu Arg Ala Thr Ala Leu Ile Thr Tyr Gly Asn Trp Leu
                           130                   135                   140
        Leu Ser Asn Gly Asn Thr Thr Trp Val Thr Ser Thr Leu Trp Pro Ile
        145                   150                   155                   160
        Ile Gln Asn Asp Leu Asn Tyr Val Val Gln Tyr Trp Asn Gln Thr Thr
                           165                   170                   175
        Phe Asp Leu Trp Glu Glu Val Asn Ser Ser Phe Phe Thr Thr Ala
                           180                   185                   190
        Val Gln His Arg Ala Leu Arg Glu Gly Ala Ala Phe Ala Thr Lys Ile
                           195                   200                   205
        Gly Gln Thr Ser Ser Val Ser Ser Tyr Thr Thr Gln Ala Ala Asn Leu
                           210                   215                   220
        Leu Cys Phe Leu Gln Ser Tyr Trp Asn Pro Thr Ser Gly Tyr Ile Thr
        225                   230                   235                   240
        Ala Asn Thr Gly Gly Gly Arg Ser Gly Lys Asp Ala Asn Thr Leu Leu
                           245                   250                   255
        Ala Ser Ile His Thr Tyr Asp Pro Ser Ala Gly Cys Asp Ala Thr Thr
                           260                   265                   270
        Phe Gln Pro Cys Ser Asp Lys Ala Leu Ser Asn Leu Lys Val Tyr Val
                           275                   280                   285
        Asp Ser Phe Arg Ser Val Tyr Ser Ile Asn Ser Gly Ile Ala Ser Asn
                           290                   295                   300
        Ala Ala Val Ala Thr Gly Arg Tyr Pro Glu Asp Ser Tyr Gln Gly Gly
        305                   310                   315                   320
        Asn Pro Trp Tyr Leu Thr Thr Phe Ala Val Ala Glu Gln Leu Tyr Asp
                           325                   330                   335
        Ala Leu Asn Val Trp Ala Ala Gln Gly Ser Leu Asn Val Thr Ser Ile
                           340                   345                   350
        Ser Leu Pro Phe Phe Gln Gln Phe Ser Ser Ser Val Thr Ala Gly Thr
                           355                   360                   365
        Tyr Ala Ser Ser Ser Thr Thr Tyr Thr Thr Leu Thr Ser Ala Ile Lys
                           370                   375                   380
        Ser Phe Ala Asp Gly Phe Val Ala Ile Asn Ala Gln Tyr Thr Pro Ser
        385                   390                   395                   400
        Asn Gly Gly Leu Ala Glu Gln Phe Ser Arg Ser Asn Gly Ala Pro Val
                           405                   410                   415
        Ser Ala Val Asp Leu Thr Trp Ser Tyr Ala Ser Ala Leu Thr Ala Phe
                           420                   425                   430
        Glu Ala Arg Asn Asn Thr Gln Phe Ala Gly Trp Gly Ala Val Gly Leu
                           435                   440                   445
        Thr Val Pro Thr Ser Cys Ser Ser Asn Ser Gly Gly Gly Gly Gly Ser
                           450                   455                   460
        Thr Val Ala Val Thr Phe Asn Val Asn Ala Gln Thr Val Trp Gly Glu
        465                   470                   475                   480
        Asn Ile Tyr Ile Thr Gly Ser Val Asp Ala Leu Ser Asn Trp Ser Pro
                           485                   490                   495
```

```
Asp Asn Ala Leu Leu Ser Ser Ala Asn Tyr Pro Thr Trp Ser Ile
            500                 505                 510

Thr Val Asn Leu Pro Ala Ser Thr Ala Ile Gln Tyr Lys Tyr Ile Arg
            515                 520                 525

Lys Asn Asn Gly Ala Val Thr Trp Glu Ser Asp Pro Asn Asn Ser Ile
530                 535                 540

Thr Thr Pro Ala Ser Gly Ser Val Thr Glu Asn Asp Thr Trp Arg
545                 550                 555

<210> SEQ ID NO 5
<211> LENGTH: 583
<212> TYPE: PRT
<213> ORGANISM: Artificial
<220> FEATURE:
<223> OTHER INFORMATION: Hybrid alpha amylase having catalytic core from
      Rhizomucor pusillus

<400> SEQUENCE: 5

Ala Thr Ser Asp Asp Trp Lys Gly Lys Ala Ile Tyr Gln Leu Leu Thr
1               5                   10                  15

Asp Arg Phe Gly Arg Ala Asp Asp Ser Thr Ser Asn Cys Ser Asn Leu
            20                  25                  30

Ser Asn Tyr Cys Gly Gly Thr Tyr Glu Gly Ile Thr Lys His Leu Asp
        35                  40                  45

Tyr Ile Ser Gly Met Gly Phe Asp Ala Ile Trp Ile Ser Pro Ile Pro
    50                  55                  60

Lys Asn Ser Asp Gly Gly Tyr His Gly Tyr Trp Ala Thr Asp Phe Tyr
65                  70                  75                  80

Gln Leu Asn Ser Asn Phe Gly Asp Glu Ser Gln Leu Lys Ala Leu Ile
                85                  90                  95

Gln Ala Ala His Glu Arg Asp Met Tyr Val Met Leu Asp Val Val Ala
            100                 105                 110

Asn His Ala Gly Pro Thr Ser Asn Gly Tyr Ser Gly Tyr Thr Phe Gly
        115                 120                 125

Asp Ala Ser Leu Tyr His Pro Lys Cys Thr Ile Asp Tyr Asn Asp Gln
    130                 135                 140

Thr Ser Ile Glu Gln Cys Trp Val Ala Asp Glu Leu Pro Asp Ile Asp
145                 150                 155                 160

Thr Glu Asn Ser Asp Asn Val Ala Ile Leu Asn Asp Ile Val Ser Gly
                165                 170                 175

Trp Val Gly Asn Tyr Ser Phe Asp Gly Ile Arg Ile Asp Thr Val Lys
            180                 185                 190

His Ile Arg Lys Asp Phe Trp Thr Gly Tyr Ala Glu Ala Gly Val
        195                 200                 205

Phe Ala Thr Gly Glu Val Phe Asn Gly Asp Pro Ala Tyr Val Gly Pro
    210                 215                 220

Tyr Gln Lys Tyr Leu Pro Ser Leu Ile Asn Tyr Pro Met Tyr Tyr Ala
225                 230                 235                 240

Leu Asn Asp Val Phe Val Ser Lys Ser Lys Gly Phe Ser Arg Ile Ser
                245                 250                 255

Glu Met Leu Gly Ser Asn Arg Asn Ala Phe Glu Asp Thr Ser Val Leu
            260                 265                 270

Thr Thr Phe Val Asp Asn His Asp Asn Pro Arg Phe Leu Asn Ser Gln
        275                 280                 285

Ser Asp Lys Ala Leu Phe Lys Asn Ala Leu Thr Tyr Val Leu Leu Gly
```

```
            290                 295                 300
Glu Gly Ile Pro Ile Val Tyr Tyr Gly Ser Glu Gln Gly Phe Ser Gly
305                 310                 315                 320

Gly Ala Asp Pro Ala Asn Arg Glu Val Leu Trp Thr Thr Asn Tyr Asp
                325                 330                 335

Thr Ser Ser Asp Leu Tyr Gln Phe Ile Lys Thr Val Asn Ser Val Arg
            340                 345                 350

Met Lys Ser Asn Lys Ala Val Tyr Met Asp Ile Tyr Val Gly Asp Asn
        355                 360                 365

Ala Tyr Ala Phe Lys His Gly Asp Ala Leu Val Val Leu Asn Asn Tyr
    370                 375                 380

Gly Ser Gly Ser Thr Asn Gln Val Ser Phe Ser Val Ser Gly Lys Phe
385                 390                 395                 400

Asp Ser Gly Ala Ser Leu Met Asp Ile Val Ser Asn Ile Thr Thr Thr
                405                 410                 415

Val Ser Ser Asp Gly Thr Val Thr Phe Asn Leu Lys Asp Gly Leu Pro
            420                 425                 430

Ala Ile Phe Thr Ser Ala Thr Gly Gly Thr Thr Thr Ala Thr Pro
        435                 440                 445

Thr Gly Ser Gly Ser Val Thr Ser Thr Ser Lys Thr Thr Ala Thr Ala
450                 455                 460

Ser Lys Thr Ser Thr Ser Thr Ser Thr Ser Cys Thr Thr Pro Thr
465                 470                 475                 480

Ala Val Ala Val Thr Phe Asp Leu Thr Ala Thr Thr Thr Tyr Gly Glu
                485                 490                 495

Asn Ile Tyr Leu Val Gly Ser Ile Ser Gln Leu Gly Asp Trp Glu Thr
            500                 505                 510

Ser Asp Gly Ile Ala Leu Ser Ala Asp Lys Tyr Thr Ser Ser Asp Pro
        515                 520                 525

Leu Trp Tyr Val Thr Val Thr Leu Pro Ala Gly Glu Ser Phe Glu Tyr
    530                 535                 540

Lys Phe Ile Arg Ile Glu Ser Asp Asp Ser Val Glu Trp Glu Ser Asp
545                 550                 555                 560

Pro Asn Arg Glu Tyr Thr Val Pro Gln Ala Cys Gly Thr Ser Thr Ala
                565                 570                 575

Thr Val Asp Thr Trp Arg
            580

<210> SEQ ID NO 6
<211> LENGTH: 583
<212> TYPE: PRT
<213> ORGANISM: Artificial
<220> FEATURE:
<223> OTHER INFORMATION: Variant alpha amylase

<400> SEQUENCE: 6

Ala Thr Ser Asp Asp Trp Lys Gly Lys Ala Ile Tyr Gln Leu Leu Thr
1               5                   10                  15

Asp Arg Phe Gly Arg Ala Asp Asp Ser Thr Ser Asn Cys Ser Asn Leu
            20                  25                  30

Ser Asn Tyr Cys Gly Gly Thr Tyr Glu Gly Ile Thr Lys His Leu Asp
        35                  40                  45

Tyr Ile Ser Gly Met Gly Phe Asp Ala Ile Trp Ile Ser Pro Ile Pro
    50                  55                  60

Lys Asn Ser Asp Gly Gly Tyr His Gly Tyr Trp Ala Thr Asp Phe Tyr
```

```
               65                  70                  75                  80

Gln Leu Asn Ser Asn Phe Gly Asp Glu Ser Gln Leu Lys Ala Leu Ile
                    85                  90                  95

Gln Ala Ala His Glu Arg Asp Met Tyr Val Met Leu Asp Val Val Ala
                100                 105                 110

Asn His Ala Gly Pro Thr Ser Asn Gly Tyr Ser Gly Tyr Thr Phe Asp
                115                 120                 125

Asp Ala Ser Leu Tyr His Pro Lys Cys Thr Ile Asp Tyr Asn Asn Gln
130                 135                 140

Thr Ser Ile Glu Gln Cys Trp Val Ala Asp Glu Leu Pro Asp Ile Asp
145                 150                 155                 160

Thr Glu Asn Ser Asp Asn Val Ala Ile Leu Asn Asp Ile Val Ser Gly
                165                 170                 175

Trp Val Gly Asn Tyr Ser Phe Asp Gly Ile Arg Ile Asp Thr Val Lys
                180                 185                 190

His Ile Arg Lys Asp Phe Trp Thr Gly Tyr Ala Glu Ala Ala Gly Val
            195                 200                 205

Phe Ala Thr Gly Glu Val Phe Asn Gly Asp Pro Ala Tyr Val Gly Pro
210                 215                 220

Tyr Gln Lys Tyr Leu Pro Ser Leu Ile Asn Tyr Pro Met Tyr Tyr Ala
225                 230                 235                 240

Leu Asn Asp Val Phe Val Ser Lys Ser Lys Gly Phe Ser Arg Ile Ser
                245                 250                 255

Glu Met Leu Gly Ser Asn Arg Asn Ala Phe Glu Asp Thr Ser Val Leu
                260                 265                 270

Thr Thr Phe Val Asp Asn His Asp Asn Pro Arg Phe Leu Asn Ser Gln
            275                 280                 285

Ser Asp Lys Ala Leu Phe Lys Asn Ala Leu Thr Tyr Val Leu Leu Gly
        290                 295                 300

Glu Gly Ile Pro Ile Val Tyr Tyr Gly Ser Glu Gln Gly Phe Ser Gly
305                 310                 315                 320

Gly Ala Asp Pro Ala Asn Arg Glu Val Leu Trp Thr Thr Asn Tyr Asp
                325                 330                 335

Thr Ser Ser Asp Leu Tyr Gln Phe Ile Lys Thr Val Asn Ser Val Arg
                340                 345                 350

Met Lys Ser Asn Lys Ala Val Tyr Met Asp Ile Tyr Val Gly Asp Asn
            355                 360                 365

Ala Tyr Ala Phe Lys His Gly Asp Ala Leu Val Val Leu Asn Asn Tyr
370                 375                 380

Gly Ser Gly Ser Thr Asn Gln Val Ser Phe Ser Val Ser Gly Lys Phe
385                 390                 395                 400

Asp Ser Gly Ala Ser Leu Met Asp Ile Val Ser Asn Ile Thr Thr Thr
                405                 410                 415

Val Ser Ser Asp Gly Thr Val Thr Phe Asn Leu Lys Asp Gly Leu Pro
                420                 425                 430

Ala Ile Phe Thr Ser Ala Thr Gly Gly Thr Thr Thr Ala Thr Pro
            435                 440                 445

Thr Gly Ser Gly Ser Val Thr Ser Thr Ser Lys Thr Thr Ala Thr Ala
450                 455                 460

Ser Lys Thr Ser Thr Ser Thr Ser Ser Thr Ser Cys Thr Thr Pro Thr
465                 470                 475                 480

Ala Val Ala Val Thr Phe Asp Leu Thr Ala Thr Thr Thr Tyr Gly Glu
                485                 490                 495
```

```
Asn Ile Tyr Leu Val Gly Ser Ile Ser Gln Leu Gly Asp Trp Glu Thr
                500                 505                 510

Ser Asp Gly Ile Ala Leu Ser Ala Asp Lys Tyr Thr Ser Ser Asp Pro
            515                 520                 525

Leu Trp Tyr Val Thr Val Thr Leu Pro Ala Gly Glu Ser Phe Glu Tyr
        530                 535                 540

Lys Phe Ile Arg Ile Glu Ser Asp Ser Val Glu Trp Glu Ser Asp
545                 550                 555                 560

Pro Asn Arg Glu Tyr Thr Val Pro Gln Ala Cys Gly Thr Ser Thr Ala
                565                 570                 575

Thr Val Thr Asp Thr Trp Arg
                580

<210> SEQ ID NO 7
<211> LENGTH: 412
<212> TYPE: PRT
<213> ORGANISM: Pyrococcus furiosus

<400> SEQUENCE: 7

Ala Glu Leu Glu Gly Leu Asp Glu Ser Ala Ala Gln Val Met Ala Thr
1               5                   10                  15

Tyr Val Trp Asn Leu Gly Tyr Asp Gly Ser Gly Ile Thr Ile Gly Ile
            20                  25                  30

Ile Asp Thr Gly Ile Asp Ala Ser His Pro Asp Leu Gln Gly Lys Val
        35                  40                  45

Ile Gly Trp Val Asp Phe Val Asn Gly Arg Ser Tyr Pro Tyr Asp Asp
    50                  55                  60

His Gly His Gly Thr His Val Ala Ser Ile Ala Ala Gly Thr Gly Ala
65                  70                  75                  80

Ala Ser Asn Gly Lys Tyr Lys Gly Met Ala Pro Gly Ala Lys Leu Ala
                85                  90                  95

Gly Ile Lys Val Leu Gly Ala Asp Gly Ser Gly Ser Ile Ser Thr Ile
            100                 105                 110

Ile Lys Gly Val Glu Trp Ala Val Asp Asn Lys Asp Lys Tyr Gly Ile
        115                 120                 125

Lys Val Ile Asn Leu Ser Leu Gly Ser Ser Gln Ser Ser Asp Gly Thr
    130                 135                 140

Asp Ala Leu Ser Gln Ala Val Asn Ala Ala Trp Asp Ala Gly Leu Val
145                 150                 155                 160

Val Val Val Ala Ala Gly Asn Ser Gly Pro Asn Lys Tyr Thr Ile Gly
                165                 170                 175

Ser Pro Ala Ala Ala Ser Lys Val Ile Thr Val Gly Ala Val Asp Lys
            180                 185                 190

Tyr Asp Val Ile Thr Ser Phe Ser Ser Arg Gly Pro Thr Ala Asp Gly
        195                 200                 205

Arg Leu Lys Pro Glu Val Val Ala Pro Gly Asn Trp Ile Ile Ala Ala
    210                 215                 220

Arg Ala Ser Gly Thr Ser Met Gly Gln Pro Ile Asn Asp Tyr Tyr Thr
225                 230                 235                 240

Ala Ala Pro Gly Thr Ser Met Ala Thr Pro His Val Ala Gly Ile Ala
                245                 250                 255

Ala Leu Leu Leu Gln Ala His Pro Ser Trp Thr Pro Asp Lys Val Lys
            260                 265                 270

Thr Ala Leu Ile Glu Thr Ala Asp Ile Val Lys Pro Asp Glu Ile Ala
```

```
                275                 280                 285
Asp Ile Ala Tyr Gly Ala Gly Arg Val Asn Ala Tyr Lys Ala Ile Asn
290                 295                 300

Tyr Asp Asn Tyr Ala Lys Leu Val Phe Thr Gly Tyr Val Ala Asn Lys
305                 310                 315                 320

Gly Ser Gln Thr His Gln Phe Val Ile Ser Gly Ala Ser Phe Val Thr
                325                 330                 335

Ala Thr Leu Tyr Trp Asp Asn Ala Asn Ser Asp Leu Asp Leu Tyr Leu
                340                 345                 350

Tyr Asp Pro Asn Gly Asn Gln Val Asp Tyr Ser Tyr Thr Ala Tyr Tyr
                355                 360                 365

Asp Phe Glu Lys Val Gly Tyr Tyr Asn Pro Thr Asp Gly Thr Trp Thr
                370                 375                 380

Ile Lys Val Val Ser Tyr Ser Gly Ser Ala Asn Tyr Gln Val Asp Val
385                 390                 395                 400

Val Ser Asp Gly Ser Leu Ser Gln Pro Gly Ser Ser
                405                 410

<210> SEQ ID NO 8
<211> LENGTH: 515
<212> TYPE: PRT
<213> ORGANISM: Bacillus stearothermophillus

<400> SEQUENCE: 8

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
                20                  25                  30

Leu Ser Ser Leu Gly Ile Thr Ala Leu Trp Leu Pro Pro Ala Tyr Lys
            35                  40                  45

Gly Thr Ser Arg Ser Asp Val Gly Tyr Gly Val Tyr Asp Leu Tyr Asp
        50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
210                 215                 220

Thr Thr Asn Ile Asp Gly Phe Arg Leu Asp Ala Val Lys His Ile Lys
225                 230                 235                 240
```

```
Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
            500                 505                 510

Ala Trp Pro
        515

<210> SEQ ID NO 9
<211> LENGTH: 591
<212> TYPE: PRT
<213> ORGANISM: Talaromyces emersonii

<400> SEQUENCE: 9

Ala Thr Gly Ser Leu Asp Ser Phe Leu Ala Thr Glu Thr Pro Ile Ala
1               5                   10                  15

Leu Gln Gly Val Leu Asn Asn Ile Gly Pro Asn Gly Ala Asp Val Ala
            20                  25                  30

Gly Ala Ser Ala Gly Ile Val Val Ala Ser Pro Ser Arg Ser Asp Pro
        35                  40                  45

Asn Tyr Phe Tyr Ser Trp Thr Arg Asp Ala Ala Leu Thr Ala Lys Tyr
    50                  55                  60

Leu Val Asp Ala Phe Ile Ala Gly Asn Lys Asp Leu Glu Gln Thr Ile
65                  70                  75                  80

Gln Gln Tyr Ile Ser Ala Gln Ala Lys Val Gln Thr Ile Ser Asn Pro
                85                  90                  95
```

```
Ser Gly Asp Leu Ser Thr Gly Gly Leu Gly Glu Pro Lys Phe Asn Val
            100                 105                 110

Asn Glu Thr Ala Phe Thr Gly Pro Trp Gly Arg Pro Gln Arg Asp Gly
            115                 120                 125

Pro Ala Leu Arg Ala Thr Ala Leu Ile Ala Tyr Ala Asn Tyr Leu Ile
            130                 135                 140

Asp Asn Gly Glu Ala Ser Thr Ala Asp Glu Ile Ile Trp Pro Ile Val
145                 150                 155                 160

Gln Asn Asp Leu Ser Tyr Ile Thr Gln Tyr Trp Asn Ser Ser Thr Phe
                165                 170                 175

Asp Leu Trp Glu Glu Val Glu Gly Ser Ser Phe Phe Thr Ala Val
                180                 185                 190

Gln His Arg Ala Leu Val Glu Gly Asn Ala Leu Ala Thr Arg Leu Asn
            195                 200                 205

His Thr Cys Ser Asn Cys Val Ser Gln Ala Pro Gln Val Leu Cys Phe
            210                 215                 220

Leu Gln Ser Tyr Trp Thr Gly Ser Tyr Val Leu Ala Asn Phe Gly Gly
225                 230                 235                 240

Ser Gly Arg Ser Gly Lys Asp Val Asn Ser Ile Leu Gly Ser Ile His
                245                 250                 255

Thr Phe Asp Pro Ala Gly Gly Cys Asp Asp Ser Thr Phe Gln Pro Cys
            260                 265                 270

Ser Ala Arg Ala Leu Ala Asn His Lys Val Val Thr Asp Ser Phe Arg
            275                 280                 285

Ser Ile Tyr Ala Ile Asn Ser Gly Ile Ala Glu Gly Ser Ala Val Ala
            290                 295                 300

Val Gly Arg Tyr Pro Glu Asp Val Tyr Gln Gly Gly Asn Pro Trp Tyr
305                 310                 315                 320

Leu Ala Thr Ala Ala Ala Glu Gln Leu Tyr Asp Ala Ile Tyr Gln
                325                 330                 335

Trp Lys Lys Ile Gly Ser Ile Ser Ile Thr Asp Val Ser Leu Pro Phe
                340                 345                 350

Phe Gln Asp Ile Tyr Pro Ser Ala Ala Val Gly Thr Tyr Asn Ser Gly
            355                 360                 365

Ser Thr Thr Phe Asn Asp Ile Ile Ser Ala Val Gln Thr Tyr Gly Asp
            370                 375                 380

Gly Tyr Leu Ser Ile Val Glu Lys Tyr Thr Pro Ser Asp Gly Ser Leu
385                 390                 395                 400

Thr Glu Gln Phe Ser Arg Thr Asp Gly Thr Pro Leu Ser Ala Ser Ala
                405                 410                 415

Leu Thr Trp Ser Tyr Ala Ser Leu Leu Thr Ala Ser Ala Arg Arg Gln
                420                 425                 430

Ser Val Val Pro Ala Ser Trp Gly Glu Ser Ser Ala Ser Ser Val Pro
            435                 440                 445

Ala Val Cys Ser Ala Thr Ser Ala Thr Gly Pro Tyr Ser Thr Ala Thr
            450                 455                 460

Asn Thr Val Trp Pro Ser Ser Gly Ser Gly Ser Ser Thr Thr Thr Ser
465                 470                 475                 480

Ser Ala Pro Cys Thr Thr Pro Thr Ser Val Ala Val Thr Phe Asp Glu
                485                 490                 495

Ile Val Ser Thr Ser Tyr Gly Glu Thr Ile Tyr Leu Ala Gly Ser Ile
            500                 505                 510
```

```
Pro Glu Leu Gly Asn Trp Ser Thr Ala Ser Ala Ile Pro Leu Arg Ala
            515                 520                 525

Asp Ala Tyr Thr Asn Ser Asn Pro Leu Trp Tyr Val Thr Val Asn Leu
530                 535                 540

Pro Pro Gly Thr Ser Phe Glu Tyr Lys Phe Lys Asn Gln Thr Asp
545                 550                 555                 560

Gly Thr Ile Val Trp Glu Asp Pro Asn Arg Ser Tyr Thr Val Pro
                565                 570                 575

Ala Tyr Cys Gly Gln Thr Thr Ala Ile Leu Asp Asp Ser Trp Gln
                580                 585                 590

<210> SEQ ID NO 10
<211> LENGTH: 556
<212> TYPE: PRT
<213> ORGANISM: Trametes cingulata

<400> SEQUENCE: 10

Gln Ser Ser Ala Ala Asp Ala Tyr Val Ala Ser Glu Ser Pro Ile Ala
1               5                   10                  15

Lys Ala Gly Val Leu Ala Asn Ile Gly Pro Ser Gly Ser Lys Ser Asn
            20                  25                  30

Gly Ala Lys Ala Gly Ile Val Ile Ala Ser Pro Ser Thr Ser Asn Pro
        35                  40                  45

Asn Tyr Leu Tyr Thr Trp Thr Arg Asp Ser Ser Leu Val Phe Lys Ala
50                  55                  60

Leu Ile Asp Gln Phe Thr Thr Gly Glu Asp Thr Ser Leu Arg Thr Leu
65                  70                  75                  80

Ile Asp Glu Phe Thr Ser Ala Glu Ala Ile Leu Gln Gln Val Pro Asn
                85                  90                  95

Pro Ser Gly Thr Val Ser Thr Gly Leu Gly Glu Pro Lys Phe Asn
            100                 105                 110

Ile Asp Glu Thr Ala Phe Thr Asp Ala Trp Gly Arg Pro Gln Arg Asp
        115                 120                 125

Gly Pro Ala Leu Arg Ala Thr Ala Ile Ile Thr Tyr Ala Asn Trp Leu
130                 135                 140

Leu Asp Asn Lys Asn Thr Thr Tyr Val Thr Asn Thr Leu Trp Pro Ile
145                 150                 155                 160

Ile Lys Leu Asp Leu Asp Tyr Val Ala Ser Asn Trp Asn Gln Ser Thr
                165                 170                 175

Phe Asp Leu Trp Glu Glu Ile Asn Ser Ser Ser Phe Phe Thr Thr Ala
            180                 185                 190

Val Gln His Arg Ala Leu Arg Glu Gly Ala Thr Phe Ala Asn Arg Ile
        195                 200                 205

Gly Gln Thr Ser Val Val Ser Gly Tyr Thr Thr Gln Ala Asn Asn Leu
210                 215                 220

Leu Cys Phe Leu Gln Ser Tyr Trp Asn Pro Thr Gly Gly Tyr Ile Thr
225                 230                 235                 240

Ala Asn Thr Gly Gly Gly Arg Ser Gly Lys Asp Ala Asn Thr Val Leu
                245                 250                 255

Thr Ser Ile His Thr Phe Asp Pro Ala Ala Gly Cys Asp Ala Val Thr
            260                 265                 270

Phe Gln Pro Cys Ser Asp Lys Ala Leu Ser Asn Leu Lys Val Tyr Val
        275                 280                 285

Asp Ala Phe Arg Ser Ile Tyr Ser Ile Asn Ser Gly Ile Ala Ser Asn
290                 295                 300
```

```
Ala Ala Val Ala Thr Gly Arg Tyr Pro Glu Asp Ser Tyr Met Gly Gly
305                 310                 315                 320
Asn Pro Trp Tyr Leu Thr Thr Ser Ala Val Ala Glu Gln Leu Tyr Asp
                325                 330                 335
Ala Leu Ile Val Trp Asn Lys Leu Gly Ala Leu Asn Val Thr Ser Thr
            340                 345                 350
Ser Leu Pro Phe Phe Gln Gln Phe Ser Ser Gly Val Thr Val Gly Thr
            355                 360                 365
Tyr Ala Ser Ser Ser Ser Thr Phe Lys Thr Leu Thr Ser Ala Ile Lys
    370                 375                 380
Thr Phe Ala Asp Gly Phe Leu Ala Val Asn Ala Lys Tyr Thr Pro Ser
385                 390                 395                 400
Asn Gly Gly Leu Ala Glu Gln Tyr Ser Arg Ser Asn Gly Ser Pro Val
                405                 410                 415
Ser Ala Val Asp Leu Thr Trp Ser Tyr Ala Ala Leu Thr Ser Phe
                420                 425                 430
Ala Ala Arg Ser Gly Lys Thr Tyr Ala Ser Trp Gly Ala Ala Gly Leu
        435                 440                 445
Thr Val Pro Thr Thr Cys Ser Gly Ser Gly Ala Gly Thr Val Ala
    450                 455                 460
Val Thr Phe Asn Val Gln Ala Thr Thr Val Phe Gly Glu Asn Ile Tyr
465                 470                 475                 480
Ile Thr Gly Ser Val Pro Ala Leu Gln Asn Trp Ser Pro Asp Asn Ala
                485                 490                 495
Leu Ile Leu Ser Ala Ala Asn Tyr Pro Thr Trp Ser Ile Thr Val Asn
                500                 505                 510
Leu Pro Ala Ser Thr Thr Ile Glu Tyr Lys Tyr Ile Arg Lys Phe Asn
            515                 520                 525
Gly Ala Val Thr Trp Glu Ser Asp Pro Asn Asn Ser Ile Thr Thr Pro
        530                 535                 540
Ala Ser Gly Thr Phe Thr Gln Asn Asp Thr Trp Arg
545                 550                 555
```